US009322021B2

(12) United States Patent
Revenko et al.

(10) Patent No.: US 9,322,021 B2
(45) Date of Patent: Apr. 26, 2016

(54) METHODS FOR MODULATING KALLIKREIN (KLKB1) EXPRESSION

(75) Inventors: Alexey Revenko, San Diego, CA (US); Gourab Bhattacharjee, San Diego, CA (US); Robert A. MacLeod, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 127 days.

(21) Appl. No.: 14/129,039

(22) PCT Filed: Jun. 29, 2012

(86) PCT No.: PCT/US2012/045105
§ 371 (c)(1),
(2), (4) Date: Mar. 25, 2014

(87) PCT Pub. No.: WO2013/003808
PCT Pub. Date: Jan. 3, 2013

(65) Prior Publication Data

US 2014/0206745 A1 Jul. 24, 2014

Related U.S. Application Data

(60) Provisional application No. 61/502,739, filed on Jun. 29, 2011.

(51) Int. Cl.

| | |
|---|---|
| ***A61K 31/70*** | (2006.01) |
| ***C07H 21/02*** | (2006.01) |
| ***C07H 21/04*** | (2006.01) |
| ***C12N 15/113*** | (2010.01) |
| ***A61K 31/7125*** | (2006.01) |
| ***A61K 45/06*** | (2006.01) |
| *C12N 5/00* | (2006.01) |

(52) U.S. Cl.
CPC ........ *C12N 15/1137* (2013.01); *A61K 31/7125* (2013.01); *A61K 45/06* (2013.01); *C12N 15/113* (2013.01); *C12N 2310/11* (2013.01); *C12N 2310/315* (2013.01); *C12N 2310/322* (2013.01); *C12N 2310/3231* (2013.01); *C12N 2310/341* (2013.01); *C12N 2310/345* (2013.01)

(58) Field of Classification Search
None
See application file for complete search history.

(56) References Cited

U.S. PATENT DOCUMENTS

| | | | |
|---|---|---|---|
| 4,153,687 | A | 5/1979 | Schnabel et al. |
| 4,973,668 | A | 11/1990 | Jallat et al. |
| 4,981,957 | A | 1/1991 | Lebleu et al. |
| 5,034,506 | A | 7/1991 | Summerton et al. |
| 5,118,800 | A | 6/1992 | Smith et al. |
| 5,166,315 | A | 11/1992 | Summerton et al. |
| 5,185,444 | A | 2/1993 | Summerton et al. |
| 5,319,080 | A | 6/1994 | Leumann |
| 5,359,044 | A | 10/1994 | Cook et al. |
| 5,393,878 | A | 2/1995 | Leumann |
| 5,446,137 | A | 8/1995 | Maag et al. |
| 5,466,786 | A | 11/1995 | Buhr et al. |
| 5,514,785 | A | 5/1996 | Van Ness et al. |
| 5,519,134 | A | 5/1996 | Acevedo et al. |
| 5,567,811 | A | 10/1996 | Misiura et al. |
| 5,576,427 | A | 11/1996 | Cook et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,670,633 | A | 9/1997 | Cook et al. |
| 5,698,685 | A | 12/1997 | Summerton et al. |
| 5,700,920 | A | 12/1997 | Altmann et al. |
| 5,786,328 | A | 7/1998 | Dennis et al. |
| 5,792,847 | A | 8/1998 | Buhr et al. |
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |

(Continued)

FOREIGN PATENT DOCUMENTS

| | | |
|---|---|---|
| WO | WO 98/03665 | 1/1998 |
| WO | WO 98/39352 | 9/1998 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Sean McGarry

(74) *Attorney, Agent, or Firm* — Knobbe, Martens, Olson & Bear, LLP

(57) ABSTRACT

Disclosed herein are methods for decreasing kallikrein and treating or preventing thromboembolic conditions in an individual in need thereof. Examples of disease conditions that can be ameliorated with the administration of antisense compounds targeted to kallikrein include thrombosis, embolism, and thromboembolism, such as, deep vein thrombosis, pulmonary embolism, myocardial infarction, and stroke. Methods for inhibiting kallikrein can also be used as a prophylactic treatment to prevent individuals at risk for thrombosis and embolism.

30 Claims, No Drawings

(56) References Cited

U.S. PATENT DOCUMENTS

| | | | |
|---|---|---|---|
| 7,034,133 B2 | 4/2006 | Wengel et al. | |
| 7,053,207 B2 | 5/2006 | Wengel | |
| 7,235,530 B2 | 6/2007 | Blair et al. | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,696,345 B2 | 4/2010 | Allerson et al. | |
| 2001/0053519 A1 | 12/2001 | Fodor et al. | |
| 2003/0228597 A1 | 12/2003 | Cowsert et al. | |
| 2004/0171570 A1 | 9/2004 | Allerson et al. | |
| 2005/0089893 A1 | 4/2005 | Lopez et al. | |
| 2005/0130923 A1 | 6/2005 | Bhat et al. | |
| 2005/0245475 A1 | 11/2005 | Khvorova et al. | |
| 2005/0246794 A1 | 11/2005 | Khvorova et al. | |
| 2005/0255487 A1 | 11/2005 | Khvorova et al. | |
| 2006/0069020 A1 | 3/2006 | Blair et al. | |
| 2006/0185027 A1 | 8/2006 | Bartel et al. | |
| 2006/0264603 A1 | 11/2006 | Markland et al. | |
| 2007/0031844 A1 | 2/2007 | Khvorova et al. | |
| 2007/0039072 A1 | 2/2007 | Khvorova et al. | |
| 2007/0191296 A1 | 8/2007 | Golz et al. | |
| 2007/0207974 A1 | 9/2007 | Khvorova et al. | |
| 2007/0253949 A1 | 11/2007 | Golz et al. | |
| 2008/0039618 A1 | 2/2008 | Allerson et al. | |
| 2008/0188409 A1 | 8/2008 | Blair et al. | |
| 2008/0221031 A1 | 9/2008 | Blair et al. | |
| 2008/0280811 A1 | 11/2008 | Feener et al. | |
| 2009/0012281 A1 | 1/2009 | Swayze et al. | |
| 2009/0075887 A1 | 3/2009 | McPherson | |
| 2009/0105142 A1 | 4/2009 | Moscicki | |
| 2009/0221480 A1 | 9/2009 | Blair et al. | |
| 2009/0227494 A1 | 9/2009 | Blair et al. | |
| 2009/0227495 A1 | 9/2009 | Blair et al. | |
| 2009/0233852 A1 | 9/2009 | Blair et al. | |
| 2009/0234009 A1 | 9/2009 | Blair et al. | |
| 2009/0247453 A1 | 10/2009 | Blair et al. | |
| 2009/0264350 A1 | 10/2009 | Blair et al. | |
| 2010/0029003 A1 | 2/2010 | Bartel et al. | |
| 2010/0183625 A1 | 7/2010 | Sternlicht | |
| 2011/0200611 A1 | 8/2011 | Sexton | |
| 2011/0301215 A1* | 12/2011 | Sinha et al. | 514/406 |

FOREIGN PATENT DOCUMENTS

| | | |
|---|---|---|
| WO | WO 99/14226 | 3/1999 |
| WO | WO 01/49687 | 7/2001 |
| WO | WO 03/004602 | 1/2003 |
| WO | WO 03/103475 | 12/2003 |
| WO | WO 2004/106356 | 12/2004 |
| WO | WO 2005/021570 | 3/2005 |
| WO | WO 2005/075665 | 8/2005 |
| WO | WO 2005/083110 | 9/2005 |
| WO | WO 2005/121371 | 12/2005 |
| WO | WO 2006/008002 | 1/2006 |
| WO | WO 2006/036860 | 4/2006 |
| WO | WO 2006/047842 | 5/2006 |
| WO | WO 2007/134181 | 11/2007 |
| WO | WO 2008/016883 | 2/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2010/036696 | 4/2010 |
| WO | WO 2011/075684 | 6/2011 |
| WO | WO 2012/170945 | 12/2012 |
| WO | WO 2013/003808 | 1/2013 |

OTHER PUBLICATIONS

Altmann et al., "Second-generation antisense oligonucleoties: structure-activity relationships and the design of improved signal-transduction inhibitors" Biochem. Soc. Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-a and c-RAF Kinase Expression by Chimeric Oligonucleotides Incorporating 5'-Substituted Carbocyclic Nucleosides and 2'-O-Ethylene Glycol Substituted Ribonucleosides" Nucleosides Nucleotides (1997) 16(7-9): 917-926.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18): 11944-12000.

Braasch et al., "Novel Antisense and Peptide Nucleic Acid Strategies for Controlling Gene Expression" Biochemistry (2002) 41(14): 4503-4510.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chao et al., "Novel roles of kallistatin, a specific tissue kallikrein inhibitor, in vascular remodeling." Biol Chem (2001) 382(1): 15-21.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cichon et al., "Increased activity of coagulation factor XII (Hageman factor) causes hereditary angioedema type III." Am. J. Hum. Genet. (2006) 79: 1098-1104.

Crooke et al., "Basic Principles of Antisense Therapeutics" Antisense Research and Application (1998) Chapter 1:1-50.

Cruz-Silva et al., "A proteinase inhibitor from Caesalpinia echinata (pau-brasil) seeds for plasma kallikrein, plasmin and factor XIIa." Biol Chem (2004) 385(11): 1083-1086.

Dowd, "Concomitant antiplatelet and anticoagulation therapy: Indications, controversies and practical advice" Plenary Sessions/ Thrombosis Research (2008) 123, Supplement 1: S11-S15.

Elayadi et al., "Applications of PNA and LNA oligomers to chemotherapy" Curr. Opinion Invest. Drugs (2001) 2:558-561.

Evans et al., "Selective inhibitors of plasma kallikrein" Immunopharmacology (1996) 32(1-3): 115-116.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.

Gigli et al., "Interaction of plasma kallikrein with the C1 inhibitor." J. Immunol. (1970) 104:574-581.

Gonzalez et al., "Purification and preliminary characterization of a plasma kallikrein inhibitor isolated from sea hares *Aplysia dactylomela* Rang, 1828" Toxicon (2004) 43(2): 219-223.

Gu et al., "Base Pairing Properties of D- and L-Cyclohexene Nucleic Acids (CeNA)" Oligonucleotides (2003) 13(6): 479-489.

Gu et al., "Synthesis of enantiomeric-pure cyclohexenyl nucleoside building blocks for oligonucleotide synthesis" Tetrahedron (2004) 60(9): 2111-2123.

Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.

Han et al., "Increased vascular permeability in C1 inhibitor-deficient mice mediated by the bradykinin type 2 receptor." J. Clin. Invest. (2002) 109: 1057-1063.

Horvath et al., "Stereoselective synthesis of (−)-ara-cyclohexenyl-adenine" Tetrahedron Letters (2007) 48: 3621-3623.

Ikarugi et al., "Synergistic antithrombotic effect of a combination of NO donor and plasma kallikrein inhibitor." Thromb Res (2005) 116: 403-408.

Kaplan et al., "Pathways for bradykinin formation and inflammatory disease." J. Allergy Clin. Immunol. (2002) 109(2): 195-209.

Kim et al., "Pretreatment with nafamostat mesilate, a kallikrein inhibitor, to decrease withdrawal response associated with rocuronium." J. Anesth. (2010) 24(4): 549-552.

(56) References Cited

OTHER PUBLICATIONS

Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.
Kubitza et al., "Rivaroxaban (BAY 59-7939)—an oral, direct Factor Xa inhibitor—has no clinically relevant interaction with naproxen" Br. J. Clin. Pharmacol. (2006) 63(4): 469-476.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Leumann, "DNA Analogues: From Supramolecular Principles to Biological Properties" Bioorganic & Medicinal Chemistry (2002) 10:841-854.
Mackenzie et al., "Plasma prekallikrein levels are positively associated with circulating lipid levels and the metabolic syndrome in children." Appl. Physiol. Nutr. Metab. (2010) 35: 518-525.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Martin, "Ein neuer Zugang zu 2'-O-Alkylribonucleosiden and Eigenschaften eren Oligonucleotide" Helv. Chim. Acta (1995) 78: 486-504.
Nakane et al., "Nafamostat mesilate, a kallikrein inhibitor, prevents pain on injection with propofol." Br. J. Aneaesth. (1998) 81(6): 963-964.
Heinis et al., "Phage-encoded combinatorial chemical libraries based on bicyclic peptides." Nat Chem Biol (2009) 5(7): 502-507.
Nauwelaerts et al., "Structural characterization and biological evaluation of small interfering RNAs containing cyclohexenyl nucleosides." J. Am. Chem. Soc. (2007) 129(30): 9340-9348.
Nauwelaerts et al., "Cyclohexenyl nucleic acids: conformationally flexible oligonucleotides" Nucleic Acids Research (2005) 33(8): 2452-2463.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3(3):239-243.
Ravindran et al., "Inhibition of plasma kallikrein by C1-inhibitor: role of endothelial cells and the amino-terminal domain of C1-inhibitor." Thromb Haemost (2004) 92: 1277-1283.
Reynolds et al., "Rational siRNA design for RNA interference" Nature Biotechnology (2004) 22(3):326-330.
Riedl et al., "Response time for ecallantide treatment of acute hereditary angioedema attacks." Ann Allergy Asthma Immunol (2010) 105(6): 430-436.e2.
Robeyns et al., "Oligonucleotides with cyclohexene-nucleoside building blocks: crystallization and preliminary X-ray studies of a left-handed sequence GTGTACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence Gtgtacac" J. Am. Chem. Soc. (2008) 130(6): 1979-1984.
Sanghvi et al., "Heterocyclic Base Modifications in Nucleic Acids and Their Applications in Antisense Oligonucleotides" Antisense Research and Applications (1993) pp. 273-288.
Schneider et al., "Critical role of kalikrein in hereditary angioedema pathogenesis: a clinical trial of escallantide, a novel kallikrein inhibitor" J. Allery Clin. Immunol. (2007) 120(2):416-422.
Scott et al., "Alpha-1-antitrypsin-Pittsburgh. A potent inhibitor of human plasma factor XIa, kallikrein, and factor XIIf." J Clin Invest (1986) 77(2): 631-634.
Sexton et al., "Specific inhibition of tissue kallikrein 1 with a human monoclonal antibody reveals a potential role in airway diseases" Biochem. J. (2009) 422: 383-392.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Srivastava et al., "Five- and Six-Membered Conformationally Locked 2',4'-Carbocyclic riboThymidines: Synthesis, Structure, and Biochemical Studies" J. Am. Che,. Soc. (2007) 129:8362-8379.
Stolz et al., "Ecallantide: a plasma kallikrein inhibitor for the treatment of acute attacks of hereditary angioedema." Drugs Today (2010) 46(8): 547-555.
Stoop et al., "Analysis of an engineered plasma kallikrein inhibitor and its effect on contact activation" Biol Chem 2010; 391(4): 425-433.
Verbeure et al., "RNase H mediated cleavage of RNA by cyclohexene nucleic acid (CeNA)" Nucleic Acids Research (2001) 29(24): 4941-4947.
Wahlestedt et al., "Potent and nontoxic antisense oligonucleoties containing locked nucleic acids" PNAS (2000) 97(10):5633-5638.
Wang et al., "Cyclohexene Nucleic Acids (CeNA): Serum Stable Oligonucleotides that Activate RNase H and Increase Duplex Stability with Complementary RNA" J. Am. Chem. (2000) 122: 8595-8602.
Wang et al., "A Straightforward Stereoselective Synthesis of D- and L-5-Hydroxy-4-hydroxymethyl-2-cyclohexenylguanine" J. Org. Chem. (2001) 66: 8478-8482.
Wang et al., "Stereocontrolled Synthesis of Ara-Type Cyclohexenyl Nucleosides" J. Org. Chem. (2003) 68: 4499-4505.
Wang et al., "Cyclohexene Nucleic Acids (CeNA) Form Stable Duplexes With RNA and Induce RNASE H Activity" Nucleosides, Nucleotides & Nucleic Acids (2001) 20(4-7), 785-788.
Wong et al. "Arterial antithrombotic and bleeding time effects of apixaban, a direct factor Xa inhibitor, in combination with antiplatelet therapy in rabbits" Journal of Thrombosis and Haemostasis (2008) 6: 1736-1741.
Wolf et al., "A synthetic tissue kallikrein inhibitor suppresses cancer cell invasiveness." Am J Pathol (2001) 159: 1797-1805.
Woolf et al., "Specificity of antisense oligonucleotides in vivo" PNAS (1992) 89:7305-7309.
Wulf et al., "CU-2010—A Novel Small Molecule Protease Inhibitor with Antifibrinolytic and Anticoagulant Properties" Anesthesiology (2009) 110(1): 123-130.
Zhou et al., "Kallistatin: a novel human tissue kallikrein inhibitor. Purification, characterization, and reactive center sequence." J. Biol. Chem. (1992) 267(36): 25873-25880.
Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.
Zuraw, "Hereditary Angioedema" N. Engl. J. Med. (2008) 359: 1027-36.
International Search Report for application PCT/US12/45105 dated Sep. 25, 2012.
International Search Report for application PCT/US12/41743 dated Nov. 20, 2012.
Bhattacharjee et al., "Inhibition of Vascular Permeability by Antisense-Mediated Inhibition of Plasma Kallikrein and Coagulaton Factor 12" Nucleic Acid Therapeutics (2013) 23(3): 175-187.
Revenko et al., "Selective depletion of plasma prekallikrein or coagulation factor XII inhibits thrombosis in mice without increased risk of bleeding" Blood (2011) 118(19): 5302-5311.
European Search Report for application EP 12804096.1 dated Dec. 15, 2014.

* cited by examiner

METHODS FOR MODULATING KALLIKREIN (KLKB1) EXPRESSION

CROSS REFERENCED TO RELATED APPLICATIONS

This application is a U.S. National Phase filing under 35 U.S.C. §371 claiming priority to International Serial No. PCT/US2012/045105 filed Jun. 29, 2012, which claims priority to U.S. Provisional Application 61/502,739, filed Jun. 29, 2011, each of which is incorporated herein by reference in its entirety.

SEQUENCE LISTING

The present application is being filed along with a Sequence Listing in electronic format. The Sequence Listing is provided as a file entitled BIOL0141USA_ST25.TXT, created Dec. 20, 2013, which is 232 Kb in size. The information in the electronic format of the sequence listing is incorporated herein by reference in its entirety.

FIELD

Embodiments of the present invention provide methods for reducing expression of kallikrein (KLKB1) mRNA and protein in an animal. Such methods are useful to treat, prevent, or ameliorate thromboembolic conditions.

BACKGROUND

Coagulation

The blood coagulation system responds to vascular injury with local production of a clot formed of fibrin mesh and activated platelets. While this process is essential for hemostasis, dysregulated coagulation can lead to blood vessel occlusion (thrombosis), precipitating life-threatening events such as myocardial infarction, stroke and venous thromboembolism. In the classical view of blood coagulation, thrombin generation and fibrin formation can be initiated by two distinct mechanisms referred to as the extrinsic and intrinsic pathways (Davie, E. W. et al. Science. 145:1310-1312, 1964; Macfarlane, R. G. Nature. 202:498-499, 1964).

The extrinsic pathway involves binding of plasma factor Vila (NM) to extravascular tissue factor (TF) at a site of vessel injury (Mackman, N. Arterioscler Thromb Vasc Biol. 24:1015-1022, 2004). The first step in the intrinsic pathway requires the surface-dependent activation of plasma factor XII (fXII) to fXIIa in a process called contact activation (Gailani, D., et al. J. Thromb. Haemost. 5:1106-1112, 2007; Schmaier, A. H. et al. J. Thromb. Haemost. 5:2323-2329, 2007). Contact activation involves two other proteins, prekallikrein (PKK) and high molecular weight kininogen (HK). HK serves as a docking molecule for PKK on the contact surface. PKK is cleaved by fXIIa to form the protease α-kallikrein, which in turn cleaves fXII to generate additional fXIIa. Collectively, fXII, PKK, and HK comprise the plasma contact system. FXIIa generated by contact activation can activate factor XI (fXI) to fXIa, triggering a series of proteolytic cleavage events that culminates in thrombin generation and fibrin clot formation.

The plasma kallikrein/kinin system that consists of the proteins factor XII, prekallikrein, and high molecular weight kininogen was first recognized as a surface-activated coagulation system arising when blood or plasma interacts with artificial surfaces (Sainz et al. *Thromb. Haemost.* 2007; 98:77-83). The kallikrein-kinin system is a component of the intrinsic pathway of blood coagulation along with factors XI, IX, and VIII. These proteins have subsequently been shown to have roles in fibrinolysis, thrombin-induced platelet activation, control of blood pressure, cell adhesion and angiogenesis (Schmaier et al. *Curr. Opin. Hematol.* 2000; 7:261-265).

Kallikrein

Plasma prekallikrein is the precursor of plasma kallikrein, which in turn liberates kinins from kininogens and also generates plasmin from plasminogen. Plasma prekallikrein is converted to plasma kallikrein by Factor 12a by the cleavage of an internal Arg-Ile peptide bond. Plasma prekallikrein, in turn, is the product of the KLKB1 gene (MacKenzie, J. A. et al. Appl. Physiol. Nutr. Metab. 35: 518-525, 2010). Plasma kallikrein works in association with Factors 11 and 12.

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year (Adcock et al. *American Journal of Clinical Pathology.* 1997; 108:434-49). While most cases of thrombosis are due to acquired extrinsic problems, for example, surgery, cancer, and immobility, some cases are due to a genetic predisposition, for example, antiphospholipid syndrome and the autosomal dominant condition, Factor V Leiden (Bertina R M et al. *Nature* 1994; 369:64-67).

Treatment

The most commonly used anticoagulants, warfarin, heparin, and low molecular weight heparin (LMWH) all possess significant drawbacks.

Warfarin is typically used to treat patients suffering from atrial fibrillation. The drug interacts with vitamin K-dependent coagulation factors which include factors II, VII, IX, and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182). Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor II, but to a lesser degree than unfractioned heparin (UFH). LMWH has been implicated in the development of HIT.

Thus, current approved anticoagulant agents lack predictability and specificity and, therefore, require careful patient monitoring to prevent adverse side effects, such as bleeding complications. There are currently no approved anticoagulants which target only the intrinsic or extrinsic pathway.

SUMMARY

Provided herein are methods for modulating expression of kallikrein mRNA and protein. In certain embodiments, kallikrein specific inhibitors modulate kallikrein mRNA and protein expression or activity. In certain embodiments, kallikrein specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, kallikrein mRNA levels are reduced. In certain embodiments, kallikrein protein levels are reduced. In certain embodiments, kallikrein mRNA and protein levels are reduced. Such reduction can occur in a time-dependent manner or in a dose-dependent manner.

Also provided are methods useful for preventing, treating, and ameliorating diseases, disorders, and conditions. In certain embodiments, such diseases, disorders, and conditions are thromboembolic conditions. Such thromboembolic conditions include the categories of thrombosis, embolism, and thromboembolism. In certain embodiments such thromboembolic conditions include deep vein thrombosis, pulmonary embolism, myocardial infarction, and stroke.

Such diseases, disorders, and conditions can have one or more risk factors, causes, or outcomes in common. Certain risk factors and causes for development of a thromboembolic condition include immobility, surgery (particularly orthopedic surgery), malignancy, pregnancy, older age, use of oral contraceptives, atrial fibrillation, previous thromboembolic condition, chronic inflammatory disease, and inherited or acquired prothrombotic clotting disorders. Certain outcomes associated with development of a thromboembolic condition include decreased blood flow through an affected vessel, death of tissue, and death.

In certain embodiments, methods of treatment include administering a kallikrein specific inhibitor to an individual in need thereof. In certain embodiments, the kallikrein specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of kallikrein", it is implied that the kallikrein levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to kallikrein is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antidote compound" refers to a compound capable of decreasing the intensity or duration of any antisense-mediated activity.

"Antidote oligonucleotide" means an antidote compound comprising an oligonucleotide that is complementary to and capable of hybridizing with an antisense compound.

"Antidote protein" means an antidote compound comprising a peptide.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, and shRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Coagulation factor" means any of factors I, II, III, IV, V, VII, VIII, IX, X, XI, XII, XIII, TAFI, or kallikrein in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Kallikrein" means any nucleic acid or protein of KLKB1. In certain embodiments, KLKB1 is the term generally associated with the gene. In certain embodiments, the expression product of KLKB1 translation is generally termed plasma prekallikrein. Plasma prekallikrein is cleaved by Factor 12a. In certain embodiments, the cleavage product is generally termed plasma kallikrein. Plasma kallikrein is the substrate that C1-INH acts upon. As used herein, "kallikrein" means KLKB1 and its expression products, including, for example plasma prekallikrein and plasma kallikrein.

"Kallikrein nucleic acid" (aka KLKB1, plasma prekallikrein, plasma kallikrein, Fletcher factor, kallikrein B) means any nucleic acid encoding kallikrein. For example, in certain embodiments, a kallikrein nucleic acid includes a DNA sequence encoding kallikrein, an RNA sequence transcribed from DNA encoding kallikrein (including genomic DNA comprising introns and exons), and an mRNA sequence encoding kallikrein. "Kallikrein mRNA" means an mRNA encoding a kallikrein protein.

"Kallikrein specific inhibitor" refers to any agent capable of specifically inhibiting kallikrein mRNA and/or kallikrein protein expression or activity at the molecular level. For example, kallikrein specific inhibitors include nucleic acids (including antisense compounds), peptides, antibodies, small molecules, and other agents capable of inhibiting the expression of kallikrein mRNA and/or kallikrein protein. In certain embodiments, by specifically modulating kallikrein mRNA expression and/or kallikrein protein expression, kallikrein specific inhibitors may affect other components of the coagulation cascade including downstream components. Similarly, in certain embodiments, kallikrein specific inhibitors may affect other molecular processes in an animal.

"Kallikrein specific inhibitor antidote" means a compound capable of decreasing the effect of a kallikrein specific inhibitor. In certain embodiments, a kallikrein specific inhibitor antidote is selected from a kallikrein peptide; a kallikrein antidote oligonucleotide, including a kallikrein antidote compound complementary to a kallikrein antisense compound; and any compound or protein that affects the intrinsic or extrinsic coagulation pathway.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for thromboembolic conditions" means identifying an animal having been diagnosed with a thromboembolic condition or identifying an animal predisposed to develop a thromboembolic condition. Individuals predisposed to develop a thromboembolic condition include those having one or more risk factors for thromboembolic conditions including immobility, surgery (particularly orthopedic surgery), malignancy, pregnancy, older age, use of oral contraceptives, and inherited or acquired prothrombotic clotting disorders. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inhibiting kallikrein" means reducing expression of kallikrein mRNA and/or protein levels in the presence of a kallikrein specific inhibitor, including a kallikrein antisense oligonucleotide, as compared to expression of kallikrein mRNA and/or protein levels in the absence of a kallikrein specific inhibitor, such as a kallikrein antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P═S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Thromboembolic condition" means any disease, disorder, or condition involving an embolism caused by a thrombus. Examples of such diseases, disorders, and conditions include the categories of thrombosis, embolism, and thromboembolism. In certain embodiments, such disease disorders, and conditions include deep vein thrombosis, pulmonary embolism, myocardial infarction, and stroke.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods for decreasing kallikrein mRNA and protein expression.

Certain embodiments provide methods for the treatment, prevention, or amelioration of diseases, disorders, and conditions associated with kallikrein in an individual in need thereof. Also contemplated are methods for the preparation of a medicament for the treatment, prevention, or amelioration of a disease, disorder, or condition associated with kallikrein. Kallikrein associated diseases, disorders, and conditions include thromboembolic conditions such as thrombosis, embolism, thromboembolism, deep vein thrombosis, pulmonary embolism, myocardial infarction, and stroke.

Certain embodiments provide for the use of a kallikrein specific inhibitor for treating, preventing, or ameliorating a kallikrein associated disease. In certain embodiments, kallikrein specific inhibitors are nucleic acids (including antisense compounds), peptides, antibodies, small molecules, and other agents capable of inhibiting the expression of kallikrein mRNA and/or kallikrein protein.

In certain embodiments, kallikrein specific inhibitors are peptides or proteins, such as, but not limited to, lympho-epithelial Kazal-type-related inhibitor (LEKTI) as described in *J Proteome Res* 2010; 9: 4389-4394; ecotin-Pkal as described in *Biol Chem* 2010; 391: 425-433; aprotinin as described in *J Hypertens* 1987; 5: 581-586; PK15 as described in *Nat Chem Biol* 2009; 5: 502-507; kallistatin as described in *Biol Chem* 2001; 382: 15-21 and *J Biol Chem* 1992; 267: 25873-25880; C1-inhibitor as described in *Thromb Haemost* 2004; 92: 1277-1283 and *Adv Biosci* 1978; 17: 93-101; CeKI as described in *Biol Chem* 2004; 385: 1083-1086; AdKi as described in *Toxicon* 2004; 43: 219-223; FE999024 as described in *Am J Pathol* 2001; 159: 1797-1805; Arginine-15-aprotinin as described in *Adv Exp Med Biol* 1989; 247B: 15-21; alpha-1-antitrypsin-Pittsburgh as described in *J Clin Invest* 1986; 77: 631-634; and kallikrein inhibitors as described in U.S. Pat. No. 7,235,530, USPPN 2006/0069020, USPPN 2008/0188409, USPPN 2008/0221031, USPPN 2009/0221480, USPPN 2009/0227494, USPPN 2009/0227495, USPPN 2009/0233852, USPPN 2009/0234009, USPPN 2009/0247453, USPPN 2009/0264350, USPPN 2009/0075887; USPPN 2009/0105142, USPPN 2010/0183625, and U.S. Pat. No. 4,973,668.

In certain embodiments, kallikrein specific inhibitors are antibodies, such as, but not limited to, DX-2300 as described in *Biochem J* 2009; 422: 383-392.

In certain embodiments, kallikrein specific inhibitors are small molecules, such as, but not limited to, Ecallantide (DX-88 by Dyax Corp) as described in *Ann Allergy Asthma Immunol* 2010; 105: 430-436 and Drugs Today 2010; 46: 547-555; Nafamostat mesilate as described in *J Anesth* 2010; 24: 549-552 and *Br J Aneaesth* 1998; 81: 963-964; CU-2010 as described in *Anesthesiology* 2009; 110: 123-130; VA999024 and VA999026 as described in *Immunopharmacology* 1996; 32: 115-118; PKSI-527 (trans-4-aminomethyl-cyclohexanecarbonylphenylalanine 4-carboxymethylanilide hydrochloride) as described in *Thromb Res* 2005; 116: 403-408; and kallikrein inhibitors as described in U.S. Pat. No. 4,153,687.

Certain embodiments provide for methods of treating, preventing, or ameliorating a thromboembolic condition in an animal, comprising administering to the animal a therapeutically effective amount of a kallikrein specific inhibitor, wherein the thromboembolic condition is ameliorated in the animal.

In certain embodiments, the animal is a human.

In certain embodiments, the thromboembolic condition is any of the group consisting of thrombosis, embolism, thromboembolism, deep vein thrombosis, pulmonary embolism, myocardial infarction, and stroke.

In certain embodiments, the kallikrein specific inhibitor is an antisense compound. In certain embodiments, the antisense compound is a modified oligonucleotide.

In certain embodiments, the kallikrein specific inhibitor is a nucleic acid. In certain embodiments, the nucleic acid is a modified oligonucleotide.

In certain embodiments, the kallikrein specific inhibitor is a modified oligonucleotide.

In certain embodiments, the modified oligonucleotide consists of 12 to 30 linked nucleosides.

In certain embodiments, the modified oligonucleotide is a single-stranded oligonucleotide.

In certain embodiments, the modified oligonucleotide consists of 15, 16, 17, 18, 19, or 20 linked nucleosides.

In certain embodiments, the modified oligonucleotide has a nucleobase sequence that is 80%, 85%, 90%, 95%, or 100% complementary to a human kallikrein nucleic acid.

In certain embodiments, the modified oligonucleotide comprises at least one modified internucleoside linkage. In certain embodiments, each modified internucleoside linkage is a phosphorothioate internucleoside linkage.

In certain embodiments, at least one nucleoside of the modified oligonucleotide comprises a modified sugar. In certain embodiments, the modified sugar is a bicyclic sugar. In certain embodiments, the bicyclic sugar comprises a 4'-$CH(CH_3)$—O-2' bridge, a 4'-$(CH_2)$—O-2' bridge, or 4'-$(CH_2)_2$—O-2' bridge.

In certain embodiments, the modified sugar comprises a 2'-O-methoxyethyl group.

In certain embodiments, at least one nucleoside of the modified oligonucleotide comprises a modified nucleobase. In certain embodiments, the modified nucleobase is a 5'-methylcytosine.

In certain embodiments, at least one nucleoside of the modified oligonucleotide comprises at least one tetrahydropyran modified nucleoside wherein a tetrahydropyran ring replaces the furanose ring. In certain embodiments, each of the at least one tetrahydropyran modified nucleoside has the structure:

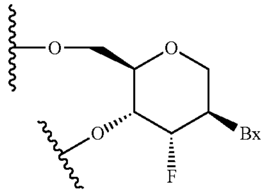

wherein Bx is an optionally protected heterocyclic base moiety.

In certain embodiments, the modified oligonucleotide of the compound comprises:

(i) a gap segment consisting of linked deoxynucleosides;

(ii) a 5' wing segment consisting of linked nucleosides;

(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:

(i) a gap segment consisting of ten linked deoxynucleosides;

(ii) a 5' wing segment consisting of five linked nucleosides;

(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Embodiments described herein provide for methods comprising (1) identifying an animal at risk for a thromboembolic condition; and (2) administering to the at risk animal a therapeutically effective amount of a modified oligonucleotide consisting of 12 to 30 linked nucleosides, wherein the modified oligonucleotide is at least 80% complementary to a kallikrein nucleic acid. In certain embodiments, the modified oligonucleotide is at least 90% complementary to a human kallikrein nucleic acid. In certain embodiments, the modified oligonucleotide is 100% complementary to a human kallikrein nucleic acid.

Embodiments described herein provide for methods comprising treating a thromboembolic condition in an animal by administering to the animal a therapeutically effective amount of a kallikrein specific inhibitor. Further embodiments described herein provide for methods comprising treating a thromboembolic condition in an animal by administering to the animal a therapeutically effective amount of a modified oligonucleotide consisting of 12 to 30 linked nucleosides, wherein the modified oligonucleotide is at least 90% complementary to a kallikrein nucleic acid.

Embodiments described herein provide for methods comprising inhibiting thrombus formation in an animal by administering to the animal a therapeutically effective amount of a kallikrein specific inhibitor. Further embodiments described herein provide for methods comprising treating a thromboembolic condition in an animal by administering to the animal a therapeutically effective amount of a modified oligonucleotide consisting of 12 to 30 linked nucleosides, wherein the modified oligonucleotide is at least 90% complementary to a kallikrein nucleic acid.

In certain embodiments, the administering of a kallikrein specific inhibitor inhibits thrombus and clot formation. In further embodiments, the administering of a modified oligonucleotide inhibits thrombus and clot formation.

In certain embodiments, the administering of a kallikrein specific inhibitor prolongs aPTT. In further embodiments, the administering of a modified oligonucleotide prolongs aPTT In certain embodiments, the administering of a kallikrein specific inhibitor does not prolong PT. In further embodiments, the administering of a modified oligonucleotide does not prolong PT.

In certain embodiments, the administering of a kallikrein specific inhibitor prolongs aPTT and does not prolong PT. In further embodiments, the administering of a modified oligonucleotide prolongs aPTT and does not prolong PT.

In certain embodiments, the administering of a kallikrein specific inhibitor decreases Platelet Factor 4 (PF-4). In further embodiments, the administering of a modified oligonucleotide decreases Platelet Factor 4 (PF-4).

In certain embodiments, the administering of a kallikrein specific inhibitor increases time for thrombus formation. In further embodiments, the administering of a modified oligonucleotide increases time for thrombus formation.

In certain embodiments, the administering of a kallikrein specific inhibitor reduces platelet aggregation. In further embodiments, the administering of a modified oligonucleotide reduces platelet aggregation.

In certain embodiments, the administering of a kallikrein specific inhibitor reduces fibrin formation. In further embodiments, the administering of a modified oligonucleotide reduces fibrin formation.

In certain embodiments, the administering of a kallikrein specific inhibitor does not increase bleeding in the at risk, treated animal as compared to an animal not administered a kallikrein specific inhibitor.

In certain embodiments, the administering of a modified oligonucleotide does not increase bleeding in the at risk, treated animal as compared to an animal not administered a modified oligonucleotide.

In certain embodiments, the animal is a human.

In certain embodiments, the kallikrein nucleic acid is a human kallikrein nucleic acid.

In certain embodiments, the thromboembolic condition is any of the group consisting of thrombosis, embolism, thromboembolism, deep vein thrombosis, pulmonary embolism, myocardial infarction, stroke, or a combination thereof.

In certain embodiments, the kallikrein specific inhibitor is co-administered with any of the group selected from aspirin, clopidogrel, dipyridamole, heparin, lepirudin, ticlopidine, warfarin, apixaban, rivaroxaban, and LOVENOX.

In certain embodiments, the kallikrein specific inhibitor is co-administered with an anti-platelet therapy. In certain embodiments, the anti-platelet therapy is any of the group selected from an ADP receptor inhibitor, NSAID, phosphodiesterase inhibitor, glycoprotein IIB/IIIA inhibitor, adenosine reuptake inhibitor, or a combination thereof. In certain embodiments, the NSAID is aspirin, naproxen, or a combination of both.

In certain embodiments, the kallikrein specific inhibitor is concomitantly administered with any of the group selected from aspirin, clopidogrel, dipyridamole, heparin, lepirudin, ticlopidine, warfarin, apixaban, rivaroxaban, and LOVENOX.

In certain embodiments, the kallikrein specific inhibitor is concomitantly administered with an anti-platelet therapy. In certain embodiments, the anti-platelet therapy is any of the group selected from an ADP receptor inhibitor, NSAID, phosphodiesterase inhibitor, glycoprotein IIB/IIIA inhibitor, adenosine reuptake inhibitor, or a combination thereof. In certain embodiments, the NSAID is aspirin, naproxen, or a combination of both.

In certain embodiments, the administering is parenteral administration. In certain embodiments, the parenteral administration is any of subcutaneous or intravenous administration.

Certain embodiments provide the use of kallikrein specific inhibitors as described herein in the manufacture of a medicament for treating, ameliorating, or preventing a thromboembolic condition such as thrombosis, embolism, thromboembolism, deep vein thrombosis, pulmonary embolism, myocardial infarction, and stroke.

Certain embodiments provide the use of a kallikrein specific inhibitor as described herein for treating, ameliorating, or preventing a thromboembolic condition such as thrombosis, embolism, thromboembolism, deep vein thrombosis, pulmonary embolism, myocardial infarction, and stroke.

Certain embodiments provide the use of a kallikrein specific inhibitor as described herein in the manufacture of a medicament for treating, preventing, or ameliorating a thromboembolic condition as described herein in a patient who is subsequently administered an additional agent or therapy as described herein.

Certain embodiments provide the use of a kallikrein specific inhibitor as described herein for treating, preventing, or ameliorating a thromboembolic condition as described herein in a patient who is subsequently administered an additional agent or therapy as described herein.

Certain embodiments provide a kit for treating, preventing, or ameliorating a thromboembolic condition as described herein wherein the kit comprises:

(i) a kallikrein specific inhibitor as described herein; and alternatively (ii) an additional agent or therapy as described herein.

A kit as described herein may further include instructions for using the kit to treat, prevent, or ameliorate a thromboembolic condition as described herein by combination therapy as described herein.

In certain embodiments, the invention provides a compound comprising a modified oligonucleotide. In certain embodiments, the compound of the invention comprises a modified oligonucleotide consisting of 12 to 30 linked nucleosides.

In certain embodiments, the modified oligonucleotide targets a kallikrein nucleic acid. In certain embodiments, the kallikrein nucleic acid may be selected from, but is not limited to, one or more of GENBANK Accession No. NM_000892.3 (incorporated herein as SEQ ID NO: 1), GENBANK Accession No. DC412984.1 (incorporated herein as SEQ ID NO: 2), GENBANK Accession No. CN265612.1 (incorporated herein as SEQ ID NO: 3), GENBANK Accession No. AK297672.1 (incorporated herein as SEQ ID NO: 4), GENBANK Accession No. DC413312.1 (incorporated herein as SEQ ID NO: 5), GENBANK Accession No. AV688858.2 (incorporated herein as SEQ ID NO: 6), GENBANK Accession No. CD652077.1 (incorporated herein as SEQ ID NO: 7), GENBANK Accession No. BC143911.1 (incorporated herein as SEQ ID NO: 8), GENBANK Accession No. CB162532.1 (incorporated herein as SEQ ID NO: 9), GENBANK Accession No. NT_016354.19 truncated from nucleobases 111693001 to 111730000 (incorporated herein as SEQ ID NO: 10), GENBANK Accession No. NM_008455.2 (incorporated herein as SEQ ID NO: 11), GENBANK Accession No. BB598673.1 (incorporated herein as SEQ ID NO: 12), the complement of GENBANK Accession No. NT_039460.7 truncated from nucleobases 6114001 to 6144000 (incorporated herein as SEQ ID NO: 13), GENBANK Accession No. NM_012725.2 (incorporated herein as SEQ ID NO: 14), GENBANK Accession No. NW_047473.1 truncated from nucleobases 10952001 to 10982000 (incorporated herein as SEQ ID NO: 15), exons 1-7 and 9-15 cut from the rhesus genomic sequence GENBANK Accession No. NW_001118167.1 based on similarity to human exons and where rhesus exon 8 has been replaced with N (110) (incorporated herein as SEQ ID NO: 16), GENBANK Accession No. XM_002804276.1 (incorporated herein as SEQ ID NO: 17), GENBANK Accession No. NW_001118167.1 truncated from nucleobases 2358000 to 2391000 (incorporated herein as SEQ ID NO: 18), and exons 1-15 assembled from trace archive of baboon based on homology to human (incorporated herein as SEQ ID NO: 19).

In certain embodiments, the compound of the invention may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19.

In certain embodiments, the compound of the invention may comprise a modified oligonucleotide comprising a nucleobase sequence at least 80%, at least 85%, at least 90%, at least 95%, at least 96%, at least 97%, at least 98%, or at least 99% complementary to an equal length portion of a human sequence. In certain embodiments, the compound of the invention may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In certain embodiments, the compound of the invention may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19.

In certain embodiments, the compound of the invention may comprise a modified oligonucleotide comprising a nucleobase sequence 100% complementary to an equal length portion of a human sequence. In certain embodiments, the compound of the invention may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In certain embodiments, the nucleobase sequence of the modified oligonucleotide is 100% complementary to a nucleobase sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

Certain embodiments provide methods comprising identifying an animal having a clotting disorder by administering to the animal a therapeutically effective amount of a compound comprising a modified oligonucleotide consisting of 12 to 30 linked nucleosides, wherein the modified oligonucleotide is complementary to a kallikrein nucleic acid.

Certain embodiments provide methods comprising reducing the risk for thromboembolic conditions in an animal by administering to the animal a therapeutically effective amount of a compound comprising a modified oligonucleotide consisting of 12 to 30 linked nucleosides, wherein the modified oligonucleotide is complementary to a kallikrein nucleic acid.

Certain embodiments provide methods comprising treating a clotting disorder in an animal by administering to the animal a therapeutically effective amount of a compound comprising a modified oligonucleotide consisting of 12 to 30 linked nucleosides, wherein the modified oligonucleotide is complementary to a kallikrein nucleic acid.

Certain embodiments provide methods comprising inhibiting kallikrein expression in an animal by administering to the animal a therapeutically effective amount of a compound comprising a modified oligonucleotide consisting of 12 to 30 linked nucleosides, wherein the modified oligonucleotide is complementary to a kallikrein nucleic acid.

In certain embodiments, the kallikrein inhibition in the animal is reversed by administering an antidote to the modified oligonucleotide.

In certain embodiments, the antidote is an oligonucleotide complementary to the modified oligonucleotide.

Certain embodiments provide for the use of a modified oligonucleotide consisting of 12 to 30 linked nucleosides, wherein the modified oligonucleotide is complementary to a kallikrein nucleic acid in the manufacture of a medicament for treating a thromboembolic condition.

Certain embodiments provide methods comprising of inhibiting Factor 12 activation by inhibiting KLKB1 mRNA expression with a kallikrein specific inhibitor.

In certain embodiments, the kallikrein specific inhibitor is an antisense compound.

In certain embodiments, the antisense compound is a modified oligonucleotide consisting of 12 to 30 linked nucleosides, wherein the modified oligonucleotide is at least 90% complementary to a kallikrein nucleic acid.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a kallikrein nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a kallikrein nucleic acid may be shortened or truncated. For example, a single subunit may be deleted from the 5' end (5' truncation), or alternatively from the 3' end (3' truncation). A shortened or truncated antisense compound targeted to a kallikrein nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a kallikrein nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a kallikrein nucleic acid possess a 5-10-5 gapmer motif.

In certain embodiments, antisense compounds targeted to a kallikrein nucleic acid possess a 3-14-3 gapmer motif.

In certain embodiments, antisense compounds targeted to a kallikrein nucleic acid possess a 2-13-5 gapmer motif.

In certain embodiments, antisense compounds targeted to a kallikrein nucleic acid possess a 5-8-5 gapmer motif.

In certain embodiments, antisense compounds targeted to a kallikrein nucleic acid possess a 6-8-6 gapmer motif.

In certain embodiments, an antisense compound targeted to a kallikrein nucleic acid has a gap-widened motif.

In certain embodiments, a gap-widened antisense oligonucleotide targeted to a kallikrein nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a kallikrein nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode kallikrein include, without limitation, the following: GENBANK Accession No. NM_000892.3 (incorporated herein as SEQ ID NO: 1), GENBANK Accession No. DC412984.1 (incorporated herein as SEQ ID NO: 2), GENBANK Accession No. CN265612.1 (incorporated herein as SEQ ID NO: 3), GENBANK Accession No. AK297672.1 (incorporated herein as SEQ ID NO: 4), GENBANK Accession No. DC413312.1 (incorporated herein as SEQ ID NO: 5), GENBANK Accession No. AV688858.2 (incorporated herein as SEQ ID NO: 6), GENBANK Accession No. CD652077.1 (incorporated herein as SEQ ID NO: 7), GENBANK Accession No. BC143911.1 (incorporated herein as SEQ ID NO: 8), GENBANK Accession No. CB162532.1 (incorporated herein as SEQ ID NO: 9), GENBANK Accession No. NT_016354.19 truncated from nucleobases 111693001 to 111730000 (incorporated herein as SEQ ID NO: 10), GENBANK Accession No. NM_008455.2 (incorporated herein as SEQ ID NO: 11), GENBANK Accession No. BB598673.1 (incorporated herein as SEQ ID NO: 12), the complement of GENBANK Accession No. NT 039460.7 truncated from nucleobases 6114001 to 6144000 (incorporated herein as SEQ ID NO: 13), GENBANK Accession No. NM_012725.2 (incorporated herein as SEQ ID NO: 14), GENBANK Accession No. NW_047473.1 truncated from nucleobases 10952001 to 10982000 (incorporated herein as SEQ ID NO: 15), exons 1-7 and 9-15 cut from the rhesus genomic sequence GENBANK Accession No. NW_001118167.1 based on similarity to human exons and where rhesus exon 8 has been replaced with N (110) (incorporated herein as SEQ ID NO: 16), GENBANK Accession No. XM_002804276.1 (incorporated herein as SEQ ID NO: 17), GENBANK Accession No. NW_001118167.1 truncated from nucleobases 2358000 to 2391000 (incorporated herein as SEQ ID NO: 18), and exons 1-15 assembled from trace archive of baboon based on homology to human (incorporated herein as SEQ ID NO: 19).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for kallikrein can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in kallikrein mRNA levels are indicative of inhibition of kallikrein expression. Reductions in levels of a kallikrein protein are also indicative of inhibition of target mRNA expression. Further, phenotypic changes are indicative of inhibition of kallikrein expression. For example, a prolonged aPTT time can be indicative of inhibition of kallikrein expression. In another example, prolonged aPTT time in conjunction with a normal PT time can be indicative of inhibition of kallikrein expression. In another example, a decreased quantity of Platelet Factor 4 (PF-4) can be indicative of inhibition of kallikrein expression. In another example, reduced formation of thrombus or increased time for thrombus formation can be indicative of inhibition of kallikrein expression.

Hybridization

In some embodiments, hybridization occurs between an antisense compound disclosed herein and a kallikrein nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a kallikrein nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a kallikrein nucleic acid).

Non-complementary nucleobases between an antisense compound and a kallikrein nucleic acid may be tolerated provided that the antisense compound remains able to specifically hybridize to a target nucleic acid. Moreover, an antisense compound may hybridize over one or more segments of a kallikrein nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a kallikrein nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof; are fully complementary (i.e. 100% complementary) to a target nucleic acid, or specified portion thereof. For example, an antisense compound may be fully complementary to a kallikrein nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a kallikrein nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a kallikrein nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a kallikrein nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_1)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' (also referred to as constrained ethyl of cEt) and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.*, 2009, 74, 118-134); and 4'-$CH_2$—C(═$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA, and (K) vinyl BNA, as depicted below.

(A)

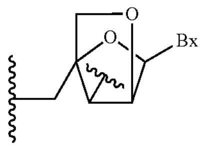

(B)

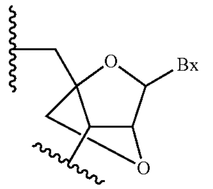

(C)

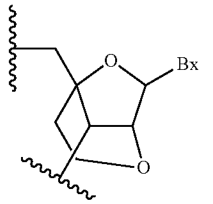

(D)

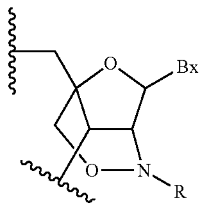

(E)

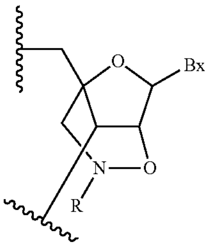

(F)

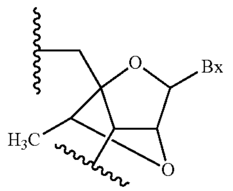

(G)

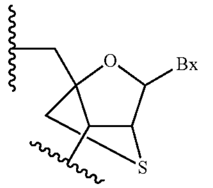

(H)

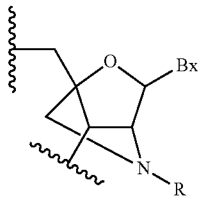

-continued (I)

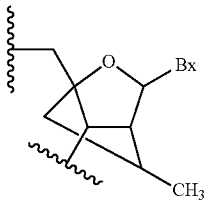

(J)

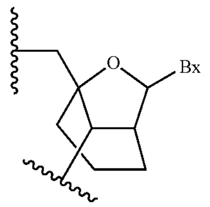

(K)

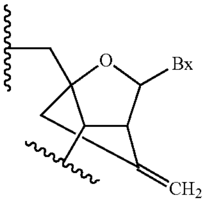

wherein Bx is the base moiety and R is independently H, a protecting group, $C_1$-$C_{12}$ alkyl, or $C_1$-$C_{12}$ alkoxy.

In certain embodiments, bicyclic nucleosides are provided having Formula I:

I

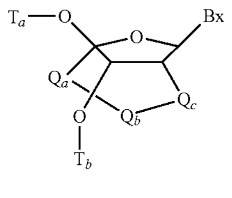

wherein:

Bx is a heterocyclic base moiety;

-$Q_a$-$Q_b$-$Q_c$- is —$CH_2$—$N(R_c)$—$CH_2$—, —C(=O)—N($R_c$)—$CH_2$—, —$CH_2$—O—$N(R_c)$—, —$CH_2$—$N(R_c)$—O— or —$N(R_c)$—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

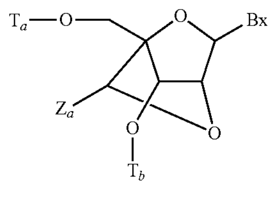

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

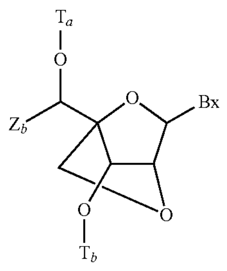

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

IV

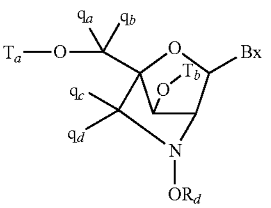

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

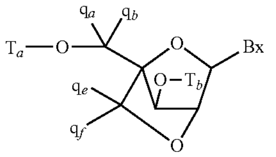

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

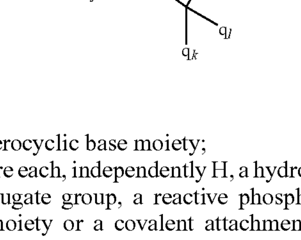

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C$(=O)N(H)$CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), or fluoro HNA (F-HNA) having a tetrahydropyran ring system, as illustrated below:

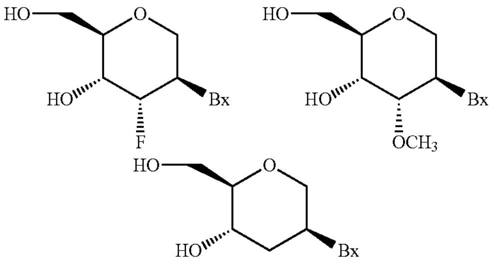

In certain embodiments, sugar surrogates are selected having Formula VII:

VII

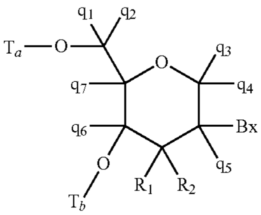

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry,* 2002, 41, 4503-4510; and U.S. Pat. Nos. 5,698,685; 5,166,315; 5,185,444; and 5,034,506). As used here, the term "morpholino" means a sugar surrogate having the following formula:

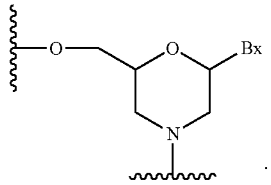

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.,* 2008, 130(6), 1979-1984; Horvath et al., *Tetrahedron Letters,* 2007, 48, 3621-3623; Nauwelaerts et al., *J. Am. Chem. Soc.,* 2007, 129(30), 9340-9348; Gu et al., *Nucleosides, Nucleotides & Nucleic Acids,* 2005, 24(5-7), 993-998; Nauwelaerts et al., *Nucleic Acids Research,* 2005, 33(8), 2452-2463; Robeyns et al., *Acta Crystallographica, Section F: Structural Biology and Crystallization Communications,* 2005, F61(6), 585-586; Gu et al., *Tetrahedron,* 2004, 60(9), 2111-2123; Gu et al., *Oligonucleotides,* 2003, 13(6), 479-489; Wang et al., *J. Org. Chem.,* 2003, 68, 4499-4505; Verbeure et al., *Nucleic Acids Research,* 2001, 29(24), 4941-4947; Wang et al., *J. Org. Chem.,* 2001, 66, 8478-82; Wang et al., *Nucleosides, Nucleotides & Nucleic Acids,* 2001, 20(4-7), 785-788; Wang et al., *J. Am. Chem.,* 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

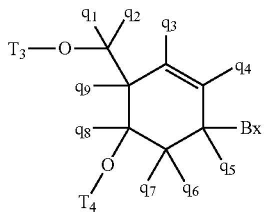

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a Factor VII nucleic acid comprise one or more modified nucleobases. In certain embodiments, gap-widened antisense oligonucleotides targeted to a Factor VII nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a kallikrein nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a kallikrein nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

In certain embodiments, one or more modified oligonucleotides of the present invention can be formulated as a prodrug. A prodrug can be produced by modifying a pharmaceutically active compound such that the active compound will be regenerated upon in vivo administration. For example, a prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of kallikrein nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a kallikrein nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Kallikrein nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of kallikrein nucleic acids can be assessed by measuring kallikrein protein levels. Protein levels of kallikrein can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human kallikrein are commercially available.

In Vivo Testing of Antisense Compounds

Antisense compounds, for example, antisense oligonucleotides, are tested in animals to assess their ability to inhibit expression of kallikrein and produce phenotypic changes, such as, prolonged aPTT, prolonged aPTT time in conjunction with a normal PT, decreased quantity of Platelet Factor 4 (PF-4), and reduced formation of thrombus or increased time for thrombus formation. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in kallikrein nucleic acid expression are measured. Changes in kallikrein protein levels are also measured using a thrombin generation assay. In addition, effects on clot times, e.g. PT and aPTT, are determined using plasma from treated animals.

Certain Indications

In certain embodiments, the invention provides methods of treating an individual comprising administering one or more pharmaceutical compositions as described herein. In certain embodiments, the individual has a thromboembolic condition. In certain embodiments, the individual is at risk for a blood clotting disorder, including, but not limited to, infarct, thrombosis, embolism, thromboembolism such as deep vein thrombosis, pulmonary embolism, myocardial infarction, and stroke. This includes individuals with an acquired problem, disease, or disorder that leads to a risk of thrombosis, for example, surgery, cancer, immobility, sepsis, atherosclerosis atrial fibrillation, as well as genetic predisposition, for example, antiphospholipid syndrome and the autosomal dominant condition, Factor V Leiden. In certain embodiments, the individual has been identified as in need of anticoagulation therapy. Examples of such individuals include, but are not limited to, those undergoing major orthopedic surgery (e.g., hip/knee replacement or hip fracture surgery) and patients in need of chronic treatment, such as those suffering from arterial fibrillation to prevent stroke. In certain embodiments the invention provides methods for prophylactically reducing kallikrein expression in an individual. Certain embodiments include treating an individual in need thereof by administering to an individual a therapeutically effective amount of an antisense compound targeted to a kallikrein nucleic acid.

In one embodiment, administration of a therapeutically effective amount of an antisense compound targeted to a kallikrein nucleic acid is accompanied by monitoring of kallikrein levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a kallikrein nucleic acid results in reduction of kallikrein expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a kallikrein nucleic acid results in a change in a measure of blood clotting as measured by a standard test, for example, but not limited to, activated partial thromboplastin time (aPTT) test, prothrombin time (PT) test, thrombin time (TCT), bleeding time, or D-dimer. In certain embodiments, administration of a kallikrein antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a kallikrein antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to kallikrein are used for the preparation of a medicament for treating a patient suffering or susceptible to a thromboembolic condition.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions. In certain embodiments, such one or more other pharmaceutical agents are designed to treat a different disease, disorder, or condition as the one or more pharmaceutical compositions. In certain embodiments, such one or more other pharmaceutical agents are designed to treat an undesired side effect of one or more pharmaceutical compositions. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition include anticoagulant or antiplatelet agents. In certain embodiments, pharmaceutical agents that may be co-administered with a pharmaceutical composition include NSAID/Cyclooxygenase inhibitors, such as, aspirin. In certain embodiments, pharmaceutical agents that may be co-administered with a pharmaceutical composition include adenosine diphosphate (ADP) receptor inhibitors, such as, clopidogrel (PLAVIX) and ticlopidine (TICLID). In certain embodiments, pharmaceutical agents that may be co-administered with a pharmaceutical composition include phosphodiesterase inhibitors, such as, cilostazol (PLETAL). In certain embodiments, pharmaceutical agents that may be co-administered with a pharmaceutical composition include, glycoprotein IIB/IIIA inhibitors, such as, abciximab (REOPRO), eptifibatide (INTEGRILIN), tirofiban (AGGRASTAT), and defibrotide. In certain embodiments, pharmaceutical agents that may be co-administered with a pharmaceutical composition include, adenosine reuptake inhibitors, such as, to dipyridamole (PERSANTINE). In certain embodiments, pharmaceutical agents that may be co-administered with a pharmaceutical composition include, but are not limited to warfarin (and related coumarins), heparin, direct thrombin inhibitors (such as lepirudin, bivalirudin), apixaban, LOVENOX, and small molecular compounds that interfere directly with the enzymatic action of particular coagulation factors (e.g. rivaroxaban, which interferes with Factor Xa). In certain embodiments, pharmaceutical agents that may be co-administered with a kallikrein specific inhibitor include, but are not limited to, an additional kallikrein inhibitor. In certain embodiments, the anticoagulant or antiplatelet agent is administered prior to administration of a pharmaceutical composition. In certain embodiments, the anticoagulant or antiplatelet agent is administered following administration of a pharmaceutical composition. In certain embodiments the anticoagulant or antiplatelet agent is administered at the same time as a pharmaceutical composition. In certain embodiments the dose of a co-administered anticoagulant or antiplatelet agent is the same as the dose that would be administered if the anticoagulant or antiplatelet agent was administered alone. In certain embodiments the dose of a co-administered anticoagulant or antiplatelet agent is lower than the dose that would be administered if the anticoagulant or antiplatelet agent was administered alone. In certain embodiments the dose of a co-administered anticoagulant or antiplatelet agent is greater than the dose that would be administered if the anticoagulant or antiplatelet agent was administered alone.

In certain embodiments, the co-administration of a second compound enhances the anticoagulant effect of a first compound, such that co-administration of the compounds results in an anticoagulant effect that is greater than the effect of administering the first compound alone. In other embodiments, the co-administration results in anticoagulant effects that are additive of the effects of the compounds when administered alone. In certain embodiments, the co-administration results in anticoagulant effects that are supra-additive of the effects of the compounds when administered alone. In certain embodiments, the co-administration of a second compound increases antithrombotic activity without increased bleeding risk. In certain embodiments, the first compound is an antisense compound. In certain embodiments, the second compound is an antisense compound.

In certain embodiments, an antidote is administered anytime after the administration of a kallikrein specific inhibitor. In certain embodiments, an antidote is administered anytime after the administration of an antisense oligonucleotide targeting kallikrein. In certain embodiments, the antidote is administered minutes, hours, days, weeks, or months after the administration of an antisense compound targeting kallikrein. In certain embodiments, the antidote is a complementary (e.g. the sense strand) to the antisense compound targeting kallikrein. In certain embodiments, the antidote is a Factor 7 or Factor 7a protein. In certain embodiments, the Factor 7 or Factor 7a protein is a human Factor 7 or human Factor 7a protein. In certain embodiments, the Factor 7 protein is NOVOSEVEN.

Certain Co-Administered Antiplatelet Therapies

In certain embodiments, kallikrein inhibitors are combined with antiplatelet therapies. In certain embodiments, administration of a kallikrein inhibitor in combination with an antiplatelet therapy results in little to no appreciable or detectable increase in risk of bleeding as compared to antiplatelet therapy alone. In certain embodiments, the risk profile or risk indications are unchanged over antiplatelet therapy alone.

The combination of antiplatelet and anticoagulant therapy is used in clinical practice most frequently in patients diagnosed with, for example, thromboembolism, atrial fibrillation, a heart valve disorder, valvular heart disease, stroke, CAD, and in patients having a mechanical valve. The benefit of dual therapy relates to the probable additive effect of suppressing both platelet and coagulation factor activities. The risk of dual therapy is the potential for increased bleeding (Dowd, M. Plenary Sessions/Thrombosis Research 123 (2008)).

Prior combinations of antiplatelet and anticoagulant therapy have been shown to increase the risk of bleeding compared with anticoagulant or antiplatelet therapy alone. Such combinations include, FXa inhibitors (e.g., apixiban and rivaroxaban) with ADP receptor/P2Y12 inhibitors (Thienopyridines such as clopidogrel—also known as PLAVIX) and NSAIDs (e.g., aspirin and naproxen) (Kubitza, D. et al., *Br. J. Clin. Pharmacol.* 63:4 (2006); Wong, P. C. et al. *Journal of Thrombosis and Haemostasis* 6 (2008); FDA Advisory Committee Briefing Document for New Drug Application 22-406 (2009)). For example, Wong reports that addition of certain doses of apixaban to aspirin and to aspirin plus clopidogrel produced a significant increase in bleeding time compared with aspirin alone and aspirin plus clopidogrel. Kubitza reports that the combination administration of rivaroxaban and naproxen significantly increased bleeding time over naproxen alone.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Murine Kallikrein mRNA in Mouse Primary Hepatocytes

Antisense oligonucleotides targeting a murine kallikrein (KLKB1) nucleic acid were designed and tested for their effects on kallikrein mRNA in vitro. Cultured mouse primary hepatocytes at a density of 10,000 cells per well were transfected using Cytofectin reagent with 12.5 nM, 25.0 nM, 50.0 nM, 100.0 nM, and 200.0 nM of antisense oligonucleotide. After a treatment period of approximately 24 hours, RNA was isolated from the cells and mouse kallikrein mRNA levels were measured by quantitative real-time PCR using the murine primer probe set RTS3313 (forward sequence TGCCTGCTGTTCAGCTTTCTC, designated herein as SEQ ID NO: 20; reverse sequence TGGCAAAGTCCCTGTAATGCT, designated herein as SEQ ID NO: 21; probe sequence CGTGACTCCACCCAAAGAGACAAATAAACG, designated herein as SEQ ID NO: 22). Kallikrein mRNA levels were adjusted according to total RNA content, as measured by RIBOGREEN.

The chimeric antisense oligonucleotides were designed as 5-10-5 MOE gapmers. The gapmers are 20 nucleotides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. Results demonstrate that kallikrein mRNA levels were significantly reduced in a dose dependent manner.

In one specific example, ISIS 482584 (GGCATATTGGTTTTTGGAAT; SEQ ID NO: 32) reduced kallikrein mRNA in a dose dependent manner yielding a half maximal inhibitory concentration ($IC_{50}$) of 84 nM (see Table 1). ISIS 482584 is targeted to SEQ ID NO: 11 (GENBANK Accession No. NM_008455.2) and has a target start site of 1586 and a target stop site of 1605. "Target start site" indicates the 5'-most nucleotide to which the gapmer is targeted. "Target stop site" indicates the 3'-most nucleotide to which the gapmer is targeted.

TABLE 1

Dose-dependent inhibition of mouse KLKB1 mRNA levels by ISIS 482584

| Dose | % inhibition |
|---|---|
| 12.5 nM | 0 |
| 25.0 nM | 47 |
| 50.0 nM | 27 |
| 100.0 nM | 60 |
| 200.0 nM | 82 |

Example 2

Antisense Inhibition of Kallikrein mRNA in Rat Primary Hepatocytes

ISIS 482584 was also tested for its effect on rat kallikrein (KLKB1) mRNA in vitro. Cultured rat primary hepatocytes at a density of 20,000 cells per well were transfected using Cytofectin reagent with 200 nM of antisense oligonucleotide. After a treatment period of approximately 24 hours, RNA was isolated from the cells and rat kallikrein mRNA levels were measured by quantitative real-time PCR using the murine primer probe set RTS3315 (forward sequence TCGGTTGCCCCATGGAT, designated herein as SEQ ID NO:23; reverse sequence GGTGACGACATGGCTTACATTC, designated herein as SEQ ID NO: 24; probe sequence TTTTCCAGCACTTTGCCTTTGCAGACC, designated herein as SEQ ID NO: 25). Kallikrein mRNA levels were adjusted according to total RNA content, as measured by RIBOGREEN.

Results demonstrated that ISIS 482584 reduced kallikrein mRNA in rat primary hepatocytes by 82%.

Example 3

Antisense Inhibition of Kallikrein mRNA In Vivo

ISIS 482584 was tested for its affect on murine kallikrein (KLKB1) mRNA in vivo.

Treatment

Six groups of male BALB/c mice each were treated with 2.5 mg/kg, 5.0 mg/kg, 10.0 mg/kg, 20.0 mg/kg, 40.0 mg/kg, or 80.0 mg/kg of ISIS 482584, administered subcutaneously twice a week for 3 weeks (weekly doses of 5.0 mg/kg, 10.0 mg/kg, 20.0 mg/kg, 40.0 mg/kg, 80.0 mg/kg, or 160.0 mg/kg). A control group of BALB/c mice was treated with PBS, administered subcutaneously twice a week for 3 weeks. Two days after the last dose of antisense oligonucleotide or PBS, mice from all groups were anesthetized with 150 mg/kg ketamine mixed with 10 mg/kg xylazine, administered by intraperitoneal injection. Liver was collected for RNA analysis.

RNA Analysis

RNA was extracted from liver tissue for real-time PCR analysis of kallikrein. Kallikrein mRNA levels were measured using the murine primer probe set (forward sequence ACAAGTGCATTTTACAGACCAGAGTAC, designated herein as SEQ ID NO: 26; reverse sequence GGTTGTCCGCTGACTTTATGCT, designated herein as SEQ ID NO: 27; probe sequence AAGCACAGTGCAAGCGGAACACCC, designated herein as SEQ ID NO: 28). Results are presented as percent inhibition of kallikrein, relative to PBS control. As shown in Table 2, treatment with ISIS 482584 resulted in significant dose-dependent reduction of kallikrein mRNA in comparison to the PBS control.

TABLE 2

Dose-dependent reduction of kallikrein mRNA in BALB/c mice liver

| Dose (mg/kg/wk) | % inhibition |
|---|---|
| 5 | 3 |
| 10 | 42 |
| 20 | 68 |
| 40 | 85 |
| 80 | 91 |
| 160 | 94 |

Protein Analysis

Plasma was collected in tubes containing sodium citrate as an anticoagulant. The samples were run on a 4-12% gradient SDS-polyacrylamide gel (Invitrogen), followed by immunoblotting with murine PKK antibody (R&D Systems). Blots were incubated with secondary fluorophore-labeled antibodies (LI-COR) and imaged in an Odyssey Imager (LI-COR). Results are presented as percent inhibition of kallikrein, relative to PBS control. As shown in Table 3, treatment with ISIS 482584 resulted in significant dose-dependent reduction of kallikrein plasma protein in comparison to the PBS control.

TABLE 3

Dose-dependent reduction of kallikrein protein in BALB/c mice plasma

| Dose (mg/kg/wk) | % inhibition |
|---|---|
| 5 | 5 |
| 10 | 24 |
| 20 | 47 |
| 40 | 76 |
| 80 | 81 |
| 160 | n.d. |

n.d. = no data

Example 4

In Vivo Effect of Antisense Inhibition of Murine Kallikrein in the $FeCl_3$-Induced Inferior Vena Cava Thrombosis Model ISIS 482584, which demonstrated significant in vitro and in vivo inhibition of kallikrein (KLKB1), was evaluated in the $FeCl_3$-induced inferior vena cava thrombosis mouse model.

Treatment

Three groups of 8 male BALB/c mice were treated with 10 mg/kg, 20 mg/kg, or 40 mg/kg of ISIS 482584, administered subcutaneously twice a week for 3 weeks (weekly doses of 20 mg/kg, 40 mg/kg, or 80 mg/kg). Two control groups of 12 BALB/c mice each were treated with PBS, administered subcutaneously twice a week for 3 weeks. Two days after the last dose of antisense oligonucleotide or PBS, mice from all groups were anesthetized with 150 mg/kg ketamine mixed with 10 mg/kg xylazine, administered by intraperitoneal injection. Thrombus formation was induced with $FeCl_3$ in all groups of anesthetized mice except the first control group.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

Quantification of Platelet Composition

Real-time PCR quantification of platelet factor-4 (PF-4) was used to quantify platelets in the vena cava as a measure of thrombus formation. PF-4 mRNA levels were measured using the murine primer probe set mPF4_LTS_00086 (forward sequence AGACCCATTTCCTCAAGGTAGAACT, designated herein as SEQ ID NO: 29; reverse sequence CGCAGCGACGCTCATG, designated herein as SEQ ID NO: 30; probe sequence TCTTTGGGTCCAGTGGCACCCTCTT, designated herein as SEQ ID NO: 31). Results are presented as a percentage of PF-4 in ISIS oligonucleotide-treated mice, as compared to the two PBS-treated control groups. As shown in Table 4, treatment with ISIS 482584 resulted in a significant reduction of PF-4 in comparison to the PBS control. Therefore, reduction of kallikrein by the compound provided herein is useful for inhibiting thrombus formation.

TABLE 4

Analysis of thrombus formation by real-time PCR quantification of PF-4 in the $FeCl_3$ induced venous thrombosis model

| | Dose in mg/kg/wk | PF-4 |
|---|---|---|
| PBS − $FeCl_3$ | — | 0 |
| PBS + $FeCl_3$ | — | 100 |
| ISIS 482584 | 20 | 62 |
| | 40 | 34 |
| | 80 | 25 |

Example 5

In Vivo Effect of Antisense Inhibition of Murine Kallikrein in a Tail Bleeding Assay Tail-bleeding was measured to observe whether treatment with ISIS 482584 causes excess bleeding or hemorrhage in mice.

Treatment

Groups of 10 male BALB/c mice were treated with 10 mg/kg, 20 mg/kg, or 40 mg/kg of ISIS 482584, administered subcutaneously twice a week for 3 weeks (weekly doses of 20 mg/kg, 40 mg/kg, or 80 mg/kg). A control group of 8 BALB/c mice was treated with PBS, administered subcutaneously twice a week for 3 weeks.

Tail-Bleeding Assay

Two days after the final treatment of ISIS oligonucleotides or PBS, mice were placed in a tail bleeding chamber. Mice were anesthetized in the chamber with isoflurane. Then, a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding. The results are provided in Table 5.

Treatment with ISIS 482584 did not significantly affect bleeding. These data suggest that the hemorrhagic potential of the compounds provided herein is low. These data taken with the results provided in Example 4 suggest inhibition of kallikrein with the compounds described herein are useful for providing antithrombotic activity without associated bleeding risk.

TABLE 5

Tail bleeding assay after treatment with ISIS 482584

| | Dose (mg/kg/wk) | Bleeding (mL) |
|---|---|---|
| PBS | — | 0.03 |
| ISIS | 20 | 0.03 |
| 482584 | 40 | 0.14 |
| | 80 | 0.07 |

Example 6

In Vivo Effect of Antisense Inhibition of Murine Kallikrein in the $FeCl_3$ Induced Mesenteric Thrombosis Model ISIS 482584 was evaluated in the $FeCl_3$ induced mesenteric thrombosis mouse model.

Treatment

A group of 6-8 Swiss-Webster mice was treated with 40 mg/kg of ISIS 482584, administered subcutaneously twice a week for 3 weeks (weekly dose of 80 mg/kg). A control group of 6 Swiss-Webster mice was treated with PBS, administered subcutaneously twice a week for 3 weeks. Two days after the last dose of antisense oligonucleotide or PBS, mice from all groups were anesthetized with 75 mg/kg ketamine mixed with 25 mg/kg xylazine, administered by subcutaneous injection.

Rhodamine 6G dye at a dosage of 5 mg/kg was injected subcutaneously to stain platelets. Alexa-647-labeled anti-fibrinogen antibody at a dosage of 1 mg/kg was injected via tail vein injection to stain fibrin. The abdomen was opened by a middle incision. The visceral mesentery was spread on a glass coverslip and the mesenteric arterioles (70-120 μm) were located by observation under a microscope. Thrombus formation was induced by applying of cotton threads (2×0.3 mm) pre-saturated with 6% $FeCl_3$ solution directly on the target vessel. After three minutes of exposure, the thread was removed and the color intensities of both the dyes were recorded by fluorescent microscopy (Olympus FluoView 1000 confocal laser scanning microscope) with appropriate filters for 70 min.

The results for platelet aggregation in the control and treatment groups are presented in Table 6, expressed in arbitrary units (a.u.). Platelet aggregation was reduced in mice treated with ISIS 482584 at a dose of 80 mg/kg/week as compared to mice treated with PBS. The results for fibrin formation in the control and treatment groups are presented in Table 7, also expressed in arbitrary units (a.u.). Fibrin formation was reduced in mice treated with ISIS 482584 at a dose of 80 mg/kg/week as compared to mice treated with PBS. Therefore, these results suggest that ISIS 482584 inhibits thrombus formation.

TABLE 6

Analysis of platelet aggregation by real-time measurement of fluorescent intensity (a.u.) in a $FeCl_3$ induced mesenteric thrombus model

| Time (sec) | PBS | 80 mg/kg/wk |
|---|---|---|
| 752 | 54 | 74 |
| 1018 | 315 | 11 |
| 1284 | 485 | 7 |
| 1550 | 654 | 0 |
| 1815 | 1079 | 0 |
| 2081 | 1164 | 0 |
| 2347 | 1452 | 0 |
| 2613 | 1440 | 38 |
| 2879 | 1689 | 148 |
| 3144 | 1716 | 129 |
| 3410 | 1845 | 169 |
| 3676 | 1865 | 131 |
| 3944 | 2055 | 87 |

TABLE 7

Analysis of fibrin formation by real-time measurement of fluorescent intensity (a.u.) in a $FeCl_3$ induced mesenteric thrombus model

| Time (sec) | PBS | 80 mg/kg/wk |
|---|---|---|
| 752 | 9 | 54 |
| 1018 | 86 | 7 |
| 1284 | 203 | 1 |
| 1550 | 319 | 10 |
| 1815 | 521 | 16 |
| 2081 | 598 | 15 |
| 2347 | 831 | 61 |
| 2613 | 959 | 88 |
| 2879 | 1157 | 141 |
| 3144 | 1236 | 150 |
| 3410 | 1374 | 173 |
| 3676 | 1629 | 160 |
| 3944 | 1822 | 128 |

Example 7

In Vivo Effect of Antisense Inhibition of Murine Kallikrein in the Stenosis-Induced Inferior Vena Cava Thrombosis Model ISIS 482584 was evaluated in the stenosis-induced inferior vena cava (IVC) thrombosis model. Reduced blood flow and endothelial damage are hallmarks of this model, also known as the St. Tomas model.

Treatment

Four groups of 6-8 BALB/c mice were treated with 5 mg/kg, 10 mg/kg, 20 mg/kg, or 40 mg/kg of ISIS 482584, administered subcutaneously twice a week for 3 weeks (weekly doses of 10 mg/kg, 20 mg/kg, 40 mg/kg, or 80 mg/kg). A control group of 8 BALB/c mice was treated with PBS, administered subcutaneously twice a week for 3 weeks. Two days after the last dose of antisense oligonucleotide or PBS was administered, mice from all groups were anesthetized with 2.5% inhalant isoflurane. The IVC of the mice was exposed via a midline abdominal incision below the left renal vein, and was separated from the abdominal aorta by blunt dissection. A 6-0 silk tie (Ethicon, UK) was placed behind the blood vessel just below the left renal vein and a metal 4-0 suture (Ethicon, UK) was placed longitudinally over the IVC to tie the silk tie on top. The metal suture was then removed. Two neurovascular surgical clips (Braun Medical Inc, PA) were placed at two separate positions below the ligation for 20 seconds each, after which they were removed. The abdominal cavity contents were then replaced and the abdomen was closed. After 24 hrs, the IVC was exposed and checked for thrombi formation. All thrombi formed were collected and fixed in 10% formalin for 24 hrs.

The thrombi were weighed and the results are presented in Table 8, expressed in milligrams. As demonstrated by the results, treatment with increasing doses of ISIS 482584 resulted in corresponding decrease in thrombus weight. The results indicate that antisense inhibition of kallikrein is useful for inhibiting thrombus formation.

TABLE 8

Thrombi weights in the stenosis-induced IVC thrombosis model

| | Dose in mg/kg/wk | Weight (mg) |
|---|---|---|
| PBS | — | 10 |
| ISIS 482584 | 10 | 8 |
| | 20 | 6 |
| | 40 | 5 |
| | 80 | 3 |

Example 8

Inhibition of Factor 12 Protein Activation by ISIS 482584

The effect of antisense inhibition of kallikrein mRNA on Factor 12 protein activation was evaluated.

Treatment

The various treatment groups for this assay are presented in Table 9.

Group 1 consisted of 8 mice and was treated with PBS administered subcutaneously twice a week for 3 weeks. No other treatment was administered to Group 1 which served as a control group to measure Factor 12 activation.

Groups 2, 3, 4, 5, and 6 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively of ISIS 482584 administered subcutaneously twice a week for 3 weeks. Groups 2-6 served as the treatment groups for measuring the effect of ISIS 482584 on Factor 12 activation.

At the end of the treatment period, plasma was harvested from the mice for the Spectrozyme® Factor 12a based amidolytic assay for Factor 12 in plasma.

TABLE 9

Treatment groups

| Group No. | Treatment | Dose (mg/kg/wk) |
|---|---|---|
| 1. (N = 8) | PBS | — |
| 2. (N = 8) | ISIS 482584 | 80 |
| 3. (N = 8) | ISIS 482584 | 40 |
| 4. (N = 8) | ISIS 482584 | 20 |
| 5. (N = 8) | ISIS 482584 | 10 |
| 6. (N = 8) | ISIS 482584 | 5 |

Assay for Factor 12 Activation in Plasma

Plasma (5 μL) was added to 85 μL of PBS with 1 μg/ml dextran sulfate (500 kDa) in a 96 well polypropelene microplate and the solution was incubated for 5 minutes at room temperature. Spectrozyme® FXIIa (10 μL of a 2 mM solution) and 0.2 mM KALLISTOP™ solution was added and the absorbance kinetic was measured at 405 nm. Factor 12 activation was measured in the linear phase of absorbance accumulation. The results are presented in Table 10 as a percentage of Factor 12 activation measured in the PBS control sample. As observed in Table 10, inhibition of kallikrein by ISIS 482584 results in decreased activation of Factor 12 by its substrate, implying the that PKK is required for proper factor 12 activation.

TABLE 10

Percentage Factor 12 activation compared to the PBS control

| Dose (mg/kg/wk) | % F12 activation |
|---|---|
| 80 | 14 |
| 40 | 24 |
| 20 | 47 |
| 10 | 63 |
| 5 | 82 |

What is claimed is:

1. A method comprising, administering to an animal having a thromboembolic condition or at risk for developing a thromboembolic condition a therapeutically effective amount of a compound comprising a modified oligonucleotide consisting of 12 to 30 linked nucleosides, wherein the modified oligonucleotide has a nucleobase sequence that is at least 90% complementary to a KLKB1 nucleic acid.

2. The method of claim 1, wherein the KLKB1 nucleic acid is any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

3. The method of claim 1, wherein the animal is a human.

4. The method of claim 1, wherein the administering inhibits thrombus and clot formation.

5. The method claim 1, wherein the administering of prolongs aPTT.

6. The method of claim 1, wherein the administering does not prolong PT.

7. The method of claim 1, wherein the administering prolongs aPTT and does not prolong PT.

8. The method of claim 1, wherein the administering decreases Platelet Factor 4 (PF-4).

9. The method of claim 1, wherein the administering increases time for thrombus formation.

10. The method of claim 1, wherein the administering reduces platelet aggregation.

11. The method of claim 1, wherein the administering reduces fibrin formation.

12. The method of claim 1, wherein the administering does not increase bleeding in the at risk animal as compared to an animal not administered with a modified oligonucleotide.

13. The method of claim 1, wherein the thromboembolic condition is any of the group consisting of thrombosis, embolism, thromboembolism, deep vein thrombosis, pulmonary embolism, myocardial infarction, stroke, or a combination thereof.

14. The method of claim 1, comprising co-administering any of the group selected from warfarin, apixaban, LOVENOX, aspirin, clopidogrel, dipyridamole, heparin, lepirudin, ticlopidine, rivaroxaban, anti-platelet therapy, or a combination thereof.

15. The method of claim 1, comprising concomitantly administering any of the group selected from warfarin, apixaban, LOVENOX, aspirin, clopidogrel, dipyridamole, heparin, lepirudin, ticlopidine, rivaroxaban, anti-platelet therapy, or a combination thereof.

16. The method of claim 1, wherein the compound is a single-stranded oligonucleotide.

17. The method of claim 1, wherein the modified oligonucleotide comprises at least one modified internucleoside linkage.

18. The method of claim 17, wherein the modified internucleoside linkage is a phosphorothioate internucleoside linkage.

19. The method of claim 1, wherein the modified oligonucleotide comprises at least one modified sugar.

20. The method of claim 19, wherein the modified sugar is a bicyclic sugar.

21. The method of claim 20, wherein the bicyclic sugar comprises a 4'-CH($CH_3$)—O-2' bridge, a 4'-($CH_2$)—O-2' bridge, or a 4'-$(CH_2)_2$—O-2' bridge.

22. The method of claim 19, wherein the modified sugar comprises a 2'-O-methoxyethyl group.

23. The method of any of claims 1, wherein at least one nucleoside comprises a modified nucleobase.

24. The method of claim 23, wherein the modified nucleobase is a 5-methylcytosine.

25. The method of claim 1, wherein the modified oligonucleotide is a gapmer.

26. The method of claim 1, wherein the oligonucleotide comprises:

a gap segment consisting of linked deoxy nucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

27. The method of claim 26, wherein the oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine in the oligonucleotide is a 5-methylcytosine, and wherein each internucleoside linkage of the oligonucleotide is a phosphorothioate linkage.

28. The method of claim 27, wherein the oligonucleotide consists of 20 linked nucleosides.

29. The method of claim 1, wherein the compound comprises a conjugate.

30. The method of claim 1, wherein the modified oligonucleotide has a nucleobase sequence that is 100% complementary to a human KLKB1 nucleic acid.

* * * * *

SEQUENCE LISTING

```
<160> NUMBER OF SEQ ID NOS: 32

<210> SEQ ID NO 1
<211> LENGTH: 2252
<212> TYPE: DNA
<213> ORGANISM: Homo sapiens
<220> FEATURE:
<221> NAME/KEY: CDS
<222> LOCATION: (72)..(1988)

<400> SEQUENCE: 1

agaacagctt gaagaccgtt catttttaag tgacaagaga ctcacctcca agaagcaatt      60

gtgttttcag a atg att tta ttc aag caa gca act tat ttc att tcc ttg      110
             Met Ile Leu Phe Lys Gln Ala Thr Tyr Phe Ile Ser Leu
             1               5                   10

ttt gct aca gtt tcc tgt gga tgt ctg act caa ctc tat gaa aac gcc      158
Phe Ala Thr Val Ser Cys Gly Cys Leu Thr Gln Leu Tyr Glu Asn Ala
    15                  20                  25
```

-continued

```
ttc ttc aga ggt ggg gat gta gct tcc atg tac acc cca aat gcc caa      206
Phe Phe Arg Gly Gly Asp Val Ala Ser Met Tyr Thr Pro Asn Ala Gln
30                  35                  40                  45

tac tgc cag atg agg tgc aca ttc cac cca agg tgt ttg cta ttc agt      254
Tyr Cys Gln Met Arg Cys Thr Phe His Pro Arg Cys Leu Leu Phe Ser
                50                  55                  60

ttt ctt cca gca agt tca atc aat gac atg gag aaa agg ttt ggt tgc      302
Phe Leu Pro Ala Ser Ser Ile Asn Asp Met Glu Lys Arg Phe Gly Cys
            65                  70                  75

ttc ttg aaa gat agt gtt aca gga acc ctg cca aaa gta cat cga aca      350
Phe Leu Lys Asp Ser Val Thr Gly Thr Leu Pro Lys Val His Arg Thr
        80                  85                  90

ggt gca gtt tct gga cat tcc ttg aag caa tgt ggt cat caa ata agt      398
Gly Ala Val Ser Gly His Ser Leu Lys Gln Cys Gly His Gln Ile Ser
    95                  100                 105

gct tgc cat cga gac att tat aaa gga gtt gat atg aga gga gtc aat      446
Ala Cys His Arg Asp Ile Tyr Lys Gly Val Asp Met Arg Gly Val Asn
110                 115                 120                 125

ttt aat gtg tct aag gtt agc agt gtt gaa gaa tgc caa aaa agg tgc      494
Phe Asn Val Ser Lys Val Ser Ser Val Glu Glu Cys Gln Lys Arg Cys
                130                 135                 140

acc agt aac att cgc tgc cag ttt ttt tca tat gcc acg caa aca ttt      542
Thr Ser Asn Ile Arg Cys Gln Phe Phe Ser Tyr Ala Thr Gln Thr Phe
            145                 150                 155

cac aag gca gag tac cgg aac aat tgc cta tta aag tac agt ccc gga      590
His Lys Ala Glu Tyr Arg Asn Asn Cys Leu Leu Lys Tyr Ser Pro Gly
        160                 165                 170

gga aca cct acc gct ata aag gtg ctg agt aac gtg gaa tct gga ttc      638
Gly Thr Pro Thr Ala Ile Lys Val Leu Ser Asn Val Glu Ser Gly Phe
    175                 180                 185

tca ctg aag ccc tgt gcc ctt tca gaa att ggt tgc cac atg aac atc      686
Ser Leu Lys Pro Cys Ala Leu Ser Glu Ile Gly Cys His Met Asn Ile
190                 195                 200                 205

ttc cag cat ctt gcg ttc tca gat gtg gat gtt gcc agg gtt ctc act      734
Phe Gln His Leu Ala Phe Ser Asp Val Asp Val Ala Arg Val Leu Thr
                210                 215                 220

cca gat gct ttt gtg tgt cgg acc atc tgc acc tat cac ccc aac tgc      782
Pro Asp Ala Phe Val Cys Arg Thr Ile Cys Thr Tyr His Pro Asn Cys
            225                 230                 235

ctc ttc ttt aca ttc tat aca aat gta tgg aaa atc gag tca caa aga      830
Leu Phe Phe Thr Phe Tyr Thr Asn Val Trp Lys Ile Glu Ser Gln Arg
        240                 245                 250

aat gtt tgt ctt ctt aaa aca tct gaa agt ggc aca cca agt tcc tct      878
Asn Val Cys Leu Leu Lys Thr Ser Glu Ser Gly Thr Pro Ser Ser Ser
    255                 260                 265

act cct caa gaa aac acc ata tct gga tat agc ctt tta acc tgc aaa      926
Thr Pro Gln Glu Asn Thr Ile Ser Gly Tyr Ser Leu Leu Thr Cys Lys
270                 275                 280                 285

aga act tta cct gaa ccc tgc cat tct aaa att tac ccg gga gtt gac      974
Arg Thr Leu Pro Glu Pro Cys His Ser Lys Ile Tyr Pro Gly Val Asp
                290                 295                 300

ttt gga gga gaa gaa ttg aat gtg act ttt gtt aaa gga gtg aat gtt     1022
Phe Gly Gly Glu Glu Leu Asn Val Thr Phe Val Lys Gly Val Asn Val
            305                 310                 315

tgc caa gag act tgc aca aag atg att cgc tgt cag ttt ttc act tat     1070
Cys Gln Glu Thr Cys Thr Lys Met Ile Arg Cys Gln Phe Phe Thr Tyr
        320                 325                 330

tct tta ctc cca gaa gac tgt aag gaa gag aag tgt aag tgt ttc tta     1118
Ser Leu Leu Pro Glu Asp Cys Lys Glu Glu Lys Cys Lys Cys Phe Leu
    335                 340                 345
```

-continued

```
aga tta tct atg gat ggt tct cca act agg att gcg tat ggg aca caa      1166
Arg Leu Ser Met Asp Gly Ser Pro Thr Arg Ile Ala Tyr Gly Thr Gln
350                 355                 360                 365

ggg agc tct ggt tac tct ttg aga ttg tgt aac act ggg gac aac tct      1214
Gly Ser Ser Gly Tyr Ser Leu Arg Leu Cys Asn Thr Gly Asp Asn Ser
                370                 375                 380

gtc tgc aca aca aaa aca agc aca cgc att gtt gga gga aca aac tct      1262
Val Cys Thr Thr Lys Thr Ser Thr Arg Ile Val Gly Gly Thr Asn Ser
            385                 390                 395

tct tgg gga gag tgg ccc tgg cag gtg agc ctg cag gtg aag ctg aca      1310
Ser Trp Gly Glu Trp Pro Trp Gln Val Ser Leu Gln Val Lys Leu Thr
        400                 405                 410

gct cag agg cac ctg tgt gga ggg tca ctc ata gga cac cag tgg gtc      1358
Ala Gln Arg His Leu Cys Gly Gly Ser Leu Ile Gly His Gln Trp Val
    415                 420                 425

ctc act gct gcc cac tgc ttt gat ggg ctt ccc ctg cag gat gtt tgg      1406
Leu Thr Ala Ala His Cys Phe Asp Gly Leu Pro Leu Gln Asp Val Trp
430                 435                 440                 445

cgc atc tat agt ggc att tta aat ctg tca gac att aca aaa gat aca      1454
Arg Ile Tyr Ser Gly Ile Leu Asn Leu Ser Asp Ile Thr Lys Asp Thr
                450                 455                 460

cct ttc tca caa ata aaa gag att att att cac caa aac tat aaa gtc      1502
Pro Phe Ser Gln Ile Lys Glu Ile Ile Ile His Gln Asn Tyr Lys Val
            465                 470                 475

tca gaa ggg aat cat gat atc gcc ttg ata aaa ctc cag gct cct ttg      1550
Ser Glu Gly Asn His Asp Ile Ala Leu Ile Lys Leu Gln Ala Pro Leu
        480                 485                 490

aat tac act gaa ttc caa aaa cca ata tgc cta cct tcc aaa ggt gac      1598
Asn Tyr Thr Glu Phe Gln Lys Pro Ile Cys Leu Pro Ser Lys Gly Asp
    495                 500                 505

aca agc aca att tat acc aac tgt tgg gta acc gga tgg ggc ttc tcg      1646
Thr Ser Thr Ile Tyr Thr Asn Cys Trp Val Thr Gly Trp Gly Phe Ser
510                 515                 520                 525

aag gag aaa ggt gaa atc caa aat att cta caa aag gta aat att cct      1694
Lys Glu Lys Gly Glu Ile Gln Asn Ile Leu Gln Lys Val Asn Ile Pro
                530                 535                 540

ttg gta aca aat gaa gaa tgc cag aaa aga tat caa gat tat aaa ata      1742
Leu Val Thr Asn Glu Glu Cys Gln Lys Arg Tyr Gln Asp Tyr Lys Ile
            545                 550                 555

acc caa cgg atg gtc tgt gct ggc tat aaa gaa ggg gga aaa gat gct      1790
Thr Gln Arg Met Val Cys Ala Gly Tyr Lys Glu Gly Gly Lys Asp Ala
        560                 565                 570

tgt aag gga gat tca ggt ggt ccc tta gtt tgc aaa cac aat gga atg      1838
Cys Lys Gly Asp Ser Gly Gly Pro Leu Val Cys Lys His Asn Gly Met
    575                 580                 585

tgg cgt ttg gtg ggc atc acc agc tgg ggt gaa ggc tgt gcc cgc agg      1886
Trp Arg Leu Val Gly Ile Thr Ser Trp Gly Glu Gly Cys Ala Arg Arg
590                 595                 600                 605

gag caa cct ggt gtc tac acc aaa gtc gct gag tac atg gac tgg att      1934
Glu Gln Pro Gly Val Tyr Thr Lys Val Ala Glu Tyr Met Asp Trp Ile
                610                 615                 620

tta gag aaa aca cag agc agt gat gga aaa gct cag atg cag tca cca      1982
Leu Glu Lys Thr Gln Ser Ser Asp Gly Lys Ala Gln Met Gln Ser Pro
            625                 630                 635

gca tga gaagcagtcc agagtctagg caatttttac aacctgagtt caagtcaaat      2038
Ala

tctgagcctg gggggtcctc atctgcaaag catggagagt ggcatcttct ttgcatccta   2098

aggacgaaaa acacagtgca ctcagagctg ctgaggacaa tgtctggctg aagcccgctt   2158
```

```
tcagcacgcc gtaaccaggg gctgacaatg cgaggtcgca actgagatct ccatgactgt   2218

gtgttgtgaa ataaaatggt gaaagatcaa aaaa                              2252


<210> SEQ ID NO 2
<211> LENGTH: 578
<212> TYPE: DNA
<213> ORGANISM: Homo sapiens

<400> SEQUENCE: 2

atgctctctc tctctcctgc tgccttgtga agaaggtacc tgcttcccct tcaccttcca     60

ccataattct gaacacggat aggatgttca tggaatatgt tgacaggaca aaaagttgaa    120

actgttggca gaaacccaaa gtcaatattg aagccaagca aaatattgcc tgcagtgcca    180

cattagaaca gcttgaagac cgttcatttt taagtgacaa gagactcacc tccaagaagc    240

aattgtgttt tcagaatgat tttattcaag caagcaactt atttcatttc cttgtttgct    300

acagtttcct gtggatgtct gactcaactc tatgaaaacg ccttcttcag aggtggggat    360

gtagcttcca tgtacacccc aaatgcccaa tactgccaga tgaggtgcac attccaccca    420

aggtgtttgc tattcagttt tcttccagca agttcaatca atgacatgga gaaaaggttt    480

ggttgcttct tgaaagatag tgttacagga accctgccaa aagtacatcg aacaggtgca    540

gtttctggac attccttgaa gcaatgtggt catcaaat                            578


<210> SEQ ID NO 3
<211> LENGTH: 681
<212> TYPE: DNA
<213> ORGANISM: Homo sapiens

<400> SEQUENCE: 3

ggaagccatt cactagtcag attgaccaga gattgttggt gggctgtctg ttggggtcta     60

tgcacaggat ttctgctgga gttctaagga caaaaagttg aaactgttgg cagaaaccca    120

aagtcaatat tgaagccaag caaaatattg cctgcagtgc cacattagaa cagcttgaag    180

accgttcatt tttaagtgac aagagactca cctccaagaa gcaattgtgt tttcagaatg    240

attttattca agcaagcaac ttatttcatt tccttgtttg ctacagtttc ctgtggatgt    300

ctgactcaac tctatgaaaa cgccttcttc agaggtgggg atgtagcttc catgtacacc    360

ccaaatgccc aatactgcca gatgaggtgc acattccacc caaggtgttt gctattcagt    420

tttcttccag caagttcaat caatgacatg gagaaaaggt ttggttgctt cttgaaagat    480

agtgttacag gaaccctgcc aaaagtacat cgaacaggtg cagtttctgg acattccttg    540

aagcaatgtg gtcatcaaat aagtgcttgc catcgagaca tttataaagg agttgatatg    600

agaggagtca attttaatgt gtctaaggtt agcagtgttg aagaatgcca aaaaaggtgc    660

accagtaaca ttcgctgcca g                                              681


<210> SEQ ID NO 4
<211> LENGTH: 2175
<212> TYPE: DNA
<213> ORGANISM: Homo sapiens
<220> FEATURE:
<221> NAME/KEY: CDS
<222> LOCATION: (255)..(1799)

<400> SEQUENCE: 4

agaacagctt gaagaccgtt catttttaag tgacaagaga ctcacctcca agaagcaatt     60

gtgttttcag tttcctgtga gggagttttc tctgtgtccc cacaaggcat gattctgggt    120
```

-continued

```
ctatggtgac ttaagagggc cacacaacaa tgagtattta attttcctca gatgtatggc    180

tacaataaac atctatagga tgtctgactc aactctatga aaacgccttc ttcagaggtg    240

gggatgtagc ttcc atg tac acc cca aat gcc caa tac tgc cag atg agg      290
                Met Tyr Thr Pro Asn Ala Gln Tyr Cys Gln Met Arg
                1               5                   10

tgc aca ttc cac cca agg tgt ttg cta ttc agt ttt ctt cca gca agt      338
Cys Thr Phe His Pro Arg Cys Leu Leu Phe Ser Phe Leu Pro Ala Ser
        15                  20                  25

tca atc aat gac atg gag aaa agg ttt ggt tgc ttc ttg aaa gat agt      386
Ser Ile Asn Asp Met Glu Lys Arg Phe Gly Cys Phe Leu Lys Asp Ser
    30                  35                  40

gtt aca gga acc ctg cca aaa gta cat cga aca ggt gca gtt tct gga      434
Val Thr Gly Thr Leu Pro Lys Val His Arg Thr Gly Ala Val Ser Gly
45                  50                  55                  60

cat tcc ttg aag caa tgt ggt cat caa ata agt gct tgc cat cga gac      482
His Ser Leu Lys Gln Cys Gly His Gln Ile Ser Ala Cys His Arg Asp
                65                  70                  75

att tat aaa gga gtt gat atg aga gga gtc aat ttt aat gta tct aag      530
Ile Tyr Lys Gly Val Asp Met Arg Gly Val Asn Phe Asn Val Ser Lys
            80                  85                  90

gtt agc agt gtt gaa gaa tgc caa aaa agg tgc acc aat gac att cgc      578
Val Ser Ser Val Glu Glu Cys Gln Lys Arg Cys Thr Asn Asp Ile Arg
        95                  100                 105

tgc cag ttt ttt tca tat gcc acg caa aca ttt cac aag gca gag tac      626
Cys Gln Phe Phe Ser Tyr Ala Thr Gln Thr Phe His Lys Ala Glu Tyr
    110                 115                 120

cgg aac aat tgc cta tta aag tac agt ccc gga gga aca cct acc gct      674
Arg Asn Asn Cys Leu Leu Lys Tyr Ser Pro Gly Gly Thr Pro Thr Ala
125                 130                 135                 140

ata aag gtg ctg agt aac gtg gaa tct gga ttc tca ctg aag ccc tgt      722
Ile Lys Val Leu Ser Asn Val Glu Ser Gly Phe Ser Leu Lys Pro Cys
                145                 150                 155

gcc ctt tca gaa att ggt tgc caa atg aac atc ttc cag cat ctt gcg      770
Ala Leu Ser Glu Ile Gly Cys Gln Met Asn Ile Phe Gln His Leu Ala
            160                 165                 170

ttc tca gat gtg gat gtt gcc agg gtt ctc act cca gat gct ttt gtg      818
Phe Ser Asp Val Asp Val Ala Arg Val Leu Thr Pro Asp Ala Phe Val
        175                 180                 185

tgt cgg acc atc tgc acc tat cac ccc aac tgc ctc ttc ttt aca ttc      866
Cys Arg Thr Ile Cys Thr Tyr His Pro Asn Cys Leu Phe Phe Thr Phe
    190                 195                 200

tat aca aat gta tgg aaa atc gag tca caa aga aat gtt tgt ctt ctt      914
Tyr Thr Asn Val Trp Lys Ile Glu Ser Gln Arg Asn Val Cys Leu Leu
205                 210                 215                 220

aaa aca tct gaa agt ggc aca cca agt tcc tgt act cct caa gaa aac      962
Lys Thr Ser Glu Ser Gly Thr Pro Ser Ser Cys Thr Pro Gln Glu Asn
                225                 230                 235

acc ata tct gga tat agc ctt tta acc tgc aaa aga act tta cct gaa     1010
Thr Ile Ser Gly Tyr Ser Leu Leu Thr Cys Lys Arg Thr Leu Pro Glu
            240                 245                 250

ccc tgc cat tct aaa att tac ccg gga gtt gac ttt gga gga gaa gaa     1058
Pro Cys His Ser Lys Ile Tyr Pro Gly Val Asp Phe Gly Gly Glu Glu
        255                 260                 265

ttg aat gtg act ttt gtt aaa gga gtg aat gtt tgc caa gag act tgc     1106
Leu Asn Val Thr Phe Val Lys Gly Val Asn Val Cys Gln Glu Thr Cys
    270                 275                 280

aca aag atg att cgc tgt cag ttt ttc act tat tct tta ctc cca gaa     1154
Thr Lys Met Ile Arg Cys Gln Phe Phe Thr Tyr Ser Leu Leu Pro Glu
```

-continued

```
285                 290                 295                 300

gac tgt aag gaa gag aag tgt aag tgt ttc tta aga tta tct atg gat      1202
Asp Cys Lys Glu Glu Lys Cys Lys Cys Phe Leu Arg Leu Ser Met Asp
                305                 310                 315

ggt tct cca act agg att gcg tat ggg aca caa ggg agc tct ggt tac      1250
Gly Ser Pro Thr Arg Ile Ala Tyr Gly Thr Gln Gly Ser Ser Gly Tyr
            320                 325                 330

tct ttg aga ttg tgt aac act ggg gac aac tct gtc tgc aca aca aaa      1298
Ser Leu Arg Leu Cys Asn Thr Gly Asp Asn Ser Val Cys Thr Thr Lys
        335                 340                 345

aca agc aca cgc att gtt gga gga aca aac tct tct tgg gga gag tgg      1346
Thr Ser Thr Arg Ile Val Gly Gly Thr Asn Ser Ser Trp Gly Glu Trp
    350                 355                 360

ccc tgg cag gtg agc ctg cag gtg aag ctg aca gct cag agg cac ctg      1394
Pro Trp Gln Val Ser Leu Gln Val Lys Leu Thr Ala Gln Arg His Leu
365                 370                 375                 380

tgt gga ggg tca ctc ata gga cac cag tgg gtc ctc act gct gcc cac      1442
Cys Gly Gly Ser Leu Ile Gly His Gln Trp Val Leu Thr Ala Ala His
                385                 390                 395

tgc ttt gat ggg ctt ccc ctg cag gat gtt tgg cgc atc tat agt ggc      1490
Cys Phe Asp Gly Leu Pro Leu Gln Asp Val Trp Arg Ile Tyr Ser Gly
            400                 405                 410

att tta aat ctg tca gac att aca aaa gat aca cct ttc tca caa ata      1538
Ile Leu Asn Leu Ser Asp Ile Thr Lys Asp Thr Pro Phe Ser Gln Ile
        415                 420                 425

aaa gag att att att cac caa aac tat aaa gtc tca gaa ggg aat cat      1586
Lys Glu Ile Ile Ile His Gln Asn Tyr Lys Val Ser Glu Gly Asn His
    430                 435                 440

gat atc gcc ttg ata aaa ctc cag gct cct ttg aat tac act gaa ttc      1634
Asp Ile Ala Leu Ile Lys Leu Gln Ala Pro Leu Asn Tyr Thr Glu Phe
445                 450                 455                 460

caa aaa cca ata tgc cta cct tcc aaa ggt gac aca agc aca att tat      1682
Gln Lys Pro Ile Cys Leu Pro Ser Lys Gly Asp Thr Ser Thr Ile Tyr
                465                 470                 475

acc aac tgt tgg gta acc gga tgg ggc ttc tcg aag gag aaa ggg aga      1730
Thr Asn Cys Trp Val Thr Gly Trp Gly Phe Ser Lys Glu Lys Gly Arg
            480                 485                 490

ttc agg tgg tcc ctt agt ttg caa aca caa cgg aat gtg gcg ttt ggt      1778
Phe Arg Trp Ser Leu Ser Leu Gln Thr Gln Arg Asn Val Ala Phe Gly
        495                 500                 505

ggg cat cac cag ctg ggg tga aggctgtgcc cgcagggagc aacctggtgt        1829
Gly His His Gln Leu Gly
    510

ctacaccaaa gtcgctgagt acatggactg gattttagag aaaacacaga gcagtgatgg   1889

aaaagctcag atgcagtcac cagcatgaga agcagtccag agtctaggca atttttacaa   1949

cctgagttca agtcaaattc tgagcctggg ggtcctcat ctgcaaagca tggagagtgg    2009

catcttcttt gcatcctaag gacgaaagac acagtgcact cagagctgct gaggacaatg   2069

tctggctgaa gcccgctttc agcacgccgt aaccaggggc tgacaatgcg aggtcgcaac   2129

tgagatctcc atgactgtgt gttgtgaaat aaaatggtga aagatc                  2175


<210> SEQ ID NO 5
<211> LENGTH: 569
<212> TYPE: DNA
<213> ORGANISM: Homo sapiens

<400> SEQUENCE: 5

agtgccacat tagaacagct tgaagaccgt tcatttttaa gtgacaagag actcacctcc     60
```

aagaagcaat tgtgttttca gtttcctgtg gatgtctgac tcaactctat gaaaacgcct 120
tcttcagagg tggggatgta gcttccatgt acaccccaaa tgcccaatac tgccagatga 180
ggtgcacatt ccacccaagg tgtttgctat tcagttttct tccagcaagt tcaatcaatg 240
acatggagaa aaggtttggt tgcttcttga aagatagtgt tacaggaacc ctgccaaaag 300
tacatcgaac aggtgcagtt tctggacatt ccttgaagca atgtggtcat caaataagtg 360
cttgccatcg agacatttat aaaggagttg atatgagagg agtcaatttt aatgtgtcta 420
aggttagcag tgttgaagaa tgccaaaaaa ggtgcaccaa taacattcgc tgccagtttt 480
tttcatatgc cacgcaaaca tttcacaagg cagagtaccg gaacaattgc ctattaaagt 540
acagtcccgg aggaacacct accgctata 569

<210> SEQ ID NO 6
<211> LENGTH: 392
<212> TYPE: DNA
<213> ORGANISM: Homo sapiens
<220> FEATURE:
<221> NAME/KEY: misc_feature
<222> LOCATION: (379)..(379)
<223> OTHER INFORMATION: n is a, c, g, or t

<400> SEQUENCE: 6
ttgaagaccg ttcattttta agtgacaaga gactcacctc caagaagcaa ttgtgttttc 60
agaatgattt tattcaagca agcaacttat ttcatttcct tgtttgctac agtttcctgt 120
ggatgtctga ctcaactcta tgaaaacgcc ttcttcagag gtggggatgt agcttccatg 180
tacaccccaa atgcccaata ctgccagatg aggtgcacat tccacccaag gtgtttgcta 240
ttcagttttc ttccagcaag ttcaatcaat gacatggagg gtttggttgc ttcttgaaag 300
atagtgttac aggaaccctg cctcaaataa gtgcttgcca tcgagacatt tatggagttg 360
atatgagagg agtcaattnt atgtgtctgg tt 392

<210> SEQ ID NO 7
<211> LENGTH: 802
<212> TYPE: DNA
<213> ORGANISM: Homo sapiens
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t

<400> SEQUENCE: 7
gggtaatcct cttcagttac ttcaggtcat ctagatgtat acgtgcaggc ctgggcccag 60
aggcgacatt cctgtcttct tatattaata agaaaaagaa aacgaaatag tggttgccac 120
atgaacatct tccagcatct tgcgttctca gatgtggatg ttgccagggc tctcactcca 180

-continued

```
gatgcttttg tgtgtcggac catctgcacc tatcacccca actgcctctt ctttacattc    240

tatacaaatg tatggaaaat cgagtcacaa aggcgagtat gcatggaaaa tcgcatcaca    300

aaggcgagta tgcatgggga gcacttgctg ctgtactttc atcactttta tagtctgagt    360

tcttaaaagt ttcgttcatt tccctcaaaa cacttgaacc tgcagtttca gtaggtactg    420

ttctgccagg tgcagattag ttaagagatt agcagacttc tctgcctatc ttctcttact    480

ttaaaacaaa tgttaccatt gaatcaagga agcaatagcc atgagaaaaa agaaggatct    540

gacgcctttg aatgaagatt caaaacatga tcttcatgtt ttgtattagc ttggagtaaa    600

atccacttgc tggcaatata gcccttaagc ttgttgcctc ttctctttgt ttcagaaact    660

agagccctgt ttattctgat caaggctctg gcccactgtc tttatctcag ataacccacc    720

ctcttctgca cacagcatgg agctaagaga aggtgtctan gtatgtatat catcngcagc    780

ataaatccca gaattngtcn tn                                              802


<210> SEQ ID NO 8
<211> LENGTH: 2058
<212> TYPE: DNA
<213> ORGANISM: Homo sapiens

<400> SEQUENCE: 8

tcacctccaa gaagcaattg tgttttcaga atgattttat tcaagcaagc aacttatttc     60

atttccttgt ttgctacagt ttcctgtgga tgtctgactc aactctatga aaacgccttc    120

ttcagaggtg gggatgtagc ttccatgtac accccaaatg cccaatactg ccagatgagg    180

tgcacattcc acccaaggtg tttgctattc agttttcttc cagcaagttc aatcaatgac    240

atggagaaaa ggtttggttg cttcttgaaa gatagtgtta caggaaccct gccaaaagta    300

catcgaacag gtgcagtttc tggacattcc ttgaagcaat gtggtcatca aataagtgct    360

tgccatcgag acatttataa aggagttgat atgagaggag tcaattttaa tgtgtctaag    420

gttagcagtg ttgaagaatg ccaaaaaagg tgcaccaata acattcgctg ccagtttttt    480

tcatatgcca cgcaaacatt tcacaaggca gagtaccgga acaattgcct attaaagtac    540

agtcccggag gaacacctac cgctataaag gtgctgagta acgtggaatc tggattctca    600

ctgaagccct gtgccctttc agaaattggt tgccacatga acatcttcca gcatcttgcg    660

ttctcagatg tggatgttgc cagggttctc actccagatg cttttgtgtg tcggaccatc    720

tgcacctatc accccaactg cctcttcttt acattctata caaatgtatg gaaaatcgag    780

tcacaaaggc gagtatgcat ggaaaatcgc atcacaaaga aatgtttgtc ttcttaaaac    840

atctgaaagt ggcacaccaa gttcctctac tcctcaagaa aacaccatat ctggatatag    900

ccttttaacc tgcaaaagaa ctttacctga accctgccat tctaaaattt acccgggagt    960

tgactttgga ggagaagaat tgaatgtgac ttttgttaaa ggagtgaatg tttgccaaga   1020

gacttgcaca aagatgattc gctgtcagtt tttcacttat tctttactcc cagaagactg   1080

taaggaagag aagtgtaagt gtttcttaag attatctatg gatggttctc caactaggat   1140

tgcgtatggg acacaaggga gctctggtta ctctttgaga ttgtgtaaca ctggggacaa   1200

ctctgtctgc acaacaaaaa caagcacacg cattgttgga ggaacaaact cttcttgggg   1260

agagtggccc tggcaggtga gcctgcaggt gaagctgaca gctcagaggc acctgtgtgg   1320

agggtcactc ataggacacc agtgggtcct cactgctgcc cactgctttg atgggcttcc   1380

cctgcaggat gtttggcgca tctatagtgg cattttaaat ctgtcagaca ttacaaaaga   1440

tacacctttc tcacaaataa aagagattat tattcaccaa aactataaag tctcagaagg   1500
```

gaatcatgat atcgccttga taaaactcca ggctcctttg aattacactg aattccaaaa 1560
accaatatgc ctaccttcca aaggtgacac aagcacaatt tataccaact gttgggtaac 1620
cggatggggc ttctcgaagg agaaaggtga aatccaaaat attctacaaa aggtaaatat 1680
tcctttggta acaaatgaag aatgccagaa aagatatcaa gattataaaa taacccaacg 1740
gatggtctgt gctggctata aagaaggggg aaaagatgct tgtaagggag attcaggtgg 1800
tcccttagtt tgcaaacaca atggaatgtg gcgtttggtg ggcatcacca gctggggtga 1860
aggctgtgcc cgcagggagc aacctggtgt ctacaccaaa gtcgctgagt acatggactg 1920
gattttagag aaaacacaga gcagtgatgg aaaagctcag atgcagtcac cagcatgaga 1980
agcagtccag agtctaggca atttttacaa cctgagttca agtcaaattc tgagcctggg 2040
gggtcctcat ctgcaaag 2058

<210> SEQ ID NO 9
<211> LENGTH: 577
<212> TYPE: DNA
<213> ORGANISM: Homo sapiens

<400> SEQUENCE: 9
gttaccattc taaaatttac ccgggagttg actttggagg agaagaattg aatgtgactt 60
ttgttaaagg agtgaatgtt tgccaagaga cttgcacaaa gatgattcgc tgtcagtttt 120
tcacttattc tttactccca gaagactgta aggaagagaa gtaaaggaaa ttttattttt 180
caaagacagt tgacatgacc atttcatatt ctctttcccc ctgtgaaggc ttactctttc 240
tactgttcat ttcatctagg tgtaagtgtt tcttaagatt atctatggat ggttctccaa 300
ctaggattgc gtatgggaca caagggagct ctggttactc tttgagattg tgtaacactg 360
gggacaactc tggtgagtaa cctcactttt tcgtggacct gtcagggatg tctgtcatgt 420
tgatagtttg cttagtctta aggaattatg tgtcttgttc tccttggtta gaagggactt 480
tgattcactt ctaattccaa ccattagcgt caacgctctc ttttcagtct gcacaacaaa 540
aacaagcaca cgcattgttg gaggaacaaa ctcttct 577

<210> SEQ ID NO 10
<211> LENGTH: 37000
<212> TYPE: DNA
<213> ORGANISM: Homo sapiens

<400> SEQUENCE: 10
agagcctctg cctagatttc acaggatgtg tggaaacacc tggctgtcca ggcagaagcc 60
tgctgcaggg acccagccct catggagaac ctctattagg gcagtgcaga ggtgaactgt 120
ggggttggag cccacacaca gagaccccac tggagcactg cccagtggag ctgtgaaaag 180
agttccccca tcttccagat gccagaatgg tagatccact gactggaaag ttgcaggcac 240
tcagtgccgg cccatgaagg cagccgtagg ggctgtaccc tgcaaagcca cagggacaga 300
gctgcccaag gccttaacag cccacacctt gcatcagcat gccctgggtg tgagacaggg 360
gctccaagga gattattttg gagctttaaa atttaatgac ttccctgcta ggttttgcat 420
atgcttggga cctgtggccc ctttattttg gccaatttct cccatttgga atgggaacat 480
ttacccaatt cctgtaccca cattgtgttt tggaagtaac taacttgttt tttattttaa 540
aggctcattg agggaaggga cttgccttgt ctcaaatgag actttggact cggacttttg 600
ggttactgtg gaatgagtta agactttggg ggactgttgg aaagacatca ttggttttga 660

-continued

```
aatctgaaaa ggacatgaga tttgggaaag gccaggggaa gaatgatatg gtttggctct    720
gtgtcctcat ccaaatctcg tcttgaattg taatccccac atgggattac atgggagggg    780
cctggtgaga ggtgattgga tcatggaggt ggtttcccct gtgctgtgat ctcatgatag    840
tgagggattt aaaagtgaca gtttcccctg cacatacaca ctctctctct cgtatcacct    900
tgtgaagaag gtgtctgctt cccctctgcc ttccatcgtg attataagtt tcctgaggcc    960
tccccagcca tgggtaactg tgagtcagtt aaacctcttt tgtttataaa ttacccagtc   1020
tcaggtagta tctttacagc agtgtgaaac tggactaata catctgggaa attctttttg   1080
tctccttcct ttctgaagga cagctttgcc tgatattata ttcttggttg ccaggttttg   1140
tactttcaat actttgaata tatcatccca ctctctcttg gcctacatga tttctgctga   1200
gaaatccacc aataatctta tgaagcttcc cttgtatgtg aagaattgct tttctcttgc   1260
ttctttgaaa attctctctt tgtcatggtg aggatttctt tttttttttt tttttttag   1320
atggagtcta gctctgttgt ccaggctgga gtgcagtgtg cagtggcgca atctcggctc   1380
actgcaagct ccgtctcctg ggttcacacc attttcctgt ctcagcctct ggagtagctg   1440
agactacagg tgcccaccac cacgcctggc taaatttttt ttgtattttt agtagagatg   1500
gggtttcact gtgttagcca ggatggtctc gatctcctga cctcatgatc cacccatctt   1560
ggcctcccaa agtgctggga ttacaggcat gagccactgc acctggccga ggatctcttt   1620
atatttaatc tatttggagt tcttttgggc ttcataaatc tggatgttta tttcatttat   1680
gtctccaaat tttgagagtt ttctattctt attttttttaa ataagtttct gcaactttct   1740
ctttctctac ttcttctgga actcttctaa tgcatattaa ttttcttaac agtgtcctat   1800
aagtcttgtc agctttctgc aatttttatc attcctttta ttactctgac tgggtaattt   1860
caaatgacct gtatctgagc atgctgattc tttctcctgc ttgatctagt ctgctgctga   1920
agctgtttgt gaatttttc aattcagtca ttttgttctt tagctccaga atttctgttt    1980
cattcttttt tatggttcct atctatcttt ttgttgaact tctaattttg ctcatgtatt   2040
gttttcctga ttttgtttac tgtctatcta tattgttttg tagcttattg agctttctta   2100
aggcaattat ttttagctct tgtcatgcag taaagatctc catttcttta gggtcacctc   2160
ctgctgcttt atttccttcc tttggtggtt tcttgtttcc ccgattattt gtgatcagtg   2220
tggccttgca ctgaagtagg cacctatttc agtctttaca tactagcttc agcagagaaa   2280
gccattcact agtcagattg accagagatt gttggtgggc tgtctgttgg ggtctatgca   2340
caggatttct gctggagttc taaggtggga agggctggat tctgggttca ttcactgtgg   2400
ttgtctgtat tctgtgcaca aggactggct tgaagcatgg atccttgggg gctgacttgg   2460
cactgaaatg agccttaagc ctgcgtctgc aggggccagc ctaacatggg gatcacctgg   2520
cacctgagtt catggggata ggcctgttcc tgagtttatt caggctgtcc tgggaacaag   2580
gtccactggg gtgagcccag catctgggtc cacatggccc agcatggagc caagatctct   2640
ggaggctgac ctggtgctgg atctgcaggg gatggcctgg attctaggcc catgggtgcc   2700
aacttggagc ctggggttgc tggggctaac gtggaggcta gatagagtct tgggggccag   2760
gctagagctg gagcaggcct gaagtctagg ttttgtgtgg ccatcttgga gcctgaagcc   2820
ccaggggctg acctggtctg gggtgagcat ggggctgagg ccacagaggc tggtctggcc   2880
tgtggcaggc ctgaatcctg gtgctggggt ttactggagt gggcttggtg cttgggatct   2940
gtggtgaagt taggttctat cttaactgtc cctcctccat gcaagagggc atctctctcc   3000
atactgtgct gcccaggctt gaaggtgaga tgacaccggt aatgtgaaat tgtccttcct   3060
```

-continued atacacttct atgtgtcttt tcttatttct gtgctgcaac caggtggcat aacctctcac 3120
ctgattcctt agctctagtg aagttatttt cgtgcatgga tacttgttcg aattgatgtt 3180
tctgcaaggg atgagcgcta gaaactcctg ttctgacaaa ctcctattcc tattcttgct 3240
gacatcactc cctgaaatag ttaatatact taacagctga acacggatag gatgttcatg 3300
gaatatgttg acaggacaaa aagttgaaac tgttggcaga aacccaaagt caatattgaa 3360
gccaagcaaa atattgcctg cagtgccaca ttagaacagc ttgaagaccg ttcattttta 3420
agtgacaaga gactcacctc caagaagcaa ttgtgttttc aggtagcaaa tttttattat 3480
tctgattgtt tccaaataaa ctataatttt taagtataat tttttacttt atgagaaaat 3540
taatcattta tattctaatt tcctgagtat gtagagagta tagataatgt tcctttatgt 3600
agaaatattt aaatgtaaga tgattttaaa tcagaaagaa tatttgattg atttaaaatt 3660
tttaaatggg ctttaatatt ttcagaggtt ttctttactt agggattttt ggactgacat 3720
tattgccatt atttattaat tttgtttttg cccaaatcaa gaggtttcat aattgtttac 3780
tctctctcta ccaattccct ttccaacatt actagccaca gagttggcca atgaacaata 3840
aacacaacag tagtctggag gtctcaattt gtatcttggg aagcattata aattttccaa 3900
ctccctagac acaaatgtac caaaaaaaaa cccttgtttt ctataccagt aattgtgtgc 3960
tttgtcttgc aattcagaca tttacaagaa aatctaaatc accttaaatt aagatttatg 4020
ttaaatgtgg tctaaaacca gcagagttat gtattgtttt ctttttttaga atgattttat 4080 tcaagcaagc aacttatttc atttccttgt ttgctacagt ttcctgtggt aagtgaatta 4140
tctataaaac atggaattca ggctaagaca ggagtagcca agcaagtggc accaccccctg 4200 gagaaagcta ttgaacatac agcttcgggg gtggagattg tccctgatga ttcaggacac 4260
gtgtctattt aatgttccac aacaaggacc acttgtcagg tatattgctg tagacatatg 4320
ttgcagacca gaggaaggag ctcagaagta ggaatgtctt gggacttgtg ttaacaaaaa 4380
cttctgttcg cagatgacac tctgcaaagc aaaacttgaa acaaaaaaaa attagtcctc 4440
tatttttatt atcaacagta aaaaattaaa ctttatctga aaattcaaaa gagtgctagg 4500
cattttatag tgtctgggtc caatccaagt atctgttagg aacaccatac atagttttac 4560
tctggaccgc tagggaacca tttcaaaaat gaaagtaact ggtttaaatt taacttagca 4620
aaccatgcat ttggatagtt ctaggtgaat agctttcaac accagattta gatctcattt 4680
ctctattaat ttcattaatt tttggagaat aaaaatgatt ctggacattt cattaatcat 4740
tacagaggga gttttctctg tgtccccaca aggcatgatt ctgggtctat ggtgacttaa 4800
gagggccaca caacaatgag tatttaattt tcctcagatg tatggctaca ataaacatct 4860
ataggtaagg tttacattca taaagagacc tttttttttc caggaaaaaa gacttttatt 4920
ccccctaaat cacaactccc ctgtgtctgt ccctcaaccc tgatttctct tctaaaccgt 4980
aatttacaaa cccatgtgca aacccactga aaggtgagaa ggagcataag ccagagacac 5040
tgggaaccac agccaactac agggggtttt tcattttttt gttttgtttt gttttttggc 5100
aaaataaatc atgattatgg ctaggaaaat cagggatgta agtaagcaaa aatttagaaa 5160
ctacatattg catgtagtcc ccaaattcag aaacagtcat cgttaaacat cttttattta 5220
gtctttcaga tatttttcta catataccta tttgcacatt tcacaaaaaa gagttattaa 5280
ctgtggacac tctttgactt gcattttcca cttatagcta tcttttggtg caaataagta 5340
atatattttg gagcttgcta ttcttctctt tttatggtat ttttgtgtgc acattcttat 5400
gctcttattc agttatttct gtagaataca atttttgaaa taaaaatact agattcaaag 5460
gtgtgaatat ttttgaaggt tttgtggtgt ggtatcatga aattaggttt cagaaagttt 5520
actccatagt tgactttttc taccagctaa taagagtgct catttacccc acttaggcca 5580
actctaacag gcttctgttg ctttgcatcc tgacatattt atctttctgg aaacagtgtc 5640
ctaatttatt tctgcagagc tactgcctct cagttttggt ccatgtggtt ctggtgaccc 5700
tgattcttct gctgaaccag aaagtgcaca catcctcctg gctgtggtga cccaatcaga 5760
gccaacgtct tgcaatgaag cttttcttta gacatctaga aataagactc ttatgttttt 5820
tttttccaat ttgacttgaa acttaagaca atacacaggc ctgagttgtt ggtactattt 5880
tgctactacg tggagcttga gagtaatggt aacaccaaga ctggagcaag tggaaggaga 5940
catattgtcc actgatgcta tcagttgagc acaatgtgca gttacttttt aagccagatt 6000
caccatgggc tttttggctc ctgaaccaat agatttcatt tgttttcaag ccactttgta 6060
ctaggttttc catcatttgc aatcaaaacc agtatacaaa cactggttat ttaatttttc 6120
atttttgcta atctcaggga taaaatggct tctagttgtt ttaacttggc tatatttgtg 6180
attcttccca ttttcatata cttactaatc acttctattt cttttgtaaa ttatcttttc 6240
atatttgtta tctaattctt taaaatttga gtactttaat tctcattatt gtttgtggaa 6300
ttgttaaaca agactgaata atctgcccaa agtccatgga catgggggcc catgtaaaag 6360
ctttgaaagc caccatcatt atgagataaa ttatataata gtactttaca taggctccaa 6420
aatacagcac agacacagct atcattgtca tggtcatcat tatcatcatg atcaccaact 6480
tatgaggata agcaagaaca cctactagaa gtttctttcc attcagcaac aaaattggtg 6540
tctttctagt cactcccttc cctgactgtc acatagcagt tcacagaggc tcagttgcag 6600
aatgagaagc tctgggccag gacctgccat tgtatgcatc cttgcatggg aactgggggc 6660
tggaagagga gtgactgctt gataattatg agtcagtcaa aaccaccaac tgtctgaaaa 6720
aaataggcct ttttgtaact agtattgtca ctaaaccaac tcctccatgt tttgtgcata 6780
catgaaatct aggcaataca cttgtattcc caaaagcttc cacttgaaga gatctgtgct 6840
ctttccaaat ataaacctta cccgagaggt ggtcatcttg gccacacctc agagagggag 6900
agaggcagtc ttgttgggtt gggtggtcat aatggggctc agggccaaat ccccaggggg 6960
taggatagtg cagagaagat ggcactctcc agtgcttaat aaaatgcacg tggtctaagc 7020
tgcccactcc ctcaaaggca ataaaaaata ggtactattt aaattgaaga gtaactactg 7080
ccccagggaa tggacaggtt gtcattggaa tagccatggt taatggtccc agttgacaac 7140
tgaaatgaat gtgctacctg aacaggaaag cttattaacc agatttcaaa gacagtcttt 7200
cccggtaaat ccaaatttac aaattaaagc cagtaaagac accgaattct ctaataatat 7260
gtggggtgca gtatatttta gagctgggaa taattccaaa cagcaaatag ttcaaaattt 7320
attttcaatt tagcatatgc atgcatttgc ttaaactgtc ttaaaaatga gtaaaaaata 7380
ctgtcagttt gtttcaatca tactgagatg aggaacaatg tttagcattg catgctagaa 7440
aaggacacag gattgggagt cagggctggg tgaccgtcac aggactttca ctaactgtgt 7500
ggatcttggg caagtctgtg tgccctgaga ctcagttatt taactttctt ttaaaaaaca 7560
tagtccagat gcagataaca aagcctgcct ctaatttccc ttacagaatt gtgagaagct 7620
ggtggagatg tttgttacaa aagtgttttg aaaatagagc aaatattatt ctttttaagg 7680
catgatgttt tcatagcatg tcaggcaaca ggaaaaaact aagttaggat tttattttat 7740
tgtggggaat ttatgtgcaa attattgtgc aatttaatga aaataagcca atgttttata 7800

-continued

```
cagaagtacc cagaaaatta aataacacta tacattgttc aaatagttgc cttaatatat   7860
tttattttct cagcataatt agagttgtat tatacaggtc tttgagtagt cagtcagtgg   7920
gagaagttaa gacaacagat atctttttat taaaattatt atatgaatta tcgcaaatta   7980
atttttatgg ttctgtcaca ggatgtctga ctcaactcta tgaaaacgcc ttcttcagag   8040
gtggggatgt agcttccatg tacaccccaa atgcccaata ctgccagatg aggtgcacat   8100
tccacccaag gtgtttgcta ttcagttttc ttccagcaag ttcaatcaat gacatggaga   8160
aaaggtaaaa gttggtattt cattattgga gaagctgttt ttcaaaactg aatcagtttt   8220
gtgcagaaag gtgtagtata actgagagtt cttcctcaca cggggttcaa ggaccagctt   8280
cagcaaaatc ccgtcaagtg gttcttacaa atgcagattc ctaggccaca acccagatct   8340
gctgaaccaa agtttcttgt gaccaggaat ctgcatttta aacaatcact gtgtttcttt   8400
aaagtagtag aagctagtca ttttctattc aaagcctcaa aatgcttgaa tatcattggg   8460
ctaagggatt gtctcaagaa agagtctaac aggtgcacat ttcatctgaa taaagaaaca   8520
gatttaactg tgtgacccat gatcacatta gcggatagca cagtccaaag aaaataacat   8580
aagacaagca ttttgctgag aatgtaattg agaaagatct agaacttgtg attttgggac   8640
agggcagttc taaatggggc ctatagtgag ccagtttggg cacctgtggc atgatgctat   8700
gtatggtgtg tgtgtgtatg tgtgcttgtg cttgtgtgaa tatgtattat taactggaaa   8760
tttgtaaaag tattggaaaa atagtactta cgattttgtg tgtgtgtgtg atggagtctc   8820
gctttgtagc ccaggctgga gtgcagtggc gtgatctcgg ctcactgcaa cttccacctc   8880
ccaggttcaa gcgattctcc tgcctcagcc tcccaagtag ctgggattac aggcacgcac   8940
caccacgtcc agctaatttt tgtagtttta gtagagacgg ggtttcacca cattggccag   9000
gctggccttg aactcctgac ctcgtgatcc acctgcctct acctcctaat gtgctgggat   9060
tacaggcatg agccaccgca cccagcggta attacaattt ttattaggtc agagagatgc   9120
ttattaatca cgagccacag tttcatctta atgatttttc cttttgatta atatccagag   9180
taagcttttc tttgttgttc ccatttccat gttcataact ctttactcat cttcactcta   9240
tgtgagttta ccaactagaa attggatagt cattctctga tcccacatgt taaacttgta   9300
gagaaaactc agattgtatg tgaggatcat catattaaaa gtggaggaag gttctagaat   9360
tcttataaat aatgaaatta acatgaaggt ggacatctaa gacagaggga agtcttccat   9420
taagtgcaga ctacaaggag ttaataagca agatgaacac gatatacaaa tccagctctt   9480
atcactaagt taacttttta agtaaatgaa agtatttgca aaaataatta ccaattgaga   9540
acatagttgc ctgaaagttt aagaacacag gaaaaatcat taactcttta atatggttga   9600
tttcctgtac ttaaaaaatg tgagtgtaaa gaaaacgcag tgatggagtt agatattatg   9660
gggtgttata aaattagctc taagagtgtt ctttccagca agtattgggg aagctatatt   9720
attttcctta ttcctggttt tatttgttag tgtgtagaaa atgctagaca tttcctcaat   9780
gtatgtttat tattctactt cctaagtaaa gctactttta aaataggttt ggttgcttct   9840
tgaaagatag tgttacagga accctgccaa aagtacatcg aacaggtgca gtttctggac   9900
attccttgaa gcaatgtggt catcaaataa gtggtaagtt gtgaatttct tagctacatt   9960
tgagttaata ttggatctcg cttagaacag cttttgctca aagtttgtac tgctacagct  10020
ttttggaagg catcactcat aaagatagga gatggggcag tattctggac acaaaagagg  10080
gacccatatt catctggaca cttctattgt ctttataaat caacacatac ttaatgagcc  10140
```

-continued tctattattt atgaggttag cgctcaagtg taagatttgc agaaaatgaa tccaaataat 10200
tgtgtctcgt ttccagataa gaatttttaa gaaaacacaa gggaacatct ctctcaagtt 10260
cacttgaggg taatttttac atcagtgatt ctcaaccagc agtgattttg tctcttccac 10320
tggggacatt tgacaatgtc tggagacatt tttggtggct acaactaggg aggatgctat 10380
tagcatttac taagtagagg ccagaatgtt tgaatgctga ccaacattct acaaggcaca 10440
gggcagtcgt ccacagcaaa taattttctg gcccaaaacg tcaacagtgc tgacatcaag 10500
aaactctgtg atataccact aggcccaaat tgaagaactg agttctgcaa atcttgctaa 10560
gaataatact tcctaaagga aacttgagga ctaggatgct agagaacttt gattctgaca 10620
tctgaagcta ctgatgtctt gggaaacagt ttccaatgct atcctaataa atttaagaca 10680
aatgaactat ttctcaaaca tgactgggac tgataagaaa gtgaaaagtg ctgaaaagat 10740
tcaactgatg ggttgtcaga atcttaaaat aactgctgtt attctatgta tgactatata 10800
tcattactat tttattttca ttatgcacaa ttaattttgt aggttcaaat ttcagatgtt 10860
tttaaatttg tcatcctttc ctccctcatt gatatcacct cttcaatacg tacacacttt 10920
gagcctgctg tttgcatttt aaccagttat caaaggatgg caatgccttc attataaatg 10980
tgggcctgac ttagccagta taataggtgt agtctacgtg aggtggagta catttcctat 11040
tttaaaagat caatttttat gttaatccaa tttggtataa attattcgag taagtgctat 11100
ttctgattgt tgtatcttgt agcaaaattt aaagaaaaag taatttgtgc ctttctcaat 11160
attcctgtta ttgttcatgt attctaaaac tcactgttac tcacttagct tgcttttaat 11220
gtttttttaaa gtgaaaaatt gttcccaagt acataaaatc tctacactca agaacaattc 11280
tagtcaaaag catttagagc ttccgtatga acacttaaag agtttttatt tgtaagagtc 11340
gcatcccaac tcttagcctg ttcttttctc acatgcagaa aaataggaaa gagacttcgt 11400
ttccacagtc tgcaaattcc tgtgtttaag aaccacagtg aataatccac ctccctgccc 11460
aactcatcgt actgtcatat agttttcctg acagtttgtg tattttctgt ctttcccacc 11520
cttaaattta gttttatgac ttcaaccata cttcttagga gtggaaaggt atctgtagta 11580
gattatggtt tattccacat aatcttgggg aataaaactt taaaaaagta tacagtttat 11640
acttctggtt acattacttc cttaaccaaa agtctaacca agaaatttga atctttaaaa 11700
aaaaaagagg ccgggcgcgg tggctcacgc ctgtaatccc agcactttgg gaggccgaga 11760
cgggcggatc acgaggtcag gagatcgaga ccatcctggc tgacacggtg aaaccccgtc 11820
tctactaaaa atacaaaaat tagccgggcg tggtggcgcg cgcctgtagt cccagctact 11880
cgggaggctg aggcaggaga atggcgtgaa cccgggaggc ggagcttgca gtgagtcgag 11940
atcgcgccac tgcgctccag cctgggcgac agagcgagac tccgtctcaa aaaaaaaaaa 12000
aaaaaaaaga gcctaatttt gcttcactgt ctgtgaaaag aattatctgt atcttttgca 12060
tgtaagacaa atctcaatga aaagggtgct taaatagaag ttaacactat tttaaagcaa 12120
gaatggaagt ggtttcatca tgcgtaaaca acaactctcc acattttgta atgattgatc 12180
tggatgcaat ttgtcatcag acaggagaag tcgaaagcaa agaaataaca ctgggagata 12240
gagaagctct ttcattcaat gcgaaaggtc aaaggcacat cagtttcttt aataatgcaa 12300
acctcagcac acattatcag tgtcctcatt attattgcct tgtttatttc ccactgctca 12360
ttgataattt caacgtgaaa tttacctgta ttgctgcatg catcttgcag tttaagaagt 12420
gaagtaaccc aatttcaaag ctagtgcttt agggaaaata ttggattgta tttacttcaa 12480
gcagagttcg ataatttatg tacataataa aaattttaaa tcccttagtt aatatagcag 12540

-continued ttgccaaaac tgggctatta tcattctaaa ctaccaaccc aaatggtagt gggtatctaa 12600
tctacctcta gaaagaaaat ggactgtatt tgctctatgt atttttcttg tacagcttgc 12660
catcgagaca tttataaagg agttgatatg agaggagtca attttaatgt gtctaaggtt 12720
agcagtgttg aagaatgcca aaaaaggtgc accagtaaca ttcgctgcca gtttttttca 12780
tatgccacgc aaacatttca caaggcagag taccggtgag tacaattcaa ggtgtgtgtt 12840
ctttgtattg gtgcctccag gatttcactg tattcttctt aacctctttt gttcccaaac 12900
taaaaaccaa acagggcttt tattctaacc actttcctca tttacttact ctattttatt 12960
tttttatctt ttatttattt atttatttat tgagatggag tcgcgctctg tcgcccaggc 13020
tagagtgcag tggcgtaatc tcgactcact acaacctccg cttcccgggt tcaagcgatt 13080
ctcctgcctc agcctcccga gtagctggga ttacaggcgt ccgccaccat gcctggctaa 13140
tttttgtatt tttagtagag tcggggtttt actatgttgg tcaggctggt ctcgaactcc 13200
tgatcttgtg atccacccac ctcagcctcc caaagcgctg ggattacagg catgagccac 13260
tgcgcctcgc ccttcatttt ttaattaaat aattcattta atttcatttg tttctctact 13320
cttttcccct ggcatgtaat tgtaccgcat cttcaaagcc tgacatcctc ttcccctact 13380
tctccaaagc tgattcttgc aggtctttcc tcaaataccg tcccctccaa aagcccattt 13440
ctgagcattc tcttttaagt cacactcagc tctgtttatt tcattcatag agctaatcac 13500
aatttgatat taacttgtga ttttttttcct tatttttaaa tcttattttt atttgcatag 13560
atgtatgggg tacaagtgta attttgttac tttgatgtat tttacagtgg taaagtctgg 13620
gcttttggta tatccatcac tggagtcatg tacattgtac ccactaagct atttttcaac 13680
gcccgccccc ttcccacctc tctgtcacct tcccagtctc tactgtctat cgctccatgc 13740
tctactcaat tttggtgtca ttttttcctg aagcaaaatt ttggtgtcat tttttctgaa 13800
gtcattttct gaagtctgtg tcatttttcg ctttcctgaa gcgaattttg gtgtcatttt 13860
tcctgaagtt ccgtttgccc cacacatagg ccttgcttat agaatgaggg tttagtgtca 13920
cggagtctcc tgcctcattc tcaccctaac ttttccttta ccccttttgcg aggggaagga 13980 tgtccattag gttaataatg cagacccccta acccactcat tatcagggtc attgtttttc 14040
cactgtgcat tttaatacta actgttacct gcactgctcc ctgcccctca aagtgcagaa 14100
agcaaagtaa cctcttttct tcccattcag gaacaattgc ctattaaagt acagtcccgg 14160
aggaacacct accgctataa aggtgctgag taacgtggaa tctggattct cactgaagcc 14220
ctgtgccctt tcagaaattg gtaattgtag gactacttca ctttgtgatt gtggtaggtg 14280
gaataggagc cccccagagac gtccctgtgc tgagccctgg gacctgtgcg tgtgttccca 14340
tagctggcaa aagcgtttct gtcaatggca tgcagttacg ggcttcgaga tggggagttt 14400
actctggatt ttctgaatgg gcccaatgta ctcacagggt tgagtgctca caaggctcat 14460
aagaaaaaga gagaggcgga aggctcagag ccagagagag aggtttgaag gtattacact 14520
gctggctttg aagatgaagg tccgtgagcc aaggaatgca ggcggcctct agaagttgaa 14580
aagggcgagg aaagagtttc cctgtggagc gtcctggagg aagaagccct gctgatgtct 14640
tgattttagc ccagtaagac ccaatctcta gaacagtaag ataattaatt tgtgttgttt 14700
ttaaccacta agtttgtggt tatgccccta gagcagcagt tataggaaac tagtacagtg 14760
atactgttag agttatagga cagtgatata ggacagtgat actgttatag ttataggaaa 14820
ctagtacagt gatactgtta gagttatagg acagtgatat aggacagtga tattgttata 14880

-continued

```
gttataggaa actagtacag tgatactgtt agagttatag gtacagtgat attgttatag  14940
ttataggaaa ctagtacagt gatactgtta caggtacagt gatataggac agtgatactg  15000
ttataggaaa ctagtacagt gatactgtta gagttatagg tacagtgaca taggacagtg  15060
atactgttat agttatagga aactagtaca gtgatactgt tagagttata ggtagagtga  15120
tataggacag tgatactgtt atagttatag aaaactagta cagtgatact gttatagtta  15180
taggacagtg atataggaca gtgatattgt tatagttata ggaaactagt acagtgatac  15240
tgttagagtt ataggtacag tgatatagga cagtgatatt gttatagtta taggaaacta  15300
gtacagtgat actgttagag ttataggtac agtgatattg ttatagttat aggaaactag  15360
tacagtgata ctgttatagg tacagtgata taggacagtg atactgttat aggaaactag  15420
tacagtgata ctgttagagt tataggtaca gtgacatagg acagtgatac tgttatagtt  15480
ataggaaact agtacagtga tactgttaga gttataggta cagtgatata ggacagtgat  15540
actgttatag ttataggaaa ctagtacagt gatactgtta tagttatagg acagtgatat  15600
tgttatagtt ataggaaact agtacagtga tactgttaga gttataggta cagtgatata  15660
ggacagtgat attgttatag ttataggaaa ctagtacagt gatactgtta tagttatagg  15720
acagtgatat aggacagtga tattgttata gttataggaa actagtacgg tgatactgtt  15780
atagttatag gtacagtgat attgttatag ttataggaaa ctagtacagt gatactgtta  15840
gagttatagg tacagtgata taggacagtg atattgttat agttatagga aactagtaca  15900
gtgatactgt tatagttgta ggacagtgat attgttatag ttataggaaa ctagtacagt  15960
gatactgtta gagttatagg tacagtgata taggacagtg atactgttat agttatagga  16020
cagtgatatt cttatagtta ccgtggtata gttatagtta aaggtacagt gatattgtta  16080
tagttatagg acagtgatat tgttatagtt ataggacagt gatgtagtta cagtgatata  16140
ggtacagtga tattgttata gttataggac agtgatatag ttataggaca gtgatattgt  16200
tacagttata ggtacagtga cgttgtaata gttataggac agtgatattg ttatagttat  16260
aggtacagtg atgttgtagc aaaactgtaa ggtcattcct tggttgtgtc cctatctagt  16320
gaaatgactc taccaggggt agggaaataa aactctgtcg tttcacacat aaaggtaatt  16380
tcaatggaat tatccagaaa attgccatga cattccacct catttagcat gtcaggatgt  16440
taatgacaag atgttactaa aagcaaatcc cttacggcca gttttccgca gtactgggtg  16500
ctggctctgt gcctggccct gtattgggtg ctgggctagg atttccctgt ggaagattgg  16560
gaaggttggt tacaaggtgg ctattttcct gtctcctctt tgcgacagca caccttctcc  16620
atggtgtgtg ccaggttcac gtgtactggt gatttaattt taacgttcat attatttttt  16680
tctgggagag tttttgaagg ctgccaggag gcaggactcg atgcaaacat gctccattct  16740
gtacccagcc ctgttgctgg aaggatttgc tgcacttacc cagggaacag gcaagctcgt  16800
gctgtggctc tgggctgtca cagctgctgt ccacacctgg gagagcaccc tggatggctc  16860
atctgtgtac ttgctttctt gttaaattgc agtgagttca catgtgattt aatcggatca  16920
aatggccttt acagactgat aaaaatatgg ctgtttcagg tggtgttttg agctgctaag  16980
ggcgtggctt ttcactgagt acgtggtccc cgttcctcag ggaacaccca gtagccacat  17040
gcctcctaaa cctagagtag ggctgtctcc tggcctaact gcccaaatga gattcataag  17100
ttagggatga tctgtagtta tcactacaga tttgtccttg gtttcaccaa ggattttcct  17160
aattttacaa acaaaacccc taaggctcct ggaaggaggg tagaagtgaa ggtgctccgg  17220
gggcaacaca gctgatgagc tgaaccagaa ctcgaccctt gggtcacaca catttcacag  17280
```

-continued

```
tgctcactcc accttttgtt tttttaatgg atttaatggt gttttaaagc ctcctgcctc  17340
tcaacacata tgaattcatt atatttacag atttccttct cttgtggtcc atcttcctgc  17400
atagatcttg agagatgtca ggctaaccac gtttcctcag ttaatttaac aaaaccattt  17460
gcaactctga catggaaaat tcctaccatg tgacttatta atttatcaat tgagatggta  17520
cacatatttt caagccaaaa ggaggaaaac ataaattgga aaaaaaaggt ttttttattt  17580
ttatcacctc tggggaagaa agtctgataa acgaagctgg ttgataaaat tgcaattagg  17640
ggaagcaaca tcatggtttc tgttcggagg ctaaccagat ggcatacttg aaatagagaa  17700
tgtcctagaa atcaactggt tgcttggcca aaatatctat aaatagtgcc caacatatta  17760
gataggaaaa gcaaagtaaa aacaatttta acaggttagg acattgggct gaagtattgc  17820
atatatttaa tgtcatgtgc gtccgtgtga agagaccact aaacaggctt tgtgtgagca  17880
agaaagcttt ttaatcacct gggtgcaggc aggctgagtc cgaaaagaga gtcagtgaag  17940
ggagatgggg tggggacgtt ttataggatt tgggtaggta gtggaaaatt acagtcaaag  18000
ggggttgttc tctggcgggc agcggtgggg ggtcacaagg tgctcagtgg gggagcttct  18060
gagccaggag aaggaatttc acaaggtaac gtcatcagtt aaggcaggaa ccggccattt  18120
tcacttcttt tgtctttctt cagttacttc aggtcatcta gatgtatacg tgcaggcctg  18180
ggcccagagg cctgacattc ctgtcttctt atattaataa gaaaaagaaa acgaaatagt  18240
ggtaaagtgt tggggtggcg aaagtttttg ggggtggtat ggagagataa tgggcgatgt  18300
ttctcagggc tgcttcgagc gggattaggg gcggcgtggg aacctacagt gggagagatg  18360
aagctgaagg aatattttat ggtaaggggt gatattgtgg ggttgttaga agcagcattt  18420
gtcatataga atgattggtg atggcctgga tatggttttg tgtgaaatga gaaactaaat  18480
ggaagacaca aggtctgaat aagagaagga gaaaaacagg tgttaaagga ctaagaattg  18540
ggaggaccca ggacatctaa ttagagagtg cctaaggggg ttcagtgtaa ttacttgctt  18600
ggttggtgag tttttgggct ctatccttga cagagtcctc ctttttaagt tggaggctga  18660
gcttggtgag gtgtgttttt aaaagaccat tagtctgttc tacctttcct gaagattgag  18720
gatggtgagg ggtatgaagg ttttactgaa taccaagagc ctgagaaact gcttgggtga  18780
tttgactaat aaaggccggt ctgttatcgg attgtataga gatggaaagg ccaaactgag  18840
gaattatgtc tgacagaagg gaagaaatga ccacggtggc cttctcagac cctgtgggaa  18900
aggcctctac ccatccagtg aaagtgtcta cccagaccaa gaggtatttt agtttcctga  18960
ctccgggtat gtgagtaaag tcaatctgcc agtcctgggc gggggcaaat ccccgagctt  19020
gatgtgtagg gaagggaggg ggcctgagca atccctgagg aggagtggag tagcagatgg  19080
aacactgagc agttattttt tgaggataga tttttacgac ggaaaggaaa agtgaggttt  19140
taagaggtgg gttagtggct tgtaacttac atggaagagt ttatgaaatg atgacagaat  19200
agaatgggcc tgtgaggctg gaggagatat tttccttggt ccaagaatta tttgccttgt  19260
gtgggaagag attgataggt ggaagtttca atgggggagt agatgggagt gacagatgag  19320
gaagaaaaaa actggctgtg agggatagaa gttggaatgc tcgctgcttt tttagctacc  19380
ttatcagcat aggcattgtc ctgagcagtg ggatctgatg ccttttggtg gcccttgcag  19440
tgaatggctt cagcttcctt tggaagtaaa gtggccttga gaggagtttt tattaaagag  19500
gcattaagat ggagaaccct tgtgtagtga ggaaacctcc ttcagcccat ataaccgcat  19560
ggtggtgcag aatatggaag gcatatttag agtcagtata aatattgaca cgtagtccct  19620
```

-continued ttgcaagagt gagggcctga gttaaggcaa tgagttcagc ttgctgagag gtagtggagc 19680
ggggcagagc agtagcctca gtgatagatg tggaagatac tacagcatag cctgcctttg 19740
ctggtgagtg gtgattaggc ctggtggaac tgccatcaat aaaccaagtg tgatcagggt 19800
aaggaacagg aaagaaggaa atatggggaa atggagtgga tgtcaggtgg atcagagaga 19860
tacagtcatg gggggtgggg ccagcctaaa acagtaaggt caagttgttt gaacagaaag 19920
gctacagggc gtggtcctgg ctcttgtgta agaattttga ctgcgcagcc ctgcacttcg 19980
gctgtgtgta atgaaaaggg ttgggatgag ttagggagag ctagtgtggg agcagtttct 20040
agggctgttt ttaaggaatg gcaagaggag tggctaaagg atttaggatc tttggggtca 20100
gctagctttg cttttgtgag tttatataat ggtttagtca ggatggtaaa acttagtatc 20160
caaaggcgga agtacttaac catacctagg aagaaaagga gttgttttgt agaaggggtt 20220
ggggtttggg agatgagcca gacacaatca gcagggagag cacatgtgtt ttcatgaaga 20280
attatgccga gataggtaat ggatgaggaa gaaatttggg cttgactgaa gtaatggggg 20340
ctgtcctcga agccttgtgg cagtacagcc caagtaagtt gctgaggctg acgggtgtca 20400
gggtcagtcc aagtgaaagc gaagagaggc tgggatgaag ggtgcaaagg aatagtaaag 20460
aaagcatgtt tgagatccag aacagaataa tgggttgtgg agggaggtat tgaggatagg 20520
agagtatatg gctttggtac catggggtga ataggcaaga caatttggtt aatgaggcac 20580
agatcctgaa ctaacctgta aggcttgtcc ggtttttgga caggtaaaat gggggaattg 20640
taaggagagt ttataggctt caaaaggcca cgctgtaaca ggtgagtgat aacaggcttt 20700
aatcctttta aagcatgctg tgggatggga tattggcatt gagcggggta agtgtgatta 20760
ggttttaatg ggatggtaag gggtgcacga taggttgcca aggagggagc agaggtgtcc 20820
tatacttgtg gattaaggtg gggacacaca aggggaggat gtgaaggagg ctttgaactg 20880
gggaaagggt ggcattgagg tgtggctgtg gcctaagaac agtcagggaa gcggataatt 20940
gagttaaaat gcctcgacct agtaagggag ctgggcaggt ggtgataact aaaaaggagt 21000
gcataaaaga atgttgtcca agttggcacc agagttgggg agttttaaga ggtttagaag 21060
cctggcggtc aatacctaca acagttatgg aggcaaggga aacaggccct tgaaaagaac 21120
gtaatgtgga gtgggtagcc tctgtattaa ttaagaaggg gatggattta ccctccactg 21180
taagagttac ctaaagcatc tgtgatggtc caggaggctt ctaaggtgat cgggcagcgt 21240
cagtcttcag ccgctaagcc aagaagatct gggaagcagt cagtcagaga gccttgggcc 21300
agagttccag gggctctggg agtggcagcc aggccagtta gacagtccga tttctagtgg 21360
ggtcccacac agatgagaca cagcttagga ggaatcccag gctgcgggca ttccttggcc 21420
cattggccag atttctggca cttgaaacaa gatcctgatg gaggaggtcc tgtaggaatg 21480
cttgaccact gcagtttagg cattttgaag tttttgtgtg tgctggagat gtggctgggt 21540
tttgtctcac agcagaggca aggaatcgca actcagaaat acattgctac ttggctgcct 21600
ctattattgt acatcttgaa ggcgaggtta attaagtcct cttgtggggt ttgagggctg 21660
gaatctaatt tttggagttt ttttttgttt gtttttttggt ttttttttt taatgtcagg 21720
agctgactgg gtgataaaat gcatattgag aataagaggc cttctgaccc ttctgggtct 21780
agggctgtaa agcgtctcag ggttgctgcc aaacgggcca tgaactgggc tgggtttttc 21840
atatttgatg aaaaagagcc taaacgctaa ctgatttggg agaggtcgga taaataaaaa 21900
ggaacattaa tcttgactat gcctttagct ccaaccacct ctttaagagg aaattgttgg 21960
gcaggtgggg gagggctagt cgtggaatga aactgtaagc tggaccgggt gtgaggaggg 22020
gaggtgatag aaggattata gggtggagga gcagaggctg aggaagaatt gggatctggc 22080
ttggcctggc aaggagcagc ctggggagga ggggagaggt cagatgggtc catagaaaag 22140
gaggattgga aagactcagc aacacttggg gttgggattg agaggacaga tgggttggga 22200
ttgaggggac agatgggagg gaaagaagga agatttggga caagttgcat tgggaacaga 22260
gactagggag ggaccaatgt gtaaaagaat gcctggacgt caggcacctc agaccgtttg 22320
cccattttat gacaagaatt atctagatct tgtaggatgg aaaaatcgaa agtgccgttt 22380
tctggctatt tggaaccatt gtcgagtttg tattggggtt aagcagcatt gcagaagaaa 22440
ataaggcatt taggttttag gtcaggtgtg agttgaagag gttttaagtt cttgagaaca 22500
taggctaagg gagaagaagg aggaatggag ggtggaaagt tgcctatagt gaaggaggca 22560
agcccagaga aaagagaggg tagagacatg gagagaaggg gtgggggggt gcttgccccc 22620
aggaaagtgg ttcttgccac taagggtgaa ggatcaaggc aggcattcgc gcggtgatca 22680
gatacctctg aaacgtgggt gaataatcaa gcaggtgtcc ctgcagtgat taaacagcaa 22740
ggaaagacta tcttcccaag tccatgacca gtgccagagt tttgggttca tggataaaac 22800
gcgtctcctc tgtctctacc agaaaatgaa aggaattgaa attaagagaa gggagagatt 22860
gaaggatggc gccaagattg aaaggaaaaa gaggttgagg gatagggaga gaggttggat 22920
aagagagtaa aaagaggctg cttacccaat ttaaaatcgg tgagatgttc cttgggcttg 22980
ttggtctgag gaccagaggt catgggtgga tctttctcat ggagcaaaga gcagggggac 23040
aggggattga tttcccaagg gaggtcccct gatctgagtc acagcaccaa atatcacgtg 23100
tgtccatgcg aagagaccac caaacaggct ttgtgtgagc aagaaagctt tttaatcacc 23160
tgggtgcagg cgggctgagt ccaaaaagag agtcagtgaa gggagatagg ggtggggacg 23220
ttttatagga tttgggtagg tagtggaaaa ttacagtcaa aggggggtgt tctctggcgg 23280
gcaggggtgg ggggtcacaa ggtgctcagt gggggagctt ctgagccagg agaaggaatt 23340
tcacaaggta acgtcatcag ttaaggcagg aaccggccat tttcacttct tttgtcattc 23400
ttcagttact tcaggccatc tggatgtatg catgtaggct tgggcccaga ggcctgacat 23460
ttaacatgga taaatgtaaa gttcttagaa tcatacatac actttggaaa agatggggct 23520
taatcgcact ttataagact tgaaggatgt ttgagaatca ctatgaaact gctgaaaata 23580
ccaagaaaat ttaattctta tgtatataaa taatgtgtct gttttacatg aatcccttct 23640
acaagcttgg tatttaatat ggcatatatt gttttttcat agtagattta aaatttttga 23700
tatctaattt agataacata aaattaaccc tttgaaagtg tacaactccg tggtttttag 23760
tatatccacc tgattgcaca acgatcacca ctgtctagtt ccagaacatt tttatcacca 23820
caaaagaaag gctgtatcca ggccgggcac ggtggctcac gcctgtaatc ccagcacttt 23880
gggaggccga ggcgggcgga tcacggggtc aggagattga aaccatcctg ggtaacacgg 23940
tgaagcccta tctgtactaa agatacaaaa aaattagctg ggcatgatgg cagatgcctg 24000
tagtcccagc tactcaggag gctgaggcag gagaatggcc tgaacccagg aagcggagct 24060
tgcagtgagc caagattgcg ccactgcact ccagcctggg cgacagagca agactccatc 24120
tcacaaaaaa ataataaaaa taaaataaaa aaaaaaaaga aaggctgtct ttctcctttc 24180
ccattggccg tctttctcca ttccctactc ctccaatccc ctggcaacca ctaaatctac 24240
tttccatgtc tgtggacttg actcttcggg acattttaca taaatggaat catgcaatgc 24300
agcacatttt gcatctggct tttttcacct ggcgtgtttt caaggctcat tcgtattcta 24360

```
gcatatatca atactttgtt cctatttagg actaaataag attctattgt atgaataaaa  24420
catattttgt ttatatactt agtttgatga acatttgagt tgtttctgga ttttttttt  24480
ttttttttg cctcttatga ataatgctgc tatggacaac agtttttggg taggcatgca  24540
ttttaaattc tcttatgtat atacttagga ttaaaattgc tggatcacag agtaactcca  24600
tgtttaactt tttgatgaat tgccaaactg tttttgagag cagctacaca atgttacatt  24660
cttaccagca acaattgagg gcttcagtct ctctacaacc ttaacaacac ttgttattgt  24720
ctttgtaatt attgcctttc taggcagtgt gaagtggtgt ctcactgtgg ttttgatatg  24780
catttcccta atgactaaca atgttgtgta tcttttcgtg tgctcatttt caatttgaat  24840
acattctttg ggaaaatctc tgtttaaatc ttttggccat taaaaataat tgggttattt  24900
tcattgttga gttgtatgaa ctctttatat actctggata ctacactctt atgacatata  24960
ttattttcaa aaattttctg tgcatctgca ggtcatcttt tcactttact gatggtgttc  25020
tttgaagcac caaagttttt aaacttgatg aaatccagtc tggctttatt cttgcacgtg  25080
ctttacctaa aacgccaaaa cctaattcat ggtttgaag attttgctt atgatttgtt  25140
cttagaggtt tatagtttta gctcttacat ttaggcattt gatgcatttt aaattaaatt  25200
ttgtatatgg tgtaaagtag caatccaact taattcttgc atgtgggtat tcagttattc  25260
cattgtcttg aaaccctttt caaaatcaat tgtctataaa tgtaagagtt tatttttgga  25320
ccatcagttc tatcctgttg acctatatat gcctatccta atgccagtta cacacagtct  25380
tgattaccat aactttgcag taagttttga actcagacag tctgagtgct tttattttgt  25440
ccttttcaa gattaatttg gttattccgg atcttttgca tttccatatg aattttagga  25500
tggttgtcaa tttctgcaat agaaaagcag caggattttg atagagagtg cattgaatct  25560
gtagaccaat gagtatcaat ggaattatgt gttatcaaat ttagtaaact acataaacga  25620
tatgtacaca actaaaacaa aactaagata taagatcata ttaatgtaat gataataaaa  25680
gtggattgtc tcctgttcta attttaatag gcacaaggca tttttgttaa tcacttctta  25740
ttaaagaatt ttttataata ttcaggaaaa tacaacaaaa aaaccttac attcctaagg  25800
cctcagagtc agagtaatat aaaggaaatg taaacacatg ctgagtaatg caagcatttg  25860
gcaatggtgg tgactggagc tgggagcaca gcttttattt ctctgaaata ggaatttgcc  25920
ccttagagtt agaccaattt tgccttcctc taaatggcaa acagtttgga gatactttaa  25980
aggacatttt ttcacttagg atgtttagta ctatgaataa taaatagtca caatttcctt  26040
aactatggtg acaaaataca agcaaattta gcctcatgtc atttcctaag gaacatcttc  26100
tctctgtgag ttcacaggtt gccacatgaa catcttccag catcttgcgt tctcagatgt  26160
ggatgttgcc agggttctca ctccagatgc ttttgtgtgt cggaccatct gcacctatca  26220
ccccaactgc ctcttcttta cattctatac aaatgtatgg aaaatcgagt cacaaaggcg  26280
agtatgcatg gaaaatcgca tcacaaaggc gagtatgcat ggggagcact tgctgctgta  26340
ctttcatcac ttttatagtc tgagttctta aaagtttcgt tcatttccct caaaacactt  26400
gaacctgcag tttcagtagg tactgttctg ccaggtgcag attagttaag agattagcag  26460
acttctctgc ctatcttctc ttactttaaa acaaatgtta ccattgaatc aaggaagcaa  26520
tagccatgag aaaaaagaag gatctgacgc ctttgaatga agattcaaaa catgatcttc  26580
atgttttgta ttagcttgga gtaaaatcca cttgctggca atatagccct taagcttgtt  26640
gcctcttctc tttgtttcag aaactagagc cctgtttatt ctgatcaagg ctctggccca  26700
ctgtctttat ctcagataac ccaccctctt ctgcacacag catggagcta agagaagggt  26760
```

-continued

```
gtctagttat gtaatatcat cggcagcata aattcccaga atttgttctt tgattttttt  26820
gtttgttttt ccagttagaa ggtggaactt catcattgtc ctcttttcag gttgtctgtg  26880
cctattagtt ttctccagag ggagaggtgg cttgatttac atttaatctc tgcaatttat  26940
tagagtcctg tagttggatt tactttgaag agagtttccc agaagaataa aatttgctgc  27000
gttgcttttt gggtgtgagc tgcttttgta tttgcctaat gcctttaatg caaatttctt  27060
tctttctctc ttgctttttt ttaaaaaaaa tagaaatgtt tgtcttctta aaacatctga  27120
aagtggcaca ccaagttcct ctactcctca agaaaacacc atatctggat atagcctttt  27180
aacctgcaaa agaactttac ctggtaatgt gatttgataa taatattaca taaaatgtaa  27240
cctatttcat gacttttaac agcaacagtg atgaaacaat cctcaaggta acagaaactt  27300
gtgtaaatgt cgttcattgc ttttcccatc tgatatcttt ttgtgtttat aattgacaca  27360
gaaccctgcc attctaaaat ttacccggga gttgactttg gaggagaaga attgaatgtg  27420
acttttgtta aaggagtgaa tgtttgccaa gagacttgca caaagatgat tcgctgtcag  27480
tttttcactt attctttact cccagaagac tgtaaggaag agaagtaaag gaaattttat  27540
ttttcaaaga cagttgacat gaccatttca tattctcttt cccccctgtga aggcttactc  27600
tttctactgt tcatttcatc taggtgtaag tgtttcttaa gattatctat ggatggttct  27660
ccaactagga ttgcgtatgg gacacaaggg agctctggtt actctttgag attgtgtaac  27720
actggggaca actctggtga gtaacctcac tttttcgtgg acctgtcagg gatgtctgtc  27780
atgttgatag tttgcttagt cttaaggaat tatgtgtctt gttctccttg gttagaaggg  27840
actttgattc acttctaatt ccaaccatta gcgtcaacgc tctcttttca gtctgcacaa  27900
caaaaacaag cacacgcatt gttggaggaa caaactcttc ttggggagag tggccctggc  27960
aggtgagcct gcaggtgaag ctgacagctc agaggcacct gtgtggaggg tcactcatag  28020
gacaccagtg ggtcctcact gctgcccact gctttgatgg gtaagtgttg gatgcatctc  28080
atccagagtc ttatcttggc ttttcatttt gaaggatcta tgatcagctg cttcaccgcc  28140
atgtgacttt atgaatagag acgtgttaaa gcggggatgg tattcacaac atttaactta  28200
tagggtccaa gcactgacca acctgaccat tagaacagag tgtggtctct gtacagggca  28260
gatggcgctg agtgggtatt ctccacagaa agagaaacga agacagtacc ccactcctcc  28320
aacccaccac ccaccaccaa tcccaccacc aattccacca ccaatcctgc cacccaccac  28380
caatctcacc accaatccca ccaccaatcc taccacccac catcaatctc agcaccaatc  28440
ccaccaccaa tcccaccacc aatcccacca cctaccccac caccaatccc gccacccacg  28500
accaatccca ccaccgatcc cgccaccaat cccaccacca atcccaccac ctaccccacc  28560
accaatcccg ccacccacga ccaatcccac caccgatccc gccaccaacc accaatccca  28620
ccaccaatcc caccaccaat ccctgatgtg ttcttcaaag acttatttgt caggcccata  28680
gaaatgttac ttcttgctct ttgattcata aatatactaa gtcataataa tttttaaaag  28740
tgagagtttc gtactctgta tatttcaatg tatataattt gatctatttc aatttattgg  28800
tcaaatagta gacatgttag gtaagtctta aaatactgag gctttggagt tagacagaac  28860
atggcttaag tgacagcttt gctgcttatt agaggtgtgg ccctagaaga tttgtaaatc  28920
cctctgagct ttatttgatc taaaatatga atagtaatag tcccgaattt gtaacgttgt  28980
tgggaagatt aagtgacaca tttaaaatgc ttagtactgt gtgtagaaca taaacacttc  29040
aaaaaatgta aactgtgatt tctatattca ataagaaatg tagaaatgga caaagcatat  29100
```

-continued

```
aaaaagcaaa agaaatacta gaagacactt gatttttctc aaaaataaac acaccaagta  29160
tttttgtttt agtgaaattc atgcttacat gctgtatact aggattgaac atactgccac  29220
caaaatatag cagtcggtgg tacatgtggg tggagcaaga cccctccacc ttgtcatcgt  29280
gtgaaggggc tctgccatac atgaccttgc atgtgacttt aaggtggttg gcctggaaga  29340
aaagtcccaa gatgggaaat agtaggtgtc tttttttacta aatgcactcc aatttgggac  29400
caaaaatttt cattcttgaa ggctcagtat tgtgagttta taagagataa tagacataaa  29460
agtgtaatga tttcattgca aataaaaaaa ggcccctttg cacctgatat ctccatcatt  29520
tttctagaat tttgtgcaca catgccttgc actacttggt gatgataaag atttccagat  29580
ctttgcacag aataaggctt tgctttagat cagaattttg gatgtactta gtatacattc  29640
atcttttaaa taatctattt acattttcat actttccaaa atacagatat attttatttt  29700
atttatatat ttatttaatt tattttttga gatggagtct ctctctgttg cccagagtag  29760
agtgcagtgg cacaatcttg gttcactgca gcctctgcct cccgggttca agcgattctc  29820
ctgcctcagc ctcctgagta gctgggatta caggcgcgcg ccacacctgg ctaatttttg  29880
tatttttagt agagacgagg tttcatcatg ttggtcaggc tggtctcgaa ctcctggcct  29940
caagggatcc acccacctcg gcctcccgaa gtgctgggat tacaggtgtg ggccactgtg  30000
cccagctgta tagagatatt ttaaacaaca ctaaagtcct cctactttga ctaattagaa  30060
gagcattaga agatcagcct gacttcttga cagttctgaa tttagtggag caatgaggtt  30120
cagctttggt gaatgagctt aatttttcca tgataaactg ctagtttctt cccactacag  30180
tgtctctcaa aaatgggaca gcaacattct ttttgttttc acttgcagta agcatgatgc  30240
aattacataa atgtacactt ttcaatttgt taaatagaat cttcagagat tcactactgc  30300
cgctattggt gatgaaaaat taccagaagg aggaattagg taggagaaaa tgtgtcctat  30360
gtatttcctt cccagttctt tgaaagagag tgataggaaa aaggaacact attgaaggaa  30420
ggactgccca gtttcaaaca ggtatttatt tttctctcct aggcttcccc tgcaggatgt  30480
ttggcgcatc tatagtggca ttttaaatct gtcagacatt acaaaagata cacctttctc  30540
acaaataaaa gagattatta ttcaccaaaa ctataaagtc tcagaaggga atcatgatat  30600
cgccttgata aaactccagg ctcctttgaa ttacactggt atgtagcata tgtaagaagg  30660
tggagagcag aattgcgctg gttgatattt tcatatcagt ttgaacaaga gggcagacct  30720
agagagactg tcgtcgtttt ctgactggtg gagttgaggg aaacgtgagg gttgctggga  30780
agtgaagacc ccgcgacttg ccgtgaaatc tcttctactt aaagagcaag acatgtgaat  30840
taattctttc agggagggat acaactgcat gcaggtgatg gaaataatgg gcgtgggaaa  30900
tgtctgtgcc gtctgagagg cactgggctt gctttgacaa gagtagcaga actgtcattg  30960
ctttgggctt agggatattc gaatgtgtga gggcaagtgg gatcagatat ctacttccag  31020
gtataatttg ggtaggaaag agactcatgc agaaagaagc cctggaaggc cagagcatcg  31080
tggtcagagg tgttgccttt ggagggtcat tgctgccagg agccgaatac ccactgtatc  31140
caataacatt catggtcagg aatggtggct cacacctgta atcccaacac tttgggatgc  31200
ccaggtggga ggattgcttg aggccaggag tttgagacca gcctgggcaa cacagtgaga  31260
ccccgtctct acataaaatt agaaaaaaac aattaactgg gtgtggtggt gtgcacctgt  31320
agtcccagct agtcaagagg ctgagacaag aggatctctt gagcccagga gctcaaggct  31380
gtagtgagcc aagatcgtgc cactgcacac aaacaattat gtgacctcgg gcaagttgct  31440
ttacctcttt acacctctta atttccttat ctgtaaaatg aggatgataa tttcttcctg  31500
```

-continued

```
ggtctgttgt aataattaat acatcaaagc acttcatgtc tggaacagtg aagataccct  31560
gctatgacta ttaaggatag tatacatgga ataagacaca ggaacttcta aatgcttttg  31620
accatagatt taggttctga gttttaagaa tttaactcag gaaattgtaa caccaaaaat  31680
gtcatgtgaa aaatggtggt gacaaatttt cttgaatcat tagccttaga ggttgggcag  31740
aaagcaaaaa attattcttg atgctactct atagaaagag aagacagaaa aagagaaaga  31800
tgtattttta aagtctatat ccataacttt atttgaccaa actctaattt aaaaattatg  31860
tttcagaatt ccaaaaacca atatgcctac cttccaaagg tgacacaagc acaatttata  31920
ccaactgttg ggtaaccgga tggggcttct cgaaggagaa aggtaagcat gacgctttaa  31980
atattgcttc tagagtaagt ctcacatgtt gaaatacatg gagtgggtcg ttttaatcgg  32040
tttctgtctg aaattatatc taaactcttt atctttccta tctatttatt cccaaatatt  32100
tattcagtta ttcttaaaaa atgtattttt gctttggctt gaaaaaaaat tttagggaga  32160
cttttaagca tcttacttca ttataaagat cagttgcttg actttgcatg aagcagattg  32220
ggcccttcta gggctgacaa gcccgtgcaa gaccacccgc tcctcagtgt tagtagcgtt  32280
cccgtctccc aaaaccatgt tctcccttga tgctaatggc cgggagcaca ggcaggtgtg  32340
tcgtctcact atggagaata atatttgtgt cattctttac agaagaaggt agcttgccaa  32400
actgtctcca tctttcccga ttcagtcttt tgttcaagta attcacattt ttagattttt  32460
tattggtaat ctgagacaag aagaaattta aagtaatctt cactaagcca tgaaagctcc  32520
caacattgtt ctccatgaga gatgctggcc tgcatttatt caaaaacaaa agacccctct  32580
gttgccaaag ctcggagggc ttttcagaaa cgatatagtt gtaaattata attttgaata  32640
tataaagcaa aaaaatgaaa agtgagaact tccaggcttt ggattgttgt aggtgataaa  32700
tataaaatgg gatttctggg gggctgctac tgagatgagg ggatggcaga aaacatggaa  32760
gcaaggtctc tggtcagccc agggtgctgg gcttgtccca acaccacgta ggcaataaga  32820
ggacagtaca gggtgccgtc tctctccctc ttcctctctc tgtctctctc tctctgtgtg  32880
tgtgtgtgtg tgtgtgtgta acactacctt cccaattttt actgtctatt tgtattcaaa  32940
gataaggtcc ttatgaaaaa tacactgctc tgattcactt taaaacttat ttccatattt  33000
attatttatt gtgggaataa taatattccc aatattatta tttattattt aagttattat  33060
tattaacttc cctctgaggt tatatattgg ttactcacag gtgaaatcca aaatattcta  33120
caaaaggtaa atattccttt ggtaacaaat gaagaatgcc agaaaagata tcaagattat  33180
aaaataaccc aacggatggt ctgtgctggc tataaagaag ggggaaaaga tgcttgtaag  33240
gtaactcatg agattatgaa aaacacaata ggctgcttga gaaaattcat ttcaaaatat  33300
attttccaat agcataattc aatcatagtt tttaaaaaaa ttcagagaca aatgatctga  33360
taaattgata agcaactttt aacaaattga atatacataa tatatattta tattatttat  33420
gatatatgtc acaatctatg catgtgctat ttaagagggg caaatataca tgcaataatt  33480
gtgctagaat ataaaaacat tagacttcat cattgggatg atgatatcaa gatttctttg  33540
ttagatttat ttcagataga aaaggggata cgaaaaatgc aggcacatga gatacttgga  33600
gaactttaag aaagagtgag tgtgtgtgtg tgtgtgtgtg tgtgtgtgtg tgtgtctggc  33660
aagcaaggtc ttgcacacac acagcacttt gggaggccaa tgcaggtgga tcacttgagc  33720
ctaggaattt gagaccagtc tgggcaatgt gatgaaaccc atctctacaa aaaaatatga  33780
aagtatctgt gtgtgtgtgt tgctgtgtag tggactacag aactttagag gcagtcactt  33840
```

-continued atttgaatcc cattgtcgta actttctact attttatttt tccactgtga ctcagggaga 33900
ttcaggtggt cccttagttt gcaaacacaa tggaatgtgg cgtttggtgg gcatcaccag 33960
ctggggtgaa ggctgtgccc gcagggagca acctggtgtc tacaccaaag tcgctgagta 34020
catggactgg attttagaga aaacacagag cagtgatgga aaagctcaga tgcagtcacc 34080
agcatgagaa gcagtccaga gtctaggcaa tttttacaac ctgagttcaa gtcaaattct 34140
gagcctgggg ggtcctcatc tgcaaagcat ggagagtggc atcttctttg catcctaagg 34200
acgaaaaaca cagtgcactc agagctgctg aggacaatgt ctggctgaag cccgctttca 34260
gcacgccgta accaggggct gacaatgcga ggtcgcaact gagatctcca tgactgtgtg 34320
ttgtgaaata aaatggtgaa agatcacgat tagcaagtgt tttcttctgg ttgtgaaaca 34380
gaactgaaag taagtggttg aggttccagc acagttcctg ggatccctct aattgcactg 34440
cttcctctgg aactcagtat atctcaaaga tgtaatttcc tctccgtgct gcacctggtc 34500
ggccactgaa acccactatt gcctgcttca cgtgtggcaa agagctagcg ggcttgggtt 34560
ttgttctgcc gagaggaagg gagaacaccc acttttataa gaaagagatg ggttacctga 34620
acccatgggc acctttgcct cttggcctcc taactttgct accagggcat ggctaggagg 34680
gtccaggctg cgcgtgctga ggagctcgag gggctgcagc attgcacagc cttcatggca 34740
ggcaaggaat ctgctttgca aggggcatta gccctggagg ctcagtggat atgggctatt 34800
gcaatagtaa ttcaaggagc atttttaggc ctggcgtggt ggctcacgcc tgtaattcca 34860
acagtttagg agatcaaggc aggtggatca cttgagcata ggagttcgag actagcctgg 34920
ccaatgtgac gaaaccccat ctccacaaaa attagctggg catggtggtg cgcacctgta 34980
atcccagctc ccccagaagc tgaggcagga ggaccgcttg agcccgggga tgtcgtggct 35040
gcagtgagct gagatggcac cactgcatca ctgcattcca gcctgggcaa cagagtgaga 35100
ctgtctcaaa aaaaggaagc attgttaggt ataaattatt attattatta ttattagtag 35160
tagtagtagt agtagtagta ctgagacgga gtcttgctct gttgcccagg ctggagtgca 35220
gtggtgcaat cttggctcac tgcaatctct gcctcccggg ttcacgccat tctcctgcct 35280
cagcctccgg agtagctggg actacaggca cccgccactg tgcttggcta attttttgta 35340
tttttagtag agacgggttt caccatgtta gccagaatgg tctcgatctg ctgaccttgt 35400
gatccacccg cctcggcctc ccaaagtgct gggattacag gcttgagcca ccacacccag 35460
ccctgttagg tataaattat ttcataaaat tcagacttgt aaatttatgg tagcctttgg 35520
aatgggtgat agatgtccta tgccacacaa attcctcaca tgccgaggct caccgtaact 35580
gataccagct cgcttgattc agttcagtta aactgaacaa catttacaca gaattggcga 35640
tttacaaaat cttatgtaag ttaagtagaa aaacagaaaa aagttttctg aaagagtttg 35700
ggtttttcct tcaatgctca agacagaggt ccccaacctt tttggcacca gggaccagtt 35760
ttgtggaaga cagtttttcc atggaccagc atggtggtgg gggatgattc tggaatgatt 35820
caagtgcatg acatttatta tgcactttat ttctattatt actacattgt aatatataat 35880
gaaataatta tgcaactcac cataatgtag aatcagtggg agctctgagc ttgttttcct 35940
gcaactagac agtcccatct gagggtgatg ggagacagtg acagatcatc aggcattaga 36000
ttctcataag gagcctagat ccctcacatg tgcagttcat aacagggttt gagctcctat 36060
gagagtctca tgctgctgcg gatctggcag gaggcagagc tcaggcggtt atgcttgctg 36120
gcctgccact cacctcctgc tgtgcggcct ggctgctaac aggccatgga ccaggtactg 36180
ttctgggccc cgggggttgg gaacccctgc tcagagacac accgggtggt aggaggagct 36240

-continued

```
aaaggtggag agggtgaagg aaaatatgag gtctgggcta tccacaaacc agatagcagg  36300

aaactgaaga gttaaacatt tacttcagaa ttgaatggct tttgtaaaat ctggctagat  36360

tccatgaaac gattttaaaa atgcactatt taaattttgc ctttgcatgc gatgaagaca  36420

ttagtctttg ttcatgtgga tgttttttta tgtttaaaag ggaaaaaatg gtttgcaatg  36480

aaacttttat ctcagtcttt gagtattgat catggggtgt tggaacagga ctttggaatg  36540

cttgcagggt aaacctttgg cctctgttag tcagggaatg acctagtttg gcaaaacaga  36600

ggagagtttt gaaatatgga actttcccga ggcatacatt gtcattttaa agtggtcaat  36660

caaagcccag taggactggg ctggtgtctt ggtgactcac tgtgtgctca tatacagggg  36720

taactgagga gcccttcaca caggtctagc ctcgtgggac taaaaagtgt gacatgggct  36780

aggaaaatgc gaggctggga tgccttcact cccatgagga agcgtgacgg gaggaggcgt  36840

gggccactgg cagttctact tcacaaaggc tgctggcagt gtcaatcctg caagctggcc  36900

ttgccctcct gtggcggcag tgtacacgtg gcatgcaagc acatgcacaa gccacctggc  36960

tccaaggtca gccaagggct ccaacatctg tctcagtccc                        37000


<210> SEQ ID NO 11
<211> LENGTH: 2472
<212> TYPE: DNA
<213> ORGANISM: Mus musculus
<220> FEATURE:
<221> NAME/KEY: CDS
<222> LOCATION: (96)..(2012)

<400> SEQUENCE: 11

agaccgccct cggtgccata ttcagagggc ttgaagacca tcttcatgtg aagactccct     60

ctcctccaga accacaacgt gaccatcctt ccagg atg att tta ttc aac cga       113
                                       Met Ile Leu Phe Asn Arg
                                       1               5

gtg ggt tat ttt gtt tcc ttg ttt gct acc gtc tcc tgt ggg tgt atg      161
Val Gly Tyr Phe Val Ser Leu Phe Ala Thr Val Ser Cys Gly Cys Met
            10                  15                  20

act caa ctg tat aaa aat acc ttc ttc aga ggt ggg gat cta gct gcc      209
Thr Gln Leu Tyr Lys Asn Thr Phe Phe Arg Gly Gly Asp Leu Ala Ala
        25                  30                  35

atc tac acc cca gat gcc cag tac tgt cag aag atg tgc act ttt cac      257
Ile Tyr Thr Pro Asp Ala Gln Tyr Cys Gln Lys Met Cys Thr Phe His
    40                  45                  50

ccc agg tgc ctg ctg ttc agc ttt ctc gcc gtg act cca ccc aaa gag      305
Pro Arg Cys Leu Leu Phe Ser Phe Leu Ala Val Thr Pro Pro Lys Glu
55                  60                  65                  70

aca aat aaa cgg ttt ggt tgc ttc atg aaa gag agc att aca ggg act      353
Thr Asn Lys Arg Phe Gly Cys Phe Met Lys Glu Ser Ile Thr Gly Thr
                75                  80                  85

ttg cca aga ata cac cgg aca ggg gcc att tct ggt cat tct tta aag      401
Leu Pro Arg Ile His Arg Thr Gly Ala Ile Ser Gly His Ser Leu Lys
            90                  95                  100

cag tgt ggc cat caa ata agt gct tgc cac cga gac ata tac aaa gga      449
Gln Cys Gly His Gln Ile Ser Ala Cys His Arg Asp Ile Tyr Lys Gly
        105                 110                 115

ctt gat atg aga ggg tcc aac ttt aat atc tct aag acc gac aat att      497
Leu Asp Met Arg Gly Ser Asn Phe Asn Ile Ser Lys Thr Asp Asn Ile
    120                 125                 130

gaa gaa tgc cag aaa ctg tgc aca aat aat ttt cac tgc caa ttt ttc      545
Glu Glu Cys Gln Lys Leu Cys Thr Asn Asn Phe His Cys Gln Phe Phe
135                 140                 145                 150
```

```
aca tat gct aca agt gca ttt tac aga cca gag tac cgg aag aag tgc      593
Thr Tyr Ala Thr Ser Ala Phe Tyr Arg Pro Glu Tyr Arg Lys Lys Cys
                155                 160                 165

ctg ctg aag cac agt gca agc gga aca ccc acc agc ata aag tca gcg      641
Leu Leu Lys His Ser Ala Ser Gly Thr Pro Thr Ser Ile Lys Ser Ala
            170                 175                 180

gac aac ctg gtg tct gga ttc tca ctg aag tcc tgt gcg ctt tcg gag      689
Asp Asn Leu Val Ser Gly Phe Ser Leu Lys Ser Cys Ala Leu Ser Glu
        185                 190                 195

ata ggt tgc ccc atg gat att ttc cag cac tct gcc ttt gca gac ctg      737
Ile Gly Cys Pro Met Asp Ile Phe Gln His Ser Ala Phe Ala Asp Leu
    200                 205                 210

aat gta agc cag gtc atc acc ccc gat gcc ttt gtg tgt cgc acc atc      785
Asn Val Ser Gln Val Ile Thr Pro Asp Ala Phe Val Cys Arg Thr Ile
215                 220                 225                 230

tgc acc ttc cat ccc aac tgc ctt ttc ttc acg ttc tac acg aat gaa      833
Cys Thr Phe His Pro Asn Cys Leu Phe Phe Thr Phe Tyr Thr Asn Glu
                235                 240                 245

tgg gag aca gaa tca cag aga aat gtt tgt ttt ctt aag acg tct aaa      881
Trp Glu Thr Glu Ser Gln Arg Asn Val Cys Phe Leu Lys Thr Ser Lys
            250                 255                 260

agt gga aga cca agt ccc cct att cct caa gaa aac gct ata tct gga      929
Ser Gly Arg Pro Ser Pro Pro Ile Pro Gln Glu Asn Ala Ile Ser Gly
        265                 270                 275

tat agt ctc ctc acc tgc aga aaa act cgc cct gaa ccc tgc cat tcc      977
Tyr Ser Leu Leu Thr Cys Arg Lys Thr Arg Pro Glu Pro Cys His Ser
    280                 285                 290

aaa att tac tct gga gtt gac ttt gaa ggg gaa gaa ctg aat gtg acc     1025
Lys Ile Tyr Ser Gly Val Asp Phe Glu Gly Glu Glu Leu Asn Val Thr
295                 300                 305                 310

ttc gtg caa gga gca gat gtc tgc caa gag act tgt aca aag aca atc     1073
Phe Val Gln Gly Ala Asp Val Cys Gln Glu Thr Cys Thr Lys Thr Ile
                315                 320                 325

cgc tgc cag ttt ttt att tac tcc tta ctc ccc caa gac tgc aag gag     1121
Arg Cys Gln Phe Phe Ile Tyr Ser Leu Leu Pro Gln Asp Cys Lys Glu
            330                 335                 340

gag ggg tgt aaa tgt tcc tta agg tta tcc aca gat ggc tcc cca act     1169
Glu Gly Cys Lys Cys Ser Leu Arg Leu Ser Thr Asp Gly Ser Pro Thr
        345                 350                 355

agg atc acc tat ggc atg cag ggg agc tcc ggt tat tct ctg aga ttg     1217
Arg Ile Thr Tyr Gly Met Gln Gly Ser Ser Gly Tyr Ser Leu Arg Leu
    360                 365                 370

tgt aaa ctt gtg gac agc cct gac tgt aca aca aaa ata aat gca cgt     1265
Cys Lys Leu Val Asp Ser Pro Asp Cys Thr Thr Lys Ile Asn Ala Arg
375                 380                 385                 390

att gtg gga gga aca aac gct tct tta ggg gag tgg cca tgg cag gtc     1313
Ile Val Gly Gly Thr Asn Ala Ser Leu Gly Glu Trp Pro Trp Gln Val
                395                 400                 405

agc ctg caa gtg aag ctg gta tct cag acc cat ttg tgt gga ggg tcc     1361
Ser Leu Gln Val Lys Leu Val Ser Gln Thr His Leu Cys Gly Gly Ser
            410                 415                 420

atc att ggt cgc caa tgg gta ctg aca gct gcc cat tgc ttt gat gga     1409
Ile Ile Gly Arg Gln Trp Val Leu Thr Ala Ala His Cys Phe Asp Gly
        425                 430                 435

att ccc tat cca gat gtg tgg cgt ata tat ggc gga att ctt agt ctg     1457
Ile Pro Tyr Pro Asp Val Trp Arg Ile Tyr Gly Gly Ile Leu Ser Leu
    440                 445                 450

tcc gag att acg aaa gaa acg cct tcc tcg aga ata aag gag ctt att     1505
Ser Glu Ile Thr Lys Glu Thr Pro Ser Ser Arg Ile Lys Glu Leu Ile
```

-continued

```
455                 460                 465                 470

att cat cag gaa tac aaa gtc tca gaa ggc aat tat gat att gcc tta     1553
Ile His Gln Glu Tyr Lys Val Ser Glu Gly Asn Tyr Asp Ile Ala Leu
                475                 480                 485

ata aag ctt cag acg ccc ctg aat tat act gaa ttc caa aaa cca ata     1601
Ile Lys Leu Gln Thr Pro Leu Asn Tyr Thr Glu Phe Gln Lys Pro Ile
            490                 495                 500

tgc ctg cct tcc aaa gct gac aca aat aca att tat acc aac tgt tgg     1649
Cys Leu Pro Ser Lys Ala Asp Thr Asn Thr Ile Tyr Thr Asn Cys Trp
        505                 510                 515

gtg act gga tgg ggc tac acg aag gaa caa ggt gaa acg caa aat att     1697
Val Thr Gly Trp Gly Tyr Thr Lys Glu Gln Gly Glu Thr Gln Asn Ile
    520                 525                 530

cta caa aag gct act att cct ttg gta cca aat gaa gaa tgc cag aaa     1745
Leu Gln Lys Ala Thr Ile Pro Leu Val Pro Asn Glu Glu Cys Gln Lys
535                 540                 545                 550

aaa tac aga gat tat gtt ata aac aag cag atg atc tgt gct ggc tac     1793
Lys Tyr Arg Asp Tyr Val Ile Asn Lys Gln Met Ile Cys Ala Gly Tyr
                555                 560                 565

aaa gaa ggc gga aca gac gct tgt aag gga gat tcc ggt ggc ccc tta     1841
Lys Glu Gly Gly Thr Asp Ala Cys Lys Gly Asp Ser Gly Gly Pro Leu
            570                 575                 580

gtc tgt aaa cac agt gga cgg tgg cag ttg gtg ggt atc acc agc tgg     1889
Val Cys Lys His Ser Gly Arg Trp Gln Leu Val Gly Ile Thr Ser Trp
        585                 590                 595

ggt gaa ggc tgc gcc cgc aag gac caa cca gga gtc tac acc aaa gtt     1937
Gly Glu Gly Cys Ala Arg Lys Asp Gln Pro Gly Val Tyr Thr Lys Val
    600                 605                 610

tct gag tac atg gac tgg ata ttg gag aag aca cag agc agt gat gta     1985
Ser Glu Tyr Met Asp Trp Ile Leu Glu Lys Thr Gln Ser Ser Asp Val
615                 620                 625                 630

aga gct ctg gag aca tct tca gcc tga ggaggctggg taccaaggag           2032
Arg Ala Leu Glu Thr Ser Ser Ala
                635

gaagaaccca gctggcttta ccacctgccc tcaaggcaaa ctagagctcc aggattctcg   2092

gctgtaaaat gttgataatg gtgtctacct cacatccgta tcattggatt gaaaattcaa   2152

gtgtagatat agttgctgaa gacagcgttt tgctcaagtg tgtttcctgc cttgagtcac   2212

aggagctcca atgggagcat tacaaagatc accaagcttg ttaggaaaga gaatgatcaa   2272

agggttttat taggtaatga aatgtctaga tgtgatgcaa ttgaaaaaaa gaccccagat   2332

tctagcacag tccttgggac cattctcatg taactgttga ctctggacct cagcagatct   2392

cagagttacc tgtccacttc tgacatttgt ttattagagc ctgatgctat tctttcaagt   2452

ggagcaaaaa aaaaaaaaaa                                               2472


<210> SEQ ID NO 12
<211> LENGTH: 260
<212> TYPE: DNA
<213> ORGANISM: Mus musculus

<400> SEQUENCE: 12

gagtgtaaac actggagcca agcaaagacc gccctcggtg ccatattcag aggggttgaa     60

gaacatcttc atgtgaagaa tccctctcct ccagaagcac aacgtgacca tccttccagg    120

atgaatttat tcgaccgagt gggttatttt gtttccttgt ttggtactgt ctcctgtggg    180

tgtatgagtg gactgttaaa taatacctct gcagaggtgg ggatctagtt ggcatctaga    240

cccctgagga cgagtagtga                                                260
```

<210> SEQ ID NO 13
<211> LENGTH: 30000
<212> TYPE: DNA
<213> ORGANISM: Mus musculus

<400> SEQUENCE: 13
atgagaagtt attttaaatt taattttta aagtttattt attcacccct tgccacgctc 60
tccagtcgag tcagtttgac aagcagaagc ttggaagctg gccgtgagga aaagagtttc 120
atggaagctc cctcctggag tctggcactc tctttaatct ctttaaccca tacattaatt 180
ttccactccc atgttagtct agtgtatgga tccacgtgcc ctctattaag cattacccta 240
ttataagtgc catttaagat tgaattctga catagctaaa gcctctccca gtgttccaag 300
atcccagttt acagcaaggt agtttaacct attcagtaac taattaagca ttacaataga 360
cagagccatt aactcagttg tctgcagaaa gagcctggga atctcactga gatagaaatc 420
tttactacag gctacattcc atgccaagag caagttgata tactatactg atatatgggg 480
aattcttcag acaagataag attttacaag acctaggaat ttaggggtcc atgacactac 540
attattcttg aggcctgtca agagttaaaa ccccctggtg ctattaacac taaagtgtga 600
aactcttgcc tggcattagc ctgatcctag gcagggctgg taatttctat tgtaaacatt 660
tatctagttc ctgcaaattc ctttcttgct tgtatctggt aaatttcagt gtaccttgtc 720
ttattgtgat ttgtagctcc tgataattcg ttgtaatata aaatagtcta atgttcgacc 780
agagattaca ttcagattca acacctctct tgtgtgcatc tgtttgtcaa tttaatccta 840
agctttgccc acctactcta gagacccgtt ctacacagac acagggaccc agagggtctg 900
cagcaacctc ttgcatggtt atgtgtgcac acacagaaga agtataggtg tggtggtcaa 960
aggacacttt taggggggttg ccttactccc tccactgtgc aggttctggg gatagaactc 1020
cagtcattag gcttgacagt aaatgccttt gaccccctga gatatcctgc aagctccacc 1080
atgattttag gctttaaaaa catgcaaacc tattagtcat ttatctcttc aatagattct 1140
gggttagcca actgtgcagt tagagttgaa tgtgcaaggc tgtttgaatc tcgggtccat 1200
agaaaatagc ctggcatcag ggtccattgc aattacattg atgattgagt ccctgggctc 1260
atgcttggat acccagttca atggggccag tatcttatga tcgaggactg gcttaaagtg 1320
cagatgttga aatgagccta gaaactgagc ctccagaggc aatgtccaaa ctcaagccca 1380
cgggcatgag tttgttccca aatctacaat tacagtcctg gaaaagattc tacgggggta 1440
gtagacccgg tgactgggcc tgaggttaac atcctggagc ctgggtctgc agggtctggc 1500
cggatactgg aatttcctgg gatgggcttg ttttcagacc cgtgaaaagt aatgtttaca 1560
tcactcttct tcatgcattt ggaacacatc tccttgctgc gctgcttagg attggtagga 1620
gggtttcacg gttaatgtga aaagtctaac attcctcaat gcatattcac taggtccaca 1680
ttttcaaccg gggttggggg gtgcaaccta tcatctggat tccttaacaa ctcggaaggc 1740
attttttttt gtgcacagag aattgttccc atggattctt ctgcaaaggg acccattttg 1800
gagcctccag ctctgtcatc gtgtttatat gacttcttga aattggtaac atattaagta 1860
gctgaacctg gactgggatg tccgtggact atattgacag gttaaacagt tgaaactgat 1920
gccagaaacc cagtgtaaac actggagcca agcaaagacc gccctcggtg ccatattcag 1980
agggcttgaa gaccatcttc atgtgaagac tccctctcct ccagaaccac aacgtgacca 2040
tccttccagg tagctgcttt ctaccggtct tgttatttcc tgtgtcttgg gtttttttt 2100

-continued

```
ttcaatataa ctatttctgc atgaacaaaa gctcactggt ataatgcact aatttcctga   2160
gtttttagaa aatctacaag gagttgtttt tctttctata caaatatatt aatgtaaaat   2220
attttaaaac caagaataag tttttgattc ttttcaaaga tgtcctttct gtgaaggttg   2280
tgggtgatat tattgtcctt attcataata attttgcatt aatctggaaa tttaataagt   2340
gtttttaatt atttgtatta actctttaca aaattattag aaataaatct tcaaaattaa   2400
caataaatac actaatacac actgatagta atctagaggt ctcaatttgg atcttgggaa   2460
gcatgataaa tattttaatt ttctatatac aaaatatccc acagccaaat cttccttctc   2520
ctggtgatta tgtgctgtga tttgcaactt agacatttat caaaaaggtg aagtctacat   2580
gaagttaaat tgtctattaa atacatggta aacatgatct caacctagta gttatatgta   2640
tattttttc tttcaaagga tgattttatt caaccgagtg ggttattttg tttccttgtt   2700
tgctaccgtc tcctgtggta agtattagtt taaggagttc aaattaatag tgtgtgagag   2760
aggaatggtc ttgcaatcta taccactcct ggaggaagcc tttaactgta cagctttggg   2820
ggacaaggca gctgttgata ctccaaggca agaacttaga tacattaccc caaacacaga   2880
tgaacagggg gaggaactta gagacatcac tgcacctgtt agcagaaata tctgttttga   2940
gtttactctt taacagagcc tctcccaccc ccgcagagtt gtttgtcttt ataatatcag   3000
ccttctaaat aaaaactcta cctgaaaatt ggaaataata tcagatattg cataatgatt   3060
tgagtctaat ccaggtatct gattagtata tagtattttt aatataagac atacagagcc   3120
atttctaaac tgaaagtacc tgctttgggt ttcacaagta tagtatccct ttggcagtct   3180
ggagggacag ctttcaacac tcgatgtcag tgctctttcc ctgtttattc ctttgctttt   3240
caggatatga gcatggatgg ccctgaacag cccctctcaa cagtcattat agagggagat   3300
ttccctgggt ataacatgtc aggtgtattc tgagtcaaag ctgacttaga tatagccaca   3360
cgcaaggatt gttttcttct tctttttttt tttttttttt ttttttggt tttttggttt   3420
tttggttttt caagacaggg tttctctgtg tagccctggc tgtcctggaa ctcactctgt   3480
agaccaggct ggcctcgaac tcagaaatcc acctgcctct acctcctgag tgctgggatt   3540
aaaggcgtgt gccaccacgc ctggcaagga ttgttttctt gactttcaag tatatggcaa   3600
agataggctt gtccttgtaa gtagaagtca tttctctagg taagctcttt tttcccatcc   3660
ctctctgctc cctacatctg gcccatcatc tgtaactgct ctcctgtacc ataactactg   3720
ccatgttcaa accaactaaa cacgaatagt gataaccaga gatgctatgg gccatggcta   3780
taaaattcat aatcatgaca ggaaaatgag acatgggaat acatataata cttgaaaaca   3840
aatactttat ataatcctaa agtacaaaat aatgatcgcc aattttttct ttagtctttc   3900
atatttttcc gcatgaatct atctgttgta taaagtgtta ttcatgaata ataattttaa   3960
ttaaaaatta tgaacactaa tgaaaaataa ttttaactta cctttggtat ttatagctaa   4020
tgttaatgca aatgaacatt tatgttattt gttcttcttc atggatattt tgtaagtatg   4080
gacattctct gcacatatcc aattatttct atagattaaa tttttggaaa taaagatttt   4140
agatagagga gtatgaatac ctttgaaggc tttatagcat gcattatggt attagcttct   4200
agacaggcat tctctgtttg gttttcccca caagcatgtg gaagtgaatt aacaatacaa   4260
tctcttagaa atgagatgtc aatattaaat acgttttatg ttaaaaaata aaatttacag   4320
gttcacaaca ctggtttaaa cagctaggtt aacaaagatt aaatttgaaa caatcaatat   4380
ttgtgcgctg gctttgatca caaatgaaag aaaatcaagc agtacagctt taatataaat   4440
gagtttaaga gttcagaaat ccatgtgccc agtgaatggc ttctggagta cttagacact   4500
```

-continued

```
gcccaatgat ggcacccgca catagtgtgt ctgcattgct ttactgcatt gtacgctgct   4560
gccttcatct caggatgcac aatagcaagg caggaccagc agcccaagtc gccttggaaa   4620
caaaagtaaa tcggagcctt ttcctaagtc tgagaacaag cctgttacag actagctctg   4680
gtcaggtcat tgtaccagct ctgtgtgcag ttctggctct ggtctgattg gctggagcat   4740
caacagcaga agcatcacct ccagcaacat atggaccacc acttgtagat ggttcctcag   4800
gaggaaatct ggatgccaat tcagcaaggt ggctctatgc caggctacaa agtaacagat   4860
gcctattgga gctcactgtt ctaagtgggc aggcatggtg caggaggagc tgagagttct   4920
acatcttcat caaaaggctg ctagcagaat actgagttcc aggcagatag gatgagggtc   4980
ttataggcca cacccacagt gacacaccta ctcctacaag cacacctact cccacagggc   5040
cacaccttct aatagtgtca ctccctgaga tgaacacata caaaccatca cagtgcccat   5100
ttgctgcaaa gagaggcttc gttgatgtgg gacagtcact acagttatct agggaaggtg   5160
gtcatctcac tgttagcagc tttcatatac ttacagttat ttacactcct ttggtaaatt   5220
atcttttcat atctgacatt gaatgtttaa aacattttag catttatcta tttttgtatc   5280
tatgtctgca cacgcatgtg cacatataca catgtgctgt ggagcacgtg tggagatgaa   5340
ggggcatctt gtggaggtca agaggtcaat ttgaaaactg aagggcctca ttacaggttg   5400
tttaggttaa ataaactctg tacaaataat gctgttgtta taatcattac caccaccttc   5460
gttatcattg ctgccgttat cattgcaact gaggaggata agcagtccca cagttagaat   5520
gtgtctagtc actctttttc attgcctgag tcacatgtta gtttaccaac attcaattgc   5580
aggatagaaa cttccaggct atcagcggat cacagtttgt gtttgtgttt gtgtacgtct   5640
ctgtgcaatg ggatggcaag ggagcctctg cttgataatt atgagatgct aaccacataa   5700
aaaaacaagt ctctttatag ctatcctcac cactgggcct actattcagt gcattgtgca   5760
aatgggacac cttagggtat acacttggga acatatattc ctaggagaat ttacccagga   5820
atatctgttc tttccaaata taaacctgac ttaagaggta ggcatggtga cacctctctg   5880
ataagaagaa aaacaatatt gctaggttgg ttcatccaaa cttgtctcag tggcaggatc   5940
cccatataga tagaacatag aaactcttac ctctttagtg cttattaaaa gacatgttgt   6000
ctagacaacc attccttgaa aagtaaggac aatgtgggca atgttgccac tggagtattc   6060
cataattaat gaaaacctga ctggtgaaaa cagacaggct gcctaaggtg gaaagctaag   6120
tacaaagatt tgaacggaat cttttcaggg agatcccagt tcttcaatgg atttaaagag   6180
ctgctctcta atgatatgtg gggtgcagga tacccacatg atggagtcag cagaagcgat   6240
gtatctcagt ttattttcaa gttagcttac tttaattttt tttttaattt gaaaggtatt   6300
agcctttttt tctgatttat tgaaaatatt cttttctcat gccatatatc ctgattatat   6360
attttccttc cctctactcc tccaagttcc tccccagctc ccatcttctc cccatccact   6420
ccctttctgc ctctcattag ataagaacaa ggtttctaag agacaacacc tatacagaac   6480
aacataaaat ataataagat gaagcaaaaa ccaccacagc aaagttggac aaggcaagtc   6540
aacagaagga gaagagcccc caagagaagg gacaagagtc agagacccat tcaggagtgc   6600
catgaaaatt ctcaggggaa ggctacaaaa tatacgtaga ggaccctgtg cagatctgtg   6660
taggccctgg tgcttcagtc tctgtttgct cacaggagcc ttacttagtt ggttcagagg   6720
accttgtttt cttggtgtcc tctggcccct ctagctctga gactccttct gtctcctctt   6780
tcacagggat ggatctctca gctctgagag gaaggatttg atgaagacat accactcaga   6840
```

-continued

```
gctgtgtgtc ctaaggactc tgactctccc ctctccgttc tcctctctct actcttctcc   6900
ctctctctcc cctcttctct ttcttctctc ctctctcatc tctcctccct cccctcccca   6960
ctctgtaaaa tgtctgagtg tgggtttctg caaatacatt ttctttatca agaaatgagc   7020
aacagaaaaa cagtacccaa tacttattat tttgcttaaa taaggctggc taaacatcaa   7080
catgcaacat tgcatgttag aaaaagggga cagacaggat tgagagtcag aaagagtaag   7140
tttatgtccc aggatatcta ttcactgtgt gatattagcc acatttgaac tctgagactc   7200
agttattgac ttctttcatg aaaaaagggg gaaaagagag gtgcaactaa tggtcctgac   7260
ctcaagttgc cctccaagtg ttgtcctaaa aagcattttg aaaaaaatgc tgtattttca   7320
tttctaaggt gagatgtttt cacagcatgt tagacagcag gcagaaaaaa attatactgt   7380
attttagtag ataatttatg taaaaattat tatataggta ataaaagagt caacttctat   7440
gcataaatgt tcataagatg actttaaata gcatgctgta ttgtttgaca gttgtcagac   7500
ccgtgaagtt gtaatgacta ttaggataaa taaaacagga atgtcaaaac agatgcattt   7560
ctattaaaat ggttacactt tcccccaaaa tcaactttta aatcacaggg tgtatgactc   7620
aactgtataa aaataccttc ttcagaggtg gggatctagc tgccatctac accccagatg   7680
cccagtactg tcagaagatg tgcacttttc accccaggtg cctgctgttc agctttctcg   7740
ccgtgactcc acccaaagag acaaataaac ggtaagatgt gatggtttgt cattgccagg   7800
ttagatgtta cttaaactgc ttccagttat atgccaaaat agtgccatgt ttctcagagt   7860
gttcaaagac tctttgcatc agaagctcct aggctgggtc ttttcaatgc agacccaaag   7920
tactgaaccc agagacagac tctaaacagc cacaacactt gttcacagtg ataggaggta   7980
gtgatgctac agccaaggcc tgaagacaga gcatgtgaca agaaagggtc cttcctcaca   8040
ctgcaatact tagccttttt tcactttcaa catgttattc tgtccccaca tgtacatctg   8100
ttatgtatat aaatgttatt agctgggtta tgcatatgag ggagaacctg agggtttttt   8160
ttctttctga gattatatgg cttcccttaa tattaaaaat actaagtcca tccattttcc   8220
tacaattttt gtgatttcat ttctcttcag cgcataatag cattgcatta catattttct   8280
gttttattca tttgtgtatt aattaattta ttataaatgc tgcaaataaa acaatcacag   8340
aaccaaatta accagactca gagactgtgc aactcagtga acttctatcc agttacagta   8400
attgtttgaa aaggaagcca gggaatgtca caatgcactt gatactttca ctatcaaatt   8460
tatattttaa tcatatatat tgctttctaa taaatggtga caatttcacc tgcatagaga   8520
aatatattta attgctttac tagctaccat atttataggg agcaaagttg agaaagtata   8580
agccaggaat tttgttgata ataaatttga gacccagtag gcaagtctca atagtgcctg   8640
cagtggacca gtttacactt ttagaatatg cattttctct ctctctctct ctctccctct   8700
ctctctctcc ctctctctct ctccctctct ctctctctct ctctctctct ctctctctgt   8760
gtgtgtgtgt gtgtgtgtgt gtgtgtgtat gtgtgtgtgt tttattaggt ggtaattttg   8820
gcaagaacaa ttattaaaaa tatatttgga aattttacct taattttctt tcatttgatc   8880
aagagccaaa tgtaaatttt tgcttctttt tccatacaca taactttcat cttcaactat   8940
gtgaatttaa gaattagaat tttaaaactc attctctgat ccctacatgc taatctgtac   9000
caaaaaaaac ccaaacaaac aaacaaacaa acaaaaaaac ccagaccata tgtgagattt   9060
acatttttaa aaaaattgaa ccaggttcta agattcttat aaatagcaac gttaacatag   9120
cgttgatatt gaagacagaa aaagcctccc attacatgga cactaccggg aatcaataca   9180
ccagatgaac atcacatgca gacctaactc atagctgagt cagttttttt aaaagtaaat   9240
```

```
taaaatcttt ataacaataa tcaccatttt agaaaatgtg gatgtttcag acaggagaat   9300
cgtaagttta aagtcagctt gtgtaagtta acaagatcct ttgtcaaagc aaactaagta   9360
aaagcttggg gtggcatggg gggaggaaaa ggctggtgat aattattagg atttgattag   9420
catatttgaa gcccaggctc tcctcctcag taccacataa actaagaaca aaaccaatga   9480
tcttttggaa agaggagcca gcgacgttca gaatgagaaa agaatcatca acccttcagt   9540
gtggttggct ctccgcactt gcagcgtaaa cagtaagaaa aacaacgcta tagagagcat   9600
ggacttgtcg caagaacgtt ctcttcagca agtgacaagg ccatgttatt agtttcctga   9660
ccctgggctt tatttattaa catgtacaaa atactgcatc atttcttaat gtgtgtttgt   9720
tcaattccgc ttttaaaatg tgttttttta aaaaacaggt ttggttgctt catgaaagag   9780
agcattacag ggactttgcc aagaatacac cggacagggg ccatttctgg tcattcttta   9840
aagcagtgtg gccatcaaat aagtggtaag atgtggattt tttttcccaa ctaaatttga   9900
gttaataaca ctcaaactca gagtagcttt tgctgcaagt ttatactatg atggactttt   9960
agacgagacc accaagaaag ataatagagc tgaggcagca tcatggctgt aagaaggggg  10020
tactttcacc ttgataatgt tcacatcttt atcagttata gtgctcagcc ttaacgggcc  10080
tctattacct atggtattca cacacaatgt aagatttgtg ggaaatgaat atgcacccag  10140
ataataggcc ttccctgttt ccgcaacaga ctttttaggt aagactcggg gacatctcat  10200
cccaaagtgg attttggggt aattggtggt cacccccaga actgactttg ccctctccat  10260
gtcaaagaac agctgaaaat gtctggagac agtttagatt gttaaaattg gggaaaatgg  10320
tactttacgg taatgctcag agttggtgca gtcagactca gcagaaaaca ttctggccac  10380
cacggggcca ttgataaggg attaagactg tggttctcag ccttcctaat gctgcagctc  10440
tttaatacag attctcttgt ggtggaggtt accagctata cacttttcat cgccacctca  10500
taactgtaat tttgctactc taataaatca tagttgtaaa catttgtgtt ttccaatggt  10560
cttaggcgac ccctgtgaaa gggtcttgca acccctccaa aatgggttgt gacccacggg  10620
ttgagcaatg ccggtttaag aaatcttatt tttgccactc ggtccagact gaaagactga  10680
gttctgtcca tcttgctaag cgtaatattt cttacaagga atgtgaacgc taggatgtta  10740
gagcgctttc tctgtgactg ctgttgcaac tgatgtctta gaacacacca tcttaattct  10800
cagaccatct taaaggctta ggataaagaa ggcattttta taagatgaca gggactgtta  10860
gaaagtgaaa gtgctaaaaa agaatgaggc ggtgagttcg attatattgc tttgttttta  10920
cgtccttcat tccgtaggtt caaatttcaa atgttctcat tttgctccag taataataac  10980
agccctctca ccacataaac attcagtgtc tgcagtttaa attttaggca atgaatgaag  11040
aatgacaatg gcttagctat aaatccatat atttatatgt acatatattt aacctgaagt  11100
gaactacatc aagatcaatc cataaactaa cttgctgtat attgcttgat gaagtgtcta  11160
attactgtga ccaacgacaa cattttaaaa aatagaacta ttgtgacttc cccaaagctg  11220
cttagttgtc tttttctccc cctaactttg taactttttt ccaaatactt tcaagaaaga  11280
tcttcaagtt aaaaagggat ctcaaggagc cagttttagt aaaaactatt gagaggtggg  11340
cttaaagtgt acagataatc attaagaaaa tattttattt gtttctacct tatcccaacc  11400
ctcagctcat ttcttttctt atctgaagca aatttaaaag aaccttattt ttacaattta  11460
cagtttccta ccctgtaaac tgctgggagt ttaggacccc tacaccctaa cataatgctt  11520
tccttttttt ttattggata gtttctttat ttacatttca aatgttataa cctttcctgg  11580
```

-continued

```
ttccctcccc caccccaagt cccctatccc atccccctct ctctgcttct attaggctac  11640
tcccccaccc acccacccac tcccgcctcc ccacccaggc attctcctac actggggcat  11700
caagccttca caggaccaaa ggcctttcct cccattgatg cctgacaagg ccatcctctg  11760
ctatatattc ggctagagcc atgggtccct ccatgtgtac tctttggttg gtgatttagt  11820
ccctgggagc tctggggggt ctggttggtt gatattgttg ttcttcctat ggggttgcaa  11880
acccccttcag ctcctttcta ttagtttgta tatgcatagt gtctcctgtg tttaattaat  11940
ttcacaattt ttagaaactt atagttatgt acaatagaat attgtttgtg ctaacacaca  12000
cacacacaca cacacacaca cacacactgc ttgcttaact aagtatctaa ttaaaacaaa  12060
acgtaagagc ttaatttggc ttaatttctg ttaaaagaat caactatttt caatatataa  12120
gataaattcc agtaaaagga tgcttaaata gaattgaaga aacctttaaa aactggtgtg  12180
ctagcacatg gctatcatct cagtaccagg gaagcagagg caaagaacat tttaagttca  12240
aagccagtct ggtctgaaat tcgagattgc cacattcagc atggcttggg ggctggaaaa  12300
ctgagtaaga acattaaggg aagaaaggac agacacacag acccatgtgc agggaagctg  12360
gaatagtgtg agttatgaga ctgaacccct aacccccaga atgcttgtta catacacagg  12420
ggaagggtta aatagtctca gagggcggtc aggcaatctc tcctcttggt ctataatcat  12480
cttggagtag aaggtgaagt tgctggtcat tgtgcacact ggtcaattgc tcctaaacac  12540
tactgctgag acccagggat atctctgccc ttttcccatg ggtctgagcc actgatcctt  12600
cacatgtggt cctcagacta cagaccacag acttcacctg ctcctttcac atttactggg  12660
gtttcccatg gttaccacag gagttccaaa ccagccaggc tagaaaggac aaggaaggat  12720
gcagtggctg cggtggtggc cagtggtggt ggtggtggtg gtcatagaac ttaagagagg  12780
tttaaagcaa gaagggaaat gatttcactg tgcgtataaa taaattgaga cagtctgtta  12840
aaagatttga cacaggcatc agtgttgtga ctaatagtca caaatagcaa tcagacctga  12900
ataggcgaag gaagagaaac tgatgcagat catgattttg ttttgttttg ttttttttggt  12960
tgtttgcatt gttggtggtg gttgttggtt tgggtttttt tttttgcgta tttgtttttt  13020
gttttgtttt tgacccagaa gtcaaaggtt cgccgtttgt caaatacttt gtgtctctgg  13080
cacacactat caggacccct gttgctgttg ccttccttgc ttatcagtgc ctctgctagc  13140
ttccatgtgg aagtgcattg ttttgtattg ttgcatactc gttgcagttt aagaggcaaa  13200
ataacctgtt tttaatgctg gggccaggta aacacacccg aggtgagcta atgtccagca  13260
gtgtttgata atttagacat gcaaaaaaca ttttaattcc tgtacttacc agggaagtca  13320
ccaaaatggg ataccaacct tcaaaaatga ctctgaggga agagcagttt atttgtgtct  13380
aaaaagaagt ttggtcgaac gtctctgtgt ttcctttcag cttgccaccg agacatatac  13440
aaaggacttg atatgagagg gtccaacttt aatatctcta agaccgacaa tattgaagaa  13500
tgccagaaac tgtgcacaaa taattttcac tgccaatttt tcacatatgc tacaagtgca  13560
ttttacagac cagagtaccg gtgagtgagg cacagatccg agaggacact ccagggatgt  13620
gttagcatga aaaaaaaaat cttccctcca gtcaaggtgc aaggggcatg caatccccag  13680
ccctgcccct attttattcc ttatttacat agttaatttc aatgtaattt cctcctaaag  13740
gtagcaaact ccctgtagtc aactgatagg ctgtgtatgg gcatagtgtc agacaatggt  13800
gtctgccact ccattcgcag aagggaaaag catctgttga ttgatgttgc ccaactgtgc  13860
ccctctgtgg ttatcaattc gataacgaat attatccgca cgtctttgtg cgccccaaca  13920
aaggaagcat aacaacatct tttgtgacat ccaggaagaa gtgcctgctg aagcacagtg  13980
```

```
caagcggaac acccaccagc ataaagtcag cggacaacct ggtgtctgga ttctcactga  14040
agtcctgtgc gctttcggag ataggtaact agatgacgat tattccactg tgattgcgat  14100
gccctaaaca agagtgccaa gaaataccca cgtgccattc ccagggacct ggggaatatg  14160
atgccttttt atagatgtga ttgcatggaa atacttggca atcggaatga tgttgggtta  14220
ccagaatatg cccctgccca ggctcaaggg ttcttatatg ataaagagag aaacagaggg  14280
gtcagtgtca gagtagaaag acttgaatgg tctatattgc tgcctttaaa gatggaagaa  14340
gagtccaaaa gcaaagggta gcagaaatta aaaagggcac agaacaggtc tccctgttaa  14400
ttatataaat atattatatt tatcttccaa aggactataa aggcagaaac cacaacatga  14460
taattttggg aagccaaatt cactcatatc ctatttgggt gtgggcaagg cttgattttg  14520
caatatacat ccagcaggtg cctcagtcgt ccaagcaagc aagcgtttca cacaaaatcg  14580
gaacttagca actagcctgt taaatctttg ccccgttacc ttgcaagaat agctgaggcc  14640
gtggcatatt ttgtaacact caggcaattt tattttttgc ccagctgtac caggaagtgg  14700
tccatcaatg gacagggtac attcaatgta agaacaactt cttcatggct tatatgagct  14760
taaaggaaca ttttgttttt acaagccgag cagagtaaac gtatcctcta attatattgt  14820
tcccaatcat cggaccttat gctgtgctgt agcgtggtag aaaatcacag gtcaatgtgc  14880
atgtgtggaa gatacagaga acaaacagag gccttggttt agagcaacct gcccttgtgg  14940
ggtaactgac ctagtccagt gagagcagga acaggtatta cccaattcac gtggaatgca  15000
acttcacgac tttgcactag gccatactgc caccttggga agcaagcgtc accaggattt  15060
ttgctgcggg caaagcacac tccagccaga acagcacact gctgcaaggg tgttttaaac  15120
acaggtttaa agacaaggtt tttttttgtt ttgtttttgt ttttttttt gtttttgttt  15180
tttttctgcc tcaagtgctg tccacagtct caacaagtga ggtctgctag cattctgtct  15240
aaactccacc cccacagtta cctggcaaca gccaggtagg ctccttcctc tcttaccctc  15300
ttgggctctc ccctactctc ccccccctccc tactcccttc cctcctctct ccacatgctc  15360
atggctagac tctacttctc tactctcttc ttctctctgc ctttctctgc ctctactact  15420
ctcttaactc tcccccccccc ccatgccctg aataaactct attctattct ataccttcta  15480
taccttcgtg tagctggtcc ccagggggaa aggctgcctt ggcatggacc tgcagagata  15540
tccccttccc ccacacttca ccataccccc atagaacata tcttaatatc tctatatctt  15600
ttttataatc acaacattgg ttaaaggctt gttttcagag tttaggcatg gactttgaaa  15660
gctttggaga taatcatagt tgccctgtta atggatcaat actatttaca attctaatta  15720
aaaggactcc tcttttcctg ttgtaggttt ggcatttgcc ctgatctgta ttttcatctt  15780
aggaggcaga tgtcatgtcc cataatcacc aggatccatt gcttctcccc accttcccct  15840
ctctcttttt cccctcctat ccctcctcct ttgtaccccg tctccttctc cctctccttc  15900
ccctccctct ctccccctcc tcctctcttc ctccccccttt cccccttccc ctctctcttc  15960
ctccccccttt ccctctctcc gtcccctcct cctccccctc cgtctctctt ttgtctttct  16020
ccctcctttc ttccttcttc ctctttctgt agacacatgc tctcaaggaa agggctggaa  16080
acactaggca aaacaggagt caggtctgat aaacttaagc cctgtgagca gaattttcca  16140
gggagcttct tgacaaaccg agtgatgatt gttgtctggg aacgagggac agtggctttg  16200
gaggtgctcc aaccattctg acatgttgat tttcagcaca tccatggggc tgttttccag  16260
gtctctatgg atctgagaaa ggggcacaaa tataaggcag ttcaacccca cacagctctt  16320
```

-continued

```
gctgaaggtc agccatttgt ttctatctca ggattagtct caattgtgtg tccctttggt  16380
taatttctag ggattaaaaa aaaagtgact tgactcattt tactagtatt taacatagtt  16440
ataaaagaag acgaatgcag gctggtggta acatttgcct ttaatcccag tgttcaggag  16500
gtaaaggctg agttcaaggc tagcccggtc tacagagtga gttccagaac aaccagggct  16560
acacagagaa agcctatatt gaaaacaaac aaacaaacaa acaaacaaga tggattctgg  16620
gcacttgtat tctctcagcc tcgctaacat tctgtaacac ttttaattaa cagagtgacc  16680
cacttagggt tattgttgtt gtgatgaaac accataacca aagcaactca gggaggaaag  16740
gtttagttca gtttatactt ctggataaca gtgaagaaag tccaggaggg tgggacctca  16800
aacagggcaa gaacacggag gcaggagctg atgcagaggg ggtggaagaa tgctgcttac  16860
tgccttgctc atcatggctt gctcagcctg ctttcttata gaacccagga ccaccagcct  16920
atggatggca ctacctacca tggactgggc ccaactctga tcactaatta agaaaatgcc  16980
ctataggctt gccttcagct ggatcctatg gaggcattga tgctccctct tctctgatga  17040
ctctagcttc tgtcaagttg acataaaacc agccaggtca tatagctaac aacctaacgt  17100
tggagtggaa aatgtctttg gaaagccaga tgctcatctt gcctgggtca ggttctgcat  17160
tttgtgtgga acaataggaa gctggagtat agccaactag ggcaaccatc ttgacggaat  17220
tcttagaagt aatggaaaat ttagaaacca gtaaaggaag atgttaagta tattcaactt  17280
gaacagaaga ctgccttggc gtttggcgaa gtctcctctg ttctgaaagg ctgtcattag  17340
ggactgggtc agtacacaat cccgtagggt tgttttagaa aggtaggact ttgtagaaag  17400
taatttttg aagtccctaa catcttcagc ggtccagaaa agaagttgac tttgtcacat  17460
ggtggtgaac tccttttcaa ctacaaatgt cccaggaaag ttgtaaagtg acatgccagg  17520
gatgtcttgg agatacagtt gtaggttggc atggttacct gaacattctc ttccagtagc  17580
aaggctcttc atgatttttt tttttaattc aagtggtaga atcagcttcc aagactacac  17640
aagtgggatg tgagctctct tgatccaact gtcttgagtt tgactggcct atcgttattc  17700
ttaagtgtcc attttattag tatggaatca aattgattct tacatgctat cgaattgagc  17760
aactcatgta aatagcataa ataaaaatag atgaaaaata aaatgatata aggggggatg  17820
aaaatgaagc ttttctgttc tcatcgaagg gcatgcttgt tagccctttg gaatttatgt  17880
taatgtcttt tcattaaaat gcttctcaca atactcagaa acaaagcatg aaacagcatg  17940
ttcccaaggc ttagtcataa tacaagggaa actcgagtca tctaatgtcc tattagaaat  18000
gacagtgctg cttattctac agcacccagt tgctgtcttt cccagtagaa caacttttac  18060
ttttttagca aagaacaaac tacaaattct gagataagtt aacaggcttt cctcctctta  18120
ttgaaatgga ttctctctct ctctctctct ctctctctct ctctctctct ctctctctct  18180
ctctcacaca cacacacaca cacacacaca cacacacaca caatatatcc tgatcccggt  18240
ttccactccc attactcctc ccacaacacc tcccctccat ttctatcatt agaaaagaaa  18300
caggcttcta agtaataaaa caaggcaaaa atgaaacaag aaaacaaaac cgaacacatt  18360
gaacttgaac aaattgaaga aacaaacgag agaaggcaca agattcagag agctacacac  18420
acgtccgcac actcaggaat ccccattaaa aatagtcaag tggaagctat acccagggga  18480
cctcttgcag accagtgcag ccccagtgca tgctgcctca gtctctcaac gggcagtttt  18540
taacacaggg tgctgattcc cgccaatatc aattgtcata atcaccttag ttactatgtt  18600
gaaacaaaca caagcaaact cgggcattgt gtcactgagg aatgttcacc gctgagttca  18660
caggttgccc catggatatt ttccagcact ctgcctttgc agacctgaat gtaagccagg  18720
```

-continued

```
tcatcacccc cgatgccttt gtgtgtcgca ccatctgcac cttccatccc aactgccttt  18780
tcttcacgtt ctacacgaat gaatgggaga cagaatcaca gaggtgagtg tgagcggcgt  18840
gcgccccctt ctagcccttt ccgttccttg cgagggtctt gctcgttgcc ctaacagcgc  18900
tggagcctgt ggtttaaccg gatgcttttc agccaggtgc aggttacttc acagattaac  18960
aaattcttcc cttccataaa acaagcctac tatttagtca aaccacagcg gcagaggcag  19020
aagggagcag gaagcattct cactggcatt aaggtttggg attggcttgg gttacagctg  19080
ctcatgcaaa ctgtccttta atcttgtgag aaaccagagc cctgcttatc cagatctagg  19140
gtctagtctg acctcttcat ctttacacag catttccttt atgtacgccg tggggcctgc  19200
agaaggatgt gtgtggacat aataccatgg gtagcataaa tccaaaccaa cagtcttttg  19260
atgccttctc tttttccttt ttctaattag aaggtggact ttaatcctct gtcctctttt  19320
ctggatgtct gtacctacca ggtatttttt gccagaggga gaggtgactc tacttacatt  19380
taagccctgt gatatttttg gagtcttgca gtctgactga ctgaaaataa tttctcagaa  19440
gaataccatt tatggagttg cttagagagg aaggaaggaa ggaaggaagg aaggaaggaa  19500
ggaaggaagg aaggaaggaa ggaaggaagg aaagaaggaa ggagagagag agagagagag  19560
agagagaaag agaaagagaa agaaagaaag aaagaaagaa agaaagaaag aaagaaagaa  19620
agaaagaaag aaaggaagga aggaaggtag gtctgtctag tgcttctaat gctgtcttct  19680
tcttctttct catttatttt taatagaaat gtttgttttc ttaagacgtc taaaagtgga  19740
agaccaagtc cccctattcc tcaagaaaac gctatatctg gatatagtct cctcacctgc  19800
agaaaaactc gccctggtaa tgactcaatc ttagtggcac atggcatgtg tccgggtttg  19860
gttcttggtt gcttgataaa tactatgacc aaaagcaagt tgggagagaa aggagtttgt  19920
tttgttcaca tgtcccagtc atagctgatt cctgagggaa gtcaggctag aaactcaagc  19980
agaagcagag gcagggactg ggcagagacc atggagaaat gttgcttctt agcttgcttc  20040
tgtgaatata tatatatata tatatatatt catgctacct gcccagaatt gacactgacc  20100
tggttagacg gaccctcttc catccatcat taatccaaag aacatcccac agacatgcct  20160
ataagttagt ctgaggaaga cgattctcag actgatggtc catcttttca ggtgactcta  20220
ttttgtatca agttgacaaa cactaacagc cacatggtgc agcacatctt ggggtcctct  20280
aagagttaat gaaatggttc tcacgactct agaaactttg ccaatgtgac tcgtttcctg  20340
acttgtgata tatcctttga tatttgtgta tggtgcagaa ccctgccatt ccaaaattta  20400
ctctggagtt gactttgaag gggaagaact gaatgtgacc ttcgtgcaag gagcagatgt  20460
ctgccaagag acttgtacaa agacaatccg ctgccagttt tttatttact ccttactccc  20520
ccaagactgc aaggaggagg ggtaaggaaa cctttctttg atgatcagca aggtaattgt  20580
tttctagttt tctccctgtg tgggggttta attttagact gttcatttat ttccaggtgt  20640
aaatgttcct taaggttatc cacagatggc tccccaacta ggatcaccta tggcatgcag  20700
gggagctccg gttattctct gagattgtgt aaacttgtgg acagccctgg tgagtgaggt  20760
tcgtttgtta cggaactgca tggctggctt ggctgttgtg attaatgtct tggtcttatg  20820
tgatgggatt gtttatatgg tttctgttat ggtttgtata tgggagtggc actatcagaa  20880
ggtgtgaccc tgttggagta ggtgtgtcac tgtgggtgtg ggctttaaga ccctcatcct  20940
agctgtctgg aagtcagtat tctgctagca gccttcagat taaggtgtag aattctcagc  21000
tcctcctgaa ccaagtctgc ctgcatgctg ccatgttccc accttgatga tagtggactg  21060
```

```
aacctctgaa acctgtaagc cagccccaat taaaacttgt ccttggtcat ggtgtctgtt  21120
cacagccgtg aaaccctaac taagacagtt tccttggata aagggaaaga atgcttatct  21180
gtgtctaatc ctgccacatc tcaacacttt tcagactgta caacaaaaat aaatgcacgt  21240
attgtgggag gaacaaacgc ttctttaggg gagtggccat ggcaggtcag cctgcaagtg  21300
aagctggtat ctcagaccca tttgtgtgga gggtccatca ttggtcgcca atgggtactg  21360
acagctgccc attgctttga tgggtaagtt tcagggtcat cttattatac caatgtgtgt  21420
gtgtgtgtgt gtgtgtgtgt gtgtgtgtgt gtgtgtgtgt gtgtgcatgt agaggttaat  21480
ctcgggtatc tacttgtact gcttgttcat cttatttgtt gagatagggt aattcactga  21540
acctagtgct aaccttttg actagacaga taggtatctg cctgtctctg tctcctggta  21600
catccttagc cctagttctg ggttggggat ctgaacttga atcctcaggt ttgagaacca  21660
agccctttgc ccactctgcc atctccttgg ccctgagata tttgttttta ggacaagaaa  21720
agtttcaaag tccttgccta gaaaatatta taattttaaa ttcagcctgt atatccttta  21780
cgtggttaat ttaaaattca aaggaaaggt aggtagattt ttaagcaaca aaataccttt  21840
aattcctgct ggggcttatt ttaatcagta cagctacatg aaggctcgga taatgagagc  21900
aactgttttt ggggttggta gactgaacct gattctccca aaggttcttc aaaaggcaca  21960
gaagcactcc tgtgctctta cttgaaataa acagaaagta atttttaagt acgtcttgag  22020
tgtttccagc cacagcgttt atactgtgaa ctgtaatcct ttaggaacac agtgcaacag  22080
aatatgagcg tcttccaaga ttttagcaac agtaaagggt ccctgaaggg acactgataa  22140
aaatgaatcc acaataaaaa gtatgacaaa cccgaggcat tctgagagcc ctctcctgtg  22200
ctgtgtctga ggattcctct gcagcctttg ttcctgacac acaacatcat gcttactgtg  22260
cactgtgcat atcgccaggc tgcgtagtac cagcagatgg taccctaaac ccaatcaatc  22320
agactgagga ttctttaatg gtgtgaaact ggtgtgtgtg gtatgtgtgc cttaggattt  22380
ctgctcttac aggaacataa cagtataatt tttaaacaatt taaaaaaaaa cattaagatg  22440
tctcttgtca cagtgtgtct ttggattgta cagtgttaaa ctctgatttt cagtgttgct  22500
ccagctggtt agttgagttt cataaaaact cattgaatga acttgggctt ggatattaga  22560
gtttccaaaa ctttctaaac cgtccttaat ctaagactat catttggttc tccacattta  22620
tgtgaagtgg tgcttctcag ctttatcagt tataaaagta aaaaattaag gaactcctaa  22680
aaacattgag gttgttcttc gtcttttagt atgaaatact tagacatgtt ttaattattt  22740
atgtggaaat aaacaagccc attattctat taatatgagc gtttgctaat aagtggtaaa  22800
aattctccat acatcaaaaa ttgtcttgca gtaaatttct ttataatata ttaccagtaa  22860
atgtttaata tgtgtacctg cttcatatag tcacacacag agacataaaa ataaaatctt  22920
ttcaggcaaa agggagtctt aaatggaaga aagttttatt acaaactaaa tcttcaaagt  22980
ccaatacgac tgctgtaagc aatgacaggt tgccttgcca ggaaaaggtg actaggtcat  23040
atggaatgtt gtctttcttt tctctccacc ccttcaagaa aatgtgctaa gaaaaaggag  23100
cggaggaagg atgccaacgt tactttgttt ccctcctaga attccctatc cagatgtgtg  23160
gcgtatatat ggcggaattc ttagtctgtc cgagattacg aaagaaacgc cttcctcgag  23220
aataaaggag cttattattc atcaggaata caaagtctca gaaggcaatt atgatattgc  23280
cttaataaag cttcagacgc ccctgaatta tactggtatg cagcatattt aagaggaacc  23340
tgcacaactc aatggtattg gtgtcaattt ccacttcagt ttgcatgaga agagagatct  23400
gcagcaattg tctttgtgtc ctggttggtg aggctgaggg agagatgagg ccacctgggc  23460
```

-continued

```
agtagaaatc ccgtgtcttc ccatacattc actgctatct gaggggcaaa aaagcttcat  23520
tactttctca gagtggcatg caactgagtg tatggtattg gtctaggaaa gattttgaca  23580
tctggggaca ttgggcatct tctgacaaga ttggcagaat gactatggct taggaatata  23640
caaccatatg aaagtgaacg ggactagatg ttagtgccca agaataccct ggttgacaat  23700
ggggggacac ggagcatgga gctgctttgg aggcacatca ctccacagga atggaatgtc  23760
tgccaacacc attacctgca agtgtctgtg aacagtcatg agaccttaga cagcttggct  23820
ttcctccttc cacctctaat atctgctgca cgcgtgctga tctccgtgtt gcttccttgc  23880
aatcattaag caacgtattc aaataaagcc ctgggagagt atggctattt ttgctctgtt  23940
tctgaattct gctacagtgt atattaaaca agacataaga aagtagacat atgtttgcca  24000
ataaattttg gttgaagagt ccctcttccc catagaaatt tcgttccaaa atgccataca  24060
gaatgtgaga attgtcttga attgtgggct ttagaaattg ctcagaaagc tggagggtcg  24120
ttctttttag ttttagtaat gggtttcatt atatttcata catatgcata gtatgatgta  24180
attgtattca catccttcac tctctcttgt cattttcact cctgcagttc tccctgctcc  24240
tcccaagtag tcccagactg gtcattcttg ctttgttgct ttgtagaaaa agaataagag  24300
aaaaagatag atactaattt ttgaagttcc catctatggt ttcaattagt ccaaatctat  24360
tcatgaaatt ttctttcaga attccaaaaa ccaatatgcc tgccttccaa agctgacaca  24420
aatacaattt ataccaactg ttgggtgact ggatggggct acacgaagga acaaggtaca  24480
gtatggcatg tgaaatgttc ctgtcttaca tgctaaagta catagagtag atccactcaa  24540
caagccttac tcatgacctt tctgttcatt ccaaactatt ggtcctctga ttcccaagaa  24600
tgtgaatttt tttacattaa acatcaatga gctaatcctt taagaatatt actcataata  24660
gagattattt ttatgagtct gcattaagaa ctgtggccct atgatactat caagtccact  24720
gaatcccatg tggtcctcag tacttactgt gtccctgttt gctaagttct cccttggtat  24780
caatagctaa ggtgccagca tctctcttga agaacagttc ttaatattta tttaaatgcc  24840
ttcttgtaaa aaatctgaca tttcctctaa ttatgccatt aaatccttat gtaaaataca  24900
tagattcata aagagagaaa agtagattgc agtacagtta ccaacatttg ttaatagaat  24960
tttacatagt gatgatcata tttgattatt agtgtactca gttgcaaatt gttttaaaat  25020
ctaccataat gttgaagtag ttatgggcat aaacaacatt ttcctttctg tcgtaactac  25080
aattcaaagt atctgtgacc cttacactac agtgctgcca acaatatcac attcctgcat  25140
tagttatctg aacttaaaac tgaagggcgt ctgcagcttt atttgaaagg ttgagaatat  25200
agaggcgagt ttttcgcttt cccttccgct gagtgtatgg atgcctcgat tgtgtggctc  25260
tgaactcaag accccctgtgt gctgagactt gagctatttc tctagaaata agaatgcttt  25320
ctttctagac tgagtgccag ataaccagca ttagacatat ttgagtgatt ttttttaaag  25380
gagatgattg gctgtgtctt ctttatattt cctgaaccag tcagtactgt attcaattag  25440
ttcccatttt ccactacatt tacttggcta cctatatgtg gacacacaca tatatacatg  25500
catatacata catacataca tacaaacata catacaaaca tctgagaaat atagacatgg  25560
gtagacatta agttatctgt aaatgtatca tttattgcag aacaaaatac tactctgctg  25620
tcagatgttt gggatgtatt ctcataaatt gtacatttta ttataatttg aatttctaaa  25680
acaatgaaag gcaagaacat cctttaaagg tacaaatgtg tgagacaaca tttttgagg  25740
ggggcatcgg ttgatatagg aggatgcctg agatcataga aacaagtctg cagaggcttg  25800
```

-continued

```
ggtgctagcg agtctgaaat atgtcactag aaggaaggca gcacggatca ctgctccttc  25860
atctccttct ccccttctc cttctccctc tcccggtctc tcttctccct ccacctcttg  25920
cttcccttct ccctcccttt ccctctgccc tatttattga acttcctctc cttaaaggca  25980
cttcttgatt gcttcatagg tgaaacgcaa aatattctac aaaaggctac tattcctttg  26040
gtaccaaatg aagaatgcca gaaaaaatac agagattatg ttataaacaa gcagatgatc  26100
tgtgctggct acaaagaagg cggaacagac gcttgtaagg taatggggaa aaaatacaca  26160
atagttccat gaagacagtt cattcaaaaa cgaatctcca aagttatatt tcattagttt  26220
tggttctgaa gttccagagt taaacgattt gaaggctatt tgaaacgata gcctttaaca  26280
aattaaacac acatagtgca tattatatgt tacttataat agttatgcta gaatatgtat  26340
tgctgtgaca ggtatgtcac agtgaggaca ggggcatgcc aaatttaagg acaattttta  26400
catgccatgg tcatgctaaa atacaagaaa agtagattta tttgaacttg gagtaaagat  26460
gctaagtctg ttgggtttat ctgagaatgg gagagggaat aaattggcct tgtaaccatt  26520
cacttatttt ttttttcatg gctaatggga tgcacagaaa ttgagaggct ccgtggtggt  26580
gtgtaaagtg tgactgccaa atattaaaga catctgtcta tgagcaaggg gctccttatt  26640
tgcatcatca ccattacccc tctctacctt tgtatttctc taccctctgt gacccaggga  26700
gattccggtg gccccttagt ctgtaaacac agtggacggt ggcagttggt gggtatcacc  26760
agctggggtg aaggctgcgc ccgcaaggac caaccaggag tctacaccaa agtttctgag  26820
tacatggact ggatattgga gaagacacag agcagtgatg taagagctct ggagacatct  26880
tcagcctgag gaggctgggt accaaggagg aagaacccag ctggctttac cacctgccct  26940
caaggcaaac tagagctcca ggattctcgg ctgtaaaatg ttgataatgg tgtctacctc  27000
acatccgtat cattggattg aaaattcaag tgtagatata gttgctgaag acagcgtttt  27060
gctcaagtgt gtttcctgcc ttgagtcaca ggagctccaa tgggagcatt acaaagatca  27120
ccaagcttgt taggaaagag aatgatcaaa gggttttatt aggtaatgaa atgtctagat  27180
gtgatgcaat tgaaaaaaag accccagatt ctagcacagt ccttgggacc attctcatgt  27240
aactgttgac tctggacctc agcagatctc agagttacct gtccacttct gacatttgtt  27300
tattagagcc tgatgctatt ctttcaagtg gagcaaaaaa aaaaaaaaaa aaaaaaaaaa  27360
aaaaaaaaaa aaaaaaaaaa aaaactgaga aagaggtaga aatctttgta acatttcatt  27420
tagaataaaa agagtctcta cttgaacctg atgggacatc taaaccacct ttctggccat  27480
tgctgcagag ttctgcatgg tcatgactgc atgaggtttc ctacccctgg agcagagcca  27540
tctgggcatg agggttgctt gtataaactt catgttcctc cctcaggaaa taacctctct  27600
gcctaggtta ttgaggaata tcctctctgc caggacagcc cttaagactg tgggaaagaa  27660
ctcttaaaac ataagttcaa gaatatataa tttctcagct atgtaaaata taaggataca  27720
atatgaattg tataaggaga ttcgattcgt ggacctaaaa gaacaaaggc agctgcacta  27780
tgagccagct tgtcagaaag atactactga aggagataaa gagataaaga gatttaggga  27840
gtggtgataa cagggcaaga tcccagccag ctaagtttat tatttgtgct tacataggca  27900
ggcagagtcc tgagttcaag atcagcctgg gacagagcta gtttagaccc agggttggtg  27960
ggaatcccac ccagctagct tgttgtctat gctaagaaag acaggcagat ctctgaattc  28020
atttggcatg ttttttttt ttaaaaaaag tacctgatgt cttttcttaa gaatcaagag  28080
gctagagtca tggaatgctg actcatgggt taaacaaaag ggaatctaga gtaagtgact  28140
gagttgatat gtaaataaaa gactgggctt tagtctgcaa gagctgagct acctggatga  28200
```

-continued

```
gctgtctgga gatctctgta gagcagaata ctagtctcta attttttag atttttttt  28260

tttctagtag ctactcagag agaactgctt agagaatgaa atgaacattg ctattttagt  28320

tgtgttgttt tgtttttttt tttttctaga aaatccaaaa atattttata gaagcttctc  28380

tgactctagt cagaaaaccc atgagctagc cagagagctt ttggattttt ttttcctagc  28440

aagagaaagc tgtctcaaga agagacagct gtctcaagca aaagagctgc cttgagcaga  28500

aagctatctc tatcagactg catagccaag agctatctgc agaaagctgt ccagctgtct  28560

agactacaag gctgtcagct tgcaacccat catatgactt tgagttgttt ctttcaccgc  28620

tcccagacac cccttctcgc aggaacctcc ctccaagcca aggctggtcc tgggcacctt  28680

gccacatggt cttggctaca gatgtgtgca agacctgtaa ggctatattt ttcttcttgt  28740

gtgcagctcc tgcaataggc ctatcacaca gtactcacac agggcaaggg atctgatgag  28800

aacctcctgg ggaaccctcg gggttcagct gatgctgtat tctgcaatag taattcatgt  28860

aatgtcattg ggtgtaaagt gttgtataaa attcaagctt ccaattgagt tgaaagtgaa  28920

aagcaatctt ggaatggatg acattaatcc tcatgcaaga caaatttcca gcttcccatt  28980

gattcataaa gtgggtcatc tgtgcttaac tccatttagt taacctggtt aatatttaga  29040

cagaattagc catttacgaa ctactgtgca agttaaacag acaaatagaa aagtgaaatt  29100

tcctaaagaa gattaaactt ttccttgcat atataaaggc ttgttgagta gtgcagaggg  29160

ttaaatatgg aagatcctgt gggttatcta cagagttcac catgggaagt gtaagaggtg  29220

gaagcaaatg gctttggaaa aatcttccaa gcacacaact tcaactttta attttgtaca  29280

ccatttcatc ttaatctgtg tggcagttgt tttatattta aaaagaaaga agtggttctc  29340

aatgaaaatc ttgtatctca aggtttcata ttaataaccc taacaggtat ttacacaagg  29400

tgtcacagta cttactgggt aaactttggg ctttggtttc tcaaggaatg gcctcatttg  29460

agcaaaacag agttttgaaa tgagggattt ccctatggcg taaagtacca tgatcacgtt  29520

gccagctgga gtccagctgg gctggaatgc tctgcttttc attgtgtgtt cctgcacaaa  29580

gtagcccgtc ttccactcga agccttaaga ggctgagaaa atgagagggc cggataacat  29640

cacttttaca agacaaagtg gaggcaggag gccctagatc tttggcaggt ccatccaaga  29700

aagggagtgt cacctctgga atggaacaat gccggcactg ttcttcctgg gccgcacgtg  29760

gagagcacac agcacaccac taacacttct agagctcaac gggaagctca aagggctgtc  29820

tgatctctat ctattttttt tcttgtagtt cttgcttatg gctaccagcc ctacaaactg  29880

tcaacaactc tgaaggatgc tcttgcatct ctgcctctct ctttcatcag tacttcatgt  29940

gaataggaat gtggcaaata ggagagattt gggtttgctg ttattatttt tgttgctgtg  30000


<210> SEQ ID NO 14
<211> LENGTH: 2513
<212> TYPE: DNA
<213> ORGANISM: Rattus norvegicus
<220> FEATURE:
<221> NAME/KEY: CDS
<222> LOCATION: (65)..(1981)

<400> SEQUENCE: 14

tgaagactag cttcatgtga agactccttc tcctccagca gcacaaagca accatccttc     60

cagg atg att tta ttc aaa caa gtg ggt tat ttt gtt tcc ttg ttc gct     109
     Met Ile Leu Phe Lys Gln Val Gly Tyr Phe Val Ser Leu Phe Ala
     1               5                   10                  15

aca gtt tcc tgt ggg tgt ctg tca caa ctg tat gca aat acc ttc ttc      157
```

-continued

```
Thr Val Ser Cys Gly Cys Leu Ser Gln Leu Tyr Ala Asn Thr Phe Phe
                20                  25                  30

aga ggt ggg gat ctg gct gcc atc tac acc ccg gat gcc cag cac tgt      205
Arg Gly Gly Asp Leu Ala Ala Ile Tyr Thr Pro Asp Ala Gln His Cys
            35                  40                  45

cag aag atg tgc acg ttt cac ccc agg tgc ctg ctc ttc agc ttc ctt      253
Gln Lys Met Cys Thr Phe His Pro Arg Cys Leu Leu Phe Ser Phe Leu
        50                  55                  60

gcc gtg agt cca acc aag gag aca gat aaa agg ttt ggg tgc ttc atg      301
Ala Val Ser Pro Thr Lys Glu Thr Asp Lys Arg Phe Gly Cys Phe Met
    65                  70                  75

aaa gag agc att aca ggg act ttg cca aga ata cac cgg aca ggg gcc      349
Lys Glu Ser Ile Thr Gly Thr Leu Pro Arg Ile His Arg Thr Gly Ala
80                  85                  90                  95

att tct ggt cat tct tta aaa cag tgt ggc cat caa tta agt gct tgc      397
Ile Ser Gly His Ser Leu Lys Gln Cys Gly His Gln Leu Ser Ala Cys
                100                 105                 110

cac caa gac ata tac gaa gga ctg gat atg aga ggg tcc aac ttt aat      445
His Gln Asp Ile Tyr Glu Gly Leu Asp Met Arg Gly Ser Asn Phe Asn
            115                 120                 125

ata tct aag acc gac agt att gaa gaa tgc cag aaa ctg tgc aca aat      493
Ile Ser Lys Thr Asp Ser Ile Glu Glu Cys Gln Lys Leu Cys Thr Asn
        130                 135                 140

aat att cac tgc caa ttt ttc aca tat gct aca aaa gca ttt cac aga      541
Asn Ile His Cys Gln Phe Phe Thr Tyr Ala Thr Lys Ala Phe His Arg
    145                 150                 155

cca gag tac agg aag agt tgc ctg ctg aag cgc agt tca agt gga acg      589
Pro Glu Tyr Arg Lys Ser Cys Leu Leu Lys Arg Ser Ser Ser Gly Thr
160                 165                 170                 175

ccc acc agt ata aag cca gtg gac aac ctg gtg tct gga ttc tca ctg      637
Pro Thr Ser Ile Lys Pro Val Asp Asn Leu Val Ser Gly Phe Ser Leu
                180                 185                 190

aag tcc tgt gct ctc tca gag atc ggt tgc ccc atg gat att ttc cag      685
Lys Ser Cys Ala Leu Ser Glu Ile Gly Cys Pro Met Asp Ile Phe Gln
            195                 200                 205

cac ttt gcc ttt gca gac ctg aat gta agc cat gtc gtc acc ccc gat      733
His Phe Ala Phe Ala Asp Leu Asn Val Ser His Val Val Thr Pro Asp
        210                 215                 220

gcc ttc gtg tgt cgc acc gtt tgc acc ttc cat ccc aac tgc ctc ttc      781
Ala Phe Val Cys Arg Thr Val Cys Thr Phe His Pro Asn Cys Leu Phe
    225                 230                 235

ttc aca ttc tac acg aat gag tgg gag acg gaa tca cag agg aat gtt      829
Phe Thr Phe Tyr Thr Asn Glu Trp Glu Thr Glu Ser Gln Arg Asn Val
240                 245                 250                 255

tgt ttt ctt aag aca tct aaa agt gga aga cca agt ccc cct att att      877
Cys Phe Leu Lys Thr Ser Lys Ser Gly Arg Pro Ser Pro Pro Ile Ile
                260                 265                 270

caa gaa aat gct gta tct gga tac agt ctc ttc acc tgc aga aaa gct      925
Gln Glu Asn Ala Val Ser Gly Tyr Ser Leu Phe Thr Cys Arg Lys Ala
            275                 280                 285

cgc cct gaa ccc tgc cat ttc aag att tac tct gga gtt gcc ttc gaa      973
Arg Pro Glu Pro Cys His Phe Lys Ile Tyr Ser Gly Val Ala Phe Glu
        290                 295                 300

ggg gaa gaa ctg aac gcg acc ttc gtg cag gga gca gat gcg tgc caa     1021
Gly Glu Glu Leu Asn Ala Thr Phe Val Gln Gly Ala Asp Ala Cys Gln
    305                 310                 315

gag act tgt aca aag acc atc cgc tgt cag ttt ttt act tac tca ttg     1069
Glu Thr Cys Thr Lys Thr Ile Arg Cys Gln Phe Phe Thr Tyr Ser Leu
320                 325                 330                 335
```

-continued

```
ctt ccc caa gac tgc aag gca gag ggg tgt aaa tgt tcc tta agg tta     1117
Leu Pro Gln Asp Cys Lys Ala Glu Gly Cys Lys Cys Ser Leu Arg Leu
                340                 345                 350

tcc acg gat ggc tct cca act agg atc acc tat gag gca cag ggg agc     1165
Ser Thr Asp Gly Ser Pro Thr Arg Ile Thr Tyr Glu Ala Gln Gly Ser
            355                 360                 365

tct ggt tat tct ctg aga ctg tgt aaa gtt gtg gag agc tct gac tgt     1213
Ser Gly Tyr Ser Leu Arg Leu Cys Lys Val Val Glu Ser Ser Asp Cys
        370                 375                 380

acg aca aaa ata aat gca cgt att gtg gga gga aca aac tct tct tta     1261
Thr Thr Lys Ile Asn Ala Arg Ile Val Gly Gly Thr Asn Ser Ser Leu
    385                 390                 395

gga gag tgg cca tgg cag gtc agc ctg caa gta aag ttg gtt tct cag     1309
Gly Glu Trp Pro Trp Gln Val Ser Leu Gln Val Lys Leu Val Ser Gln
400                 405                 410                 415

aat cat atg tgt gga ggg tcc atc att gga cgc caa tgg ata ctg acg     1357
Asn His Met Cys Gly Gly Ser Ile Ile Gly Arg Gln Trp Ile Leu Thr
                420                 425                 430

gct gcc cat tgc ttt gat ggg att ccc tat cca gac gtg tgg cgt ata     1405
Ala Ala His Cys Phe Asp Gly Ile Pro Tyr Pro Asp Val Trp Arg Ile
            435                 440                 445

tat ggc ggg att ctt aat ctg tca gag att aca aac aaa acg cct ttc     1453
Tyr Gly Gly Ile Leu Asn Leu Ser Glu Ile Thr Asn Lys Thr Pro Phe
        450                 455                 460

tca agt ata aag gag ctt att att cat cag aaa tac aaa atg tca gaa     1501
Ser Ser Ile Lys Glu Leu Ile Ile His Gln Lys Tyr Lys Met Ser Glu
    465                 470                 475

ggc agt tac gat att gcc tta ata aag ctt cag aca ccg ttg aat tat     1549
Gly Ser Tyr Asp Ile Ala Leu Ile Lys Leu Gln Thr Pro Leu Asn Tyr
480                 485                 490                 495

act gaa ttc caa aaa cca ata tgc ctg cct tcc aaa gct gac aca aat     1597
Thr Glu Phe Gln Lys Pro Ile Cys Leu Pro Ser Lys Ala Asp Thr Asn
                500                 505                 510

aca att tat acc aac tgc tgg gtg act gga tgg ggc tac aca aag gaa     1645
Thr Ile Tyr Thr Asn Cys Trp Val Thr Gly Trp Gly Tyr Thr Lys Glu
            515                 520                 525

cga ggt gag acc caa aat att cta caa aag gca act att ccc ttg gta     1693
Arg Gly Glu Thr Gln Asn Ile Leu Gln Lys Ala Thr Ile Pro Leu Val
        530                 535                 540

cca aat gaa gaa tgc cag aaa aaa tat aga gat tat gtt ata acc aag     1741
Pro Asn Glu Glu Cys Gln Lys Lys Tyr Arg Asp Tyr Val Ile Thr Lys
    545                 550                 555

cag atg atc tgt gct ggc tac aaa gaa ggt gga ata gat gct tgt aag     1789
Gln Met Ile Cys Ala Gly Tyr Lys Glu Gly Gly Ile Asp Ala Cys Lys
560                 565                 570                 575

gga gat tcc ggt ggc ccc tta gtt tgc aaa cat agt gga agg tgg cag     1837
Gly Asp Ser Gly Gly Pro Leu Val Cys Lys His Ser Gly Arg Trp Gln
                580                 585                 590

ttg gtg ggt atc acc agc tgg ggc gaa ggc tgt gcc cgc aag gag caa     1885
Leu Val Gly Ile Thr Ser Trp Gly Glu Gly Cys Ala Arg Lys Glu Gln
            595                 600                 605

cca gga gtc tac acc aaa gtt gct gag tac att gac tgg ata ttg gag     1933
Pro Gly Val Tyr Thr Lys Val Ala Glu Tyr Ile Asp Trp Ile Leu Glu
        610                 615                 620

aag ata cag agc agc aag gaa aga gct ctg gag aca tct cca gca tga     1981
Lys Ile Gln Ser Ser Lys Glu Arg Ala Leu Glu Thr Ser Pro Ala
    625                 630                 635

ggaggctggg tactgatggg gaagagccca gctggcacca gctttaccac ctgccctcaa   2041

gtcctactag agctccagag ttctcttctg caaaatgtcg atagtggtgt ctacctcgca   2101
```

tccttaccat aggattaaaa gtccaaatgt agacacagtt gctaaagaca gcgccatgct 2161 caagcgtgct tcctgccttg agcaacagga acgccaatga gaactatcca aagattacca 2221 agcctgtttg gaaataaaat ggtcaaagga tttttattag gtagtgaaat taggtagttg 2281 tccttggaac cattctcatg taactgttga ctctggacct cagcagatca cagttacctt 2341 ctgtccactt ctgacatttg tgtactggaa cctgatgctg ttcttccact tggagcaaag 2401 aactgagaaa cctggttcta tccattggga aaaagagatc tttgtaacat ttcctttaca 2461 ataaaaagat gttctacttg gacttgaaaa aaaaaaaaaa aaaaaaaaaa aa 2513

<210> SEQ ID NO 15
<211> LENGTH: 30000
<212> TYPE: DNA
<213> ORGANISM: Rattus norvegicus

<400> SEQUENCE: 15
attcctccag cccctgtatc acgtcaaact cgaaactcca gctccaggac tagctgcagg 60
cattgatgct tctgcgctgt ttccattctg tgatcatgtc ttctccatac ctacctctaa 120
gttttccatg aggtctcaaa gtaaaagctt taagaagaaa aaaaaagtgt tgtccagcag 180
gtttcagtaa gctttgctgg agaggaccag ataataaaat cttagtttgc ttgtttgttt 240
tgttgttgtt actgaagacc gttctataat cataggaagt aggcaggcat acatcgtgca 300
gcagtgaatg gacatggttg tgttccatta aaacttcagc tagaaggaca aatcccaagc 360
aagatttgtt ctgtaaacag tggattatta actcagtact gggtggatct gaacatgaac 420
ttccagtgta ataaaaaggt agaaaagcag aagtgtgaag aatcccgaga gctcagggga 480
gaccactgct tctgctcaca ttcctggccc aagaggactc cccctggaga cctctggaca 540
caagaaccga ggagcagtct ggttcctgcc tgtacccaga actgacactg taacacatct 600
acacagtgga gtattactca gctattaaaa acaatgactt catgaaattt ataggcaaat 660
ggatggaagt agaaaatatc gtgagtgagg tcacccaatc acaaaagacc cacacggtat 720
gccctcactg ataagtggat attagcccaa aagctcggat tacccaagat acaatccaca 780
gaccacagga agctcaagaa gaaggaccac caaagatgca gatgcttcag tccttcttag 840
aagggggaca aaaatattca taggagaaga taaggagaca aagtttggag cagagactca 900
atgaatggtc attcagagct gccccacctg gtgatccagc ccacatgcat acagccacca 960
aacccagaca gtatttctca tgccaagaaa tgcatgctga caggagcctg atatagttgt 1020
ctccagagag actttgccag ctcatgacaa aaacagaaga gaatgtttgc agccaatcat 1080
tgaactgaaa ccagggtccc tgttggagga gttagtgaaa agattgatgc aaccccgtaa 1140
gaacaacaat accaaccaac cagagctccc agggactaaa ctaacttcca aagagtactc 1200
atgaacaggc caatgtctcc agctgtatgt atgtagcaca ggatggcctt tctgggcacc 1260
agaggaagaa gcccctggtc ctgccaaggc tggaccctcc cccagtgtag gggaatgtca 1320
agatggagag gtgggaagag gtaggttttt gggttgggaa aaggtgataa catttgaaat 1380
gtaaatttta aaaatccaat ttaaaaaagg tagaaaacca ataccttgct ttgattctcc 1440
tataggagct gtctacccca cccccacatt gaggtgtgcc tccaggaaat ttcaatagaa 1500
gtatacacac acacacacac acacacacac acacacacac acacacacac acttgtaaag 1560
gcaaataggt aagaatcaag ctgttagtcc ccaaataaag agatatgacc attttcaaaa 1620
tgggagacct atgcctgaat tgtgtgtccc tagtataaag cacttctctt tcttcagcat 1680

-continued

```
aagcacttaa acgcatttcc catgtataat ttatttaaaa tgggttcttg atatgcttgt   1740
aatataatga tatcttggta tacatgaaca ctgtaacatt atttccactc taaagttact   1800
taacacagtc accatctcag acaattatta tgtatgttac gaatacctgc ataccagggt   1860
acagtgtgta cacctataat ccagcactct gaagatctag attcagtggt tctcaacctg   1920
gggagagggg tcacatatca gatatttaca attcataaaa gcagcaaaat tacaattatg   1980
acgtagcaac aaaatacctt tatggttggg gatcactata catgaggaac tatattaagt   2040
cgcagcttag aaaggttgag aactactgct ctataggatg caaagacagc tcaggggtgc   2100
tcttgaagag aacccaagct cagttcccag caaccacatc aggtggctca caaggacctg   2160
tgtctccagc tccaggggac ctgattccct ctgtcggtct gcaacgtgca tgcatttgca   2220
gtgaaagaga cacatcatta gaaataaaat aaatggttaa aatttaacta atgttgctat   2280
tgctgggcat gggatcttgc agtctattag ttctaaaagc tgaaattttg tatcctttca   2340
caaacaccac ccatgacacc aagtttcaga tcctgacact caccatccca cttgtttcta   2400
gggcttgcct ttttcaaatg ccacatgtaa gtatagctct tcaaatggcc atatgttttt   2460
atatctccac cagttttgca tcactgcaat ccaatacctt gagcccctat gtcgaattta   2520
taatctgccc atcagttgac tttaatttat ttagggttgc ttataagttc ctaatttttt   2580
tcttttggtg attttgtttt tcttttctga ttatttgtga tcttctggct ttgtgttggt   2640
gtttgcactt ttagataaga ggctatttta aatttaattt ttaaaaattt atttattcac   2700
ccattgcaag gctatgtgtg tgtgttctgt gcaggttctg gggattggac tcaggtcatc   2760
aggcttgatg gcaaatgctt ttgacctact gagatgtctt gtaagctcca cgatgatttt   2820
agacttttaa agcttgcttc actgggcaaa cctagtagtc atgtatctca tcaatggatt   2880
ctgggttagc caactgtgta gttagagttg gatatgcaag gctaggtttg aatcttgggt   2940
ccacagaaaa gagcattgca tcagggtcca ccgtgattac attgatgact gaattcctag   3000
agcccatgct tgaatcctca gatcagtggg gccacgatct tatgattgag gactgcctta   3060
acatgttgat attgaaatga acctgaaaac tgagcctcca gtggccatgt taacgaactc   3120
aagcccgtgg gcatgggttt gttcctgaat ctacaatcgc tgtcctggaa atgagccctg   3180
gaaatgggac aatctggtgg ctggcctgag gtatcatcct ggagcctggg tctgcagggt   3240
cagcctgata actgggattt cctggaatgg acttgtttac atctgtcttt attcataggg   3300
aacacatcgc cattctgtgc tgcccaggct tagtagcagg gttttatggt taaagtgaag   3360
gatcgaacac tcttcaatgc ctattcacta tgtccacagt ttcaccgggg gctgtaacct   3420
atcatctggc tttcttaaca cttggaaagg catggggaat tgttcccatg gattcttctg   3480
caaagggatg cgtggtggag attccaattt tgtcatggtg tttacatgac tttctggaat   3540
cggtaacata ttaagtactt gaacctggac tggaaggtcc atggactgta ttgacaggtc   3600
aaacagaaga cactgatgcc agaagcccag tgtcaacact ggagccaagc agagaccaac   3660
ctcagtgcca tattcggaga gcttgaagac tagcttcatg tgaagactcc ttctcctcca   3720
gcagcacaaa gcaaccatcc ttccaggtag ctactctcca ccattctcat tgtagcctat   3780
gtcttaggaa tttatttttt taaaaaagta taactatatc tgcatgaaaa agtctattgg   3840
tgtaatgcac taatttcctg agggtttaga aaatctacaa ggaattgttt ttctttgtac   3900
agctatatta atgtaaaata ttttaaagcc aaggataagc ttttgattct tttcaaagat   3960
gctctttatg tgggggttgt gggtgatatt attgtactca ttcataataa ttttgcataa   4020
atctagaaat ttaataagtg tttaattatt tgtatcaact ctctttacaa aattaataga   4080
```

-continued

```
aataattctt caaaattaac aataaataca ctaatacaca ctaattgtag tctagaggtc   4140
tcaatttgta tcttggggag catgataaat attttaattt tctatatcca aaatgtcccc   4200
tcctccaaat cctctttctc ctggtgatta tgtgttgtga tttgcaattt agacatttac   4260
caaaaaggtg aagtgtacat taaattaaat tgtctattaa atacatggta aacatgatct   4320
caacctagta gtagctaaat ttattttttt ctttcaaagg atgattttat tcaaacaagt   4380
gggttatttt gtttccttgt tcgctacagt ttcctgtggt aagtattagc ctgggagttc   4440
aaattaagtt agtgtgtgaa actataccac tcctggagaa agcctttaaa agctttgggg   4500
aagaaggcag ctgctgatag tccaaggcaa gaacctctcc ttagatacat tactcctgac   4560
acagaacggg gtgggggggg aacttagaag cttcaatgct tctgctagca gaaatttctg   4620
tatcaagatt tctctctagc agagtcctcc caccccaaag atttgcttgt gtttattacc   4680
agccctctaa ataaaaactc tacctgaaaa tcggaaagaa tatcagatat tgcataatga   4740
ttgagtccaa tccaagcttc tgattagtat atggtatttt taatataagg catagagagc   4800
catttctgaa ctgaaaacac ctgctttgga tttaatgagt gtagtaaccc tttggtagtg   4860
tggatggaca gctttaacac tagatgtcag tgttctttct ctgtgaattc cattacggtt   4920
cagaatgtga gcatggccct ggacaccccc ttctcaatag tcattataga gtgagatttc   4980
cctgggcata tcatagtatt ccgatcaaag ctgactttgt ctagccacac ctcaagggct   5040
gatcttgact ctcaagtatt tggcaaagat gagcttatcc ttgtcaatag aagccatttc   5100
tctgggtaaa ctcattgttt tccctctctg ctccctccat ctggcccatc aactgtaact   5160
gcttttctgt gccacaacta ctgccatgat caaaccaatt aaacacgagc agtggtagtc   5220
agagatgcta tgggccatgg ctataaaatt tacgatcatg acaggaacgt gagacatgga   5280
aatacattta atacttgaga acaagtactt tacatagtcc taaagtacaa aataatgatt   5340
gcttgctttt ctttagtctt tcttattttt ctgcatgaat ctgttgtata aaagtgttat   5400
tcgtgaataa taattttaat gagaaattat gactattaat gacaaatcat ttttgactta   5460
cctttgctat ttatagctaa tgttaacaca aacaagcact tttgtcattc gttcttcttc   5520
acgctattct gtatgcatgt gacattctat gcacacattc aattatttct actgattcaa   5580
attttagaaa taaaaatttt tagatacaaa catgtgaata cctttgaagg ttttatggca   5640
tgcattatgg tattagcttc cagaaaggca tcctctgttt ggttttccct acgagcatgt   5700
gggagtgttc aaccatccca gttagagtga gccctaacag gcatctgtta ctttgtagtc   5760
tggcgtagga tcaccgttct aaaatagcat ccagatttct tcctgaggaa ccatctccaa   5820
cggatggccc acatggtact ggagatgatt ctcctgctgc agtcagacca gaactgcaga   5880
cagtgctggt gtgatgacct gaccagagct agtcttgtaa caggcttttt ctcagactta   5940
gaaaaaggct cagatttatt tttatttcca actcaacttg agctgctggt cctgccttac   6000
tagtgtgcat cttgagatga aggcagcatc acacaataga gtaaatcaac gctgacacac   6060
tgtgcatgga tgccattcct gagcagtgtc tagtgctcca taagccattg gctgtggaca   6120
catgggtttc tgaactgtta aactcattta tattcaaact gctctgattg attttctttt   6180
atttgtgaac aaagccagca cacaaatatt gtttcaagtt taatctttgt taacctggct   6240
gtttaaccca gtgttctgag tctgagactc ttacattttg ttttttttaac ataaaatgta   6300
tttaatattg acatatcatt tctaagagat tatattgtta attcagaaaa agaatgtgtt   6360
atctacattc ttaaaatatc ataaagattt agacaatgat ttcttttta gaaagttatc   6420
```

-continued

```
taaattatca ctaatatgaa atatcaggtg gaatatcgtg tatttgtttt tctagtttag   6480
aaagaattaa tctgtagctt gtatgtattg actttgtgaa tgatgatagt ttttaaatgt   6540
ttttaattga cactaggatt ataccacccc tttcctccct ctagtttctc ctaggaacac   6600
ttccttgagc ttctcccatg ttcccctcac tctgaagctg attgcctctc ttttcattta   6660
gtattaatgc tacatatgta catatgtaca cagagatgta tgaatgcaac ttgttgagtc   6720
catttttgtt tgtgggtata tggtttgtgt gtgcttgtgc atattgaaca actagtaagt   6780
gggctcagct ctggaaaagg ttaattctct ttctccaaaa ggtcattagc tgcctatagt   6840
tctttgtcta aggtggggcc ccatgaaatt ccccettcca tgttactaca tccattgata   6900
ttgccatcgt tctggtccct tctgggaggg actgtttcac agcaaacttc ctgatattct   6960
ggctatcatt acctttctgt gttctctttc atgatatccc tcgagccata ggtttgggat   7020
atgagatgta gatatatcga ctggggctgg gagccccaca gtatgttgac ctccgcattg   7080
tgtccagttg tggatttttg tgatggtgtc tgtcttagtt agggttttac tgctgtgaac   7140
agacaccatg accaagataa gtcttataaa ggacagcatt taattggggc tggcttacac   7200
attcagaggt tcagcccatt atcatcaagg caggaacatg gtagtgtcca aggcaggcgt   7260
tgttcaggca gagctgagag ttctgtcttc atctgaaagc tactagcaga atgctgagtt   7320
ccaggcagtt aggatgaggg tcttaaagcc cacacccaca gtggcacatc tactccaaca   7380
gggccacacc ttcgaatcat gctaatccct gagttgagca aatacaaacc atcagtgtcc   7440
atttgctacc aagagaggct tctttgatga gagagagtag ctacctttat ctaggaaggg   7500
tggctcctgc actgttagca gcttttatac acatatagtt acttttatta attcggtaaa   7560
ttatcttttc atatctgatg ctgaatttta aaagttttag catttattta tttttactct   7620
atatctgcac atgcgtatac atatatacac atgtgctgtg gagcacatgt ggagatgaga   7680
ggacaacatg tggaggctca gtttctctc tgccactcac ctagagtttt gagttaagat   7740
gcttcattta tctatggaat ttttcctttt ctttcttttt gattatgtac atttttaata   7800
tgactaaata actcagtcat ggtccatgga cctgcagttt attgaaagac atcattatag   7860
atcaattagg tcatacagac tctgtgcaaa caaggctgtc attgttctaa tcattactgc   7920
tcaccatcgt tatcattgct gccatcatca actgaggagg ataatccatt ctccagttag   7980
aatgtttcga ctcattcatt ctcattgact gagtcacgtg ttagtttacc aacactcaac   8040
tgcaggatag aaacttctag gctgccactc gatgatggtt tgtgattttg tatgtgtctg   8100
tgcaatggga tagtgaggga gtctctgctc aataattatg agatgctaac acattaaaaa   8160
aaaaagcaag tctctttata gctactgtca gcactgggcc tgctactcag tgtgttgtgc   8220
aaatgggaca gcctgggttg tacacttggg aacatatatt cctaggagca attacccagg   8280
aaaatctcct ctttccaaat ataaatctga cttaagaagg taggcatggc aacacccctc   8340
tgataagaag aaaaacagta ttgcaaggtt gcctcatcca aattggactc agtggcagga   8400
tctccatata agtagaacat agaaactctt aactttccgg ttcttattga aaaacgtatt   8460
gtctagatag ctattcctta acaaacaatg gcaacatgga caacactgcc actggagtat   8520
tgcataatta atgaaaactt gactgctgaa aatggacagg ctgcctgttg gaaagctaag   8580
taaaatgatt tgaactgaat cttttcaggg aaatccgaat tcttcaatgg atttaaagac   8640
agttctctaa tgatatatgg ggtgcaggat acccacataa tggagttgtg agtcagcaca   8700
agcagtgtat cttattttca agttagctta ctttcatttt tgtaataatt tgaaaattat   8760
ttagcctttc cccattatat tgaaaataga gtcttttctc atgcaatata ttctgattat   8820
```

-continued gacttcccct cttcttcccc ttccagttcc acccccacct cccatcttct cctggtctaa 8880
tccctttctg cctctcatta gataagaaca aaacttctaa gagatagcaa tcagacacaa 8940
caaaataaaa tataataaaa cagaaaccat cacatgaaag ttgtacaagg caacccaaca 9000
gaaggaaaag agcctaagag aaggcacaag aatcggagac ccattcagga gtcccataaa 9060
aatactcagc tgaaagctat aaaatatatg tagaggaccc tgtgcagacc tgtctaggcc 9120
ctggttcttc agtctctgct catatgagcc tgacttagtg gaatcacagg actttgtttt 9180
cttggtgtcc tccatcccct ctaggtctta gagtctttct ccctcctctt tcacaggaat 9240
ccctcagctc tgaggggagg gatttgatgg agacacacca tcagagctat gtgtcctaag 9300
gactctgact cttccttctc ttcccctccc cccatctctc tctctctctc tctctctctc 9360
tctctctctc tctgtgtgtg tgtgtgtgtg tgtgtgtgtg tgtgtgtaat gtctgaatgt 9420
gggtctctac aaatacaatt ttattaagaa atgagctagt aggaaatcag tactcaatat 9480
ttattatttt atttaagtaa ggctgggtaa acagcatcat gggacagcac ctgctgtgct 9540
ggaaaaaagg acagaaaagg attgtgagtc aggaaggatg agtttatgtc cgaggatatt 9600
tattcactgt gtggtactaa tgacatctga actctgagac tcagttattg acttccttca 9660
tggaaaaaaa aaaggaaaaa acaaaaaaaa agaaatgcaa ataatagtcc tgacctcaag 9720
tcgcccttaa agcgctgagg aatctaggga gattgttgtc ctaaaagcgt tttgaaaaaa 9780
tgctgtattt ccatttttaa ggtgagatgt ttccccagcc tgttagacag caggcagaaa 9840
aaatatattt taacagatac tttatgtaaa attatatagg caataaaaat tttattgcat 9900
aaatttattc aattttatgc ataaatgtcc ataggatgac tttatttatt tttttttttt 9960
acgccccgcg gggcccata ggatgacttt aaatagcgtg ctgtattgtt taaacagttg 10020
tcatatgttt cattctacct gtgtggttgt atatatcttt gggtagtcat tgggataaat 10080
aaaaaggaaa aacaacatag atgtatttct actaaaatgg ttacactttc tccggaatca 10140
acttttatat cacagggtgt ctgtcacaac tgtatgcaaa taccttcttc agaggtgggg 10200
atctggctgc catctacacc ccggatgccc agcactgtca gaagatgtgc acgtttcacc 10260
ccaggtgcct gctcttcagc ttccttgccg tgagtccaac caaggagaca gataaaaggt 10320
aagatgtccg tgagtccaac caaggagaca gataaaaggt aagatgtccg tgagtccaat 10380
caaggagaca gataaaaggt aagatgtgct gttttatcac tgccgggtga gacgtttctc 10440
aaatagcttc ctgtcgtatg caaaattggt gtcatagttc tcagagtgtt cacagactga 10500
ttgcatcaga agctcctagg ctgggttttc tccaatgcaa actactagag tgctgaaccc 10560
agagacggag attctaaacg accacggcat ttgttcacac agcataggag ggagtgatgc 10620
ttcagccaag gcctgaagac agagcgtgta acaagaacgg gtccttcctc acgctgtaat 10680
acttagcttt cttcttcact ttcaacacgc tatactgtcc ccacgtgtac acttgttatg 10740
tgtataaata tgttattagt caggttctgc atctgaggga gaacatgagt tttttccttt 10800
ctgagattat gtggcttcac ttaatatcac acattctaag tccatccatt ttcatacagt 10860
ttttgtgatt tgatttttct tcagcactaa atagcattcc tttatatatt ttctgtttta 10920
ttcatgattt attatgcatt aattataatt tactacaaat gctacaaatg aaacaatcac 10980
acacccaaat taaccagatc cagagactgt acaattcagg gaccttctat ccagttacag 11040
tagtcatttg aaaaggaagc atggaacttc gcaaggattc tatactttat caaatatata 11100
tatatatata tatattttaa tcatatatat atattgcttg ctgatagaag gtgaaaattt 11160

-continued

```
cacctgcata aagaaatata tttgttttac ttgttaccgt atttatgggg agcaaagttg  11220
aagatgtaca aaccaggaat tttgttgata atagatttga aatccagcag gcaagcctca  11280
atggtatatg tagtgagcct ctctctctct ctctctctct ctctctctct ctctctctct  11340
ctctctgtgt atgtgcatgc atgtgcatgt atgcatgtgc gtgtatcatt aagtggtaat  11400
tttggcaagg acaaatatta gaaatatagt tcggaatttt accttaattt tctttcattt  11460
gatcaatagt caaatgtaaa tttttgcctt ccattttcat acacattact tttatcttcg  11520
gtctatctga atttaagaat tagaaatttg aaactcattc tctgatctct acatgcttac  11580
ctgtacaaaa caaaataaaa caacaaaaac aaaaccaaaa cccagactgt atgtgtgatt  11640
cacttttttt aaaacttgaa ctaggtccta ggattcttat aaagagtaaa gttaacaccg  11700
agctgatatt gaagattgaa aaaacctccc cttatatgga aactaccaga tcaataaacc  11760
agatgaatat cacatacaga cccaacttag ctgattcaaa ttttttaaag taaattacaa  11820
tatttataaa aataatcacc attttagaaa acgtagaagt ttcagacagg agaatcattg  11880
gttttaaaat cagcttgtgt aagttaacaa gatcttttct caaaatagac taaataaaag  11940
ctggcagtgg aatgggaaga acgaggctgt tgagtgatta gcacttgatg aacatatctg  12000
aagcccaggc tttcctcctc agtcccacat aaaccaaaac caaaaccgat tatcttctgg  12060
aaagaggagc tatgaaataa tcctcaactc tgggatgtgg gtggccttct gcactcgaag  12120
catgaacact aagaaaacca acgattgtag atagtatgaa cttgtcttaa gaatgtcctt  12180
tccagcacat gtcgagaaat gtaattagtt tcctgacctt attttattta ttaacatatc  12240
caaaatgctg tataatttct taatgtgtat ttgtcgtttt attccccttt taaaatgtga  12300
ttttttttta aaccaggttt gggtgcttca tgaaagagag cattacaggg actttgccaa  12360
gaatacaccg gacaggggcc atttctggtc attctttaaa acagtgtggc catcaattaa  12420
gtggtaagat gtggattttt tttccaacta aatttatgtt actagcactc aaactcagag  12480
tagtttttgc tgaaagtcta tactatgatg gacttttaga agagaacacc gagaaagata  12540
acagacggag cagcatcatg gacctaagga ggggtctttc ttcctgataa tgttcatgtc  12600
tttatcagtt gtaatgcacg gccttaaagg gcttccatta tctatagtac tcacacacaa  12660
tgtaagattt gtgggaaatg aatgtgtagt ccagataata ggtcttctgt tccatagcag  12720
acatttcaga taagattcag gacacatctc accccaaagt gaaccctgga gagtaagtca  12780
ttgtcaccac cagaactgat tgtgcccttt ccacatcaaa caacagttgg tattctctgg  12840
ggacaattta ggtggttaca actgggagag atggtactct atggtaatgg ccaaggttgg  12900
tgcagtcaga cacaacaaca acaaaaaaag ttctgaaaag ttctggcccc cactagggtc  12960
attgagaagg gtttaagata gtggctctca actgtcctta cgctgcagct ctttctcttg  13020
ttgtggtggc tcccaaccat aaactattta catcaccatt tcataactat aattttgcta  13080
ctcttatgaa tcataattat aaatatttgt gttttccagt ggtcttaggc aactcctgtg  13140
aaagggtctt tcaatccccc caaaaggggt catgacccac aggttcagaa atgctggctt  13200
aagagatctt gtttgtcact cagtccagac tgcaggactg agttctgtca atcttgctaa  13260
gcatactatt tcttgcaagg ggtgtaaatg caaggatgtt agagagcttt ctctcaggcc  13320
accattgtaa ctgatgtcct aggaaacaac atcctaattt ccacaccatc ttaaaggctt  13380
aatacaaaga gggcgtttta ataaaacgat gggggctgtt agaaagtgaa agtgctaaca  13440
aagaatgagt tgggttgtat cgtttagctt tgtttttaac gtcattcatt ccgtaggctc  13500
aaatttcaaa tgttctcatt ttgccccaat aacaacaacc ctctcaccac atatacagtc  13560
```

```
agagtctgaa acttaagctt tagggagtta atgaagggtg acaatggctt agttataaat  13620
actgcttcac tggtgtaata tcttctctat cttataagat caaacccata taccaatata  13680
acttgctgca tattatttga tgaaatgttg tgtctaatta ttgtgaccaa caacaaaata  13740
taaaaaaata gaaacattat gccttttcca aagctgctta gttgtcacat gccccctccc  13800
ccctagctta accttcttca ctgagtttgg ctctaaagtt tatttgcaac tttctcccaa  13860
ataccttga gaaagatctt caagttaaaa aatgtttgca ggaaccaatt ttagtaaaaa  13920
ctattgagag gcaggcttaa tatttacaga taatcattaa aaatatgttt tatttgtaac  13980
tacttcatcc caatcctcag ttcatttcct ttcttatctg aagcaaattt aaaagaaccc  14040
catttttatg atttacaatt ttctgccctg taaactgctg ggagcttagc acccctacac  14100
cctaacataa tgctttttca attagtttat atatacagtc tgtctcctgt gtttaaatta  14160
atttcacaat tcttagaaac ttatagttat gtacaataga atattgtttg tgctaacaca  14220
cacacacaca cacacacaca cacacactgc ttgcttaact aagaatctaa ttatgttgtc  14280
ttaaaaacaa aacctaagag cttaatttgg cttgatttct gttaaaagaa tcaactattt  14340
ttaacatgta agataaactt caatgaaggg atattttaaa taaactgaag aaacgtttta  14400
aaactggcgt gctagtgcat ggctataatc ccagcactag ggaagcaggg gcaaagaaca  14460
ttttaagttc aaagccagcc tgatctgaag tgggagatta ccacatccag catggcttgg  14520
gtcctggaaa actgagagga acatcaagag aataagaaag gacagacaca gagacccctg  14580
tccagagaag ctagaacagt gtgagctttg agcactgaac ctccaatccc cagagtgctt  14640
attagacaca gcacagtgga ggggttaact agtcacagag ggtgtctcc ctcttggtct  14700
ctcctcttgg tctgtaatca tcttggagta gaaggtgacg tcacggtaca cactggtcaa  14760
tagttcctaa acactgttgc tgagacccag ggaaggcttt gccgaagtcc catggggctg  14820
agccattggt ccttcacatg gctacggact tcaaactaca gatttcacct gctcctttca  14880
cagttactca gggcttccca tggttaccac aggagttcca agccagccag ttttgaaagg  14940
acaagaaagg gttcggtggc tgcggtggtg gtggtagtgg tgatggtggt taatagaatt  15000
taagaaagtt ttaaagcaag aaggaaaatg atttcattgt gcatataaat aaattgagat  15060
aatctgttaa agattcgaca cagatatcag tgttgtgact aacagtcaca aatcacaatc  15120
agacctgaat agatgaagga agagaaatag atgcagatcg tgattttgtt gatttgtctg  15180
ttttttgtt tcgttgttgt tgggttttgg tttggggttt ttgtttgttt gtttttgact  15240
cagaagtcaa aggctcgata tttgtcaatt actttgcgtc tctgtcacac actatcagga  15300
cggttgcttt cttggtttat caatacctct gatagccttc ttctgaaact gtattgttct  15360
gaattgttgc atatcccttg cagtttaaga agcagaataa cctgtgttta atgcaaaggt  15420
caggttaagc acacctgcgg tgagctaatg tctagcagca cttgataatt tagacacgtg  15480
ataaacattt taattcctgt acttaccagg gtggtcacaa aaatgggata ctagccttca  15540
aaatgactcc gagggctgag cagtttatct gtgtccaata tacatatatt ataatacata  15600
tatatacata tatgtatgta tatatatatg gtcgaatgtc tctctgtgtt tcatttcagc  15660
ttgccaccaa gacatatacg aaggactgga tatgagaggg tccaacttta atatatctaa  15720
gaccgacagt attgaagaat gccagaaact gtgcacaaat aatattcact gccaattttt  15780
cacatatgct acaaaagcat ttcacagacc agagtacagg tgagtgagtc atggttccct  15840
gagaggacat tccaggatgc atcagcatcc gcagtgaaaa agacaagtct gcttccctcc  15900
```

-continued

```
agtcaaagac aaggggtggg cagtcctgag ccccttcctt ccttaaattt cttagttaca  15960
tacttaattt cagtggaatt tcctcccaga gatagtgaac ttcgtttagt gactggtaag  16020
ctatgtatgg gcataatgtc agacaatgat gtccgccact ccatttgcag ccgcctgtcc  16080
cctttgcaga agggaaaagt gtctattgat cactaatggc ccaactgtgc ccctttgtgg  16140
taacaaatat tatctgcaca cctttgcaca cctcaaggaa ggaagcataa catcttttgt  16200
tgacactcag gaagagttgc ctgctgaagc gcagttcaag tggaacgccc accagtataa  16260
agccagtgga caacctggtg tctggattct cactgaagtc ctgtgctctc tcagagatcg  16320
gtaattagat gacgattatt cctctgtgtc tgtgatgtcc taaggaaggg ttcccagaaa  16380
catccacatg ctgttccccg ggacccagga atatgatgcc tttttataga tgtgattacg  16440
tggaaatagt ttgcaatcag agttatttgg gattaccaga atatgtgcct atccactctc  16500
aggggttctt agatgataaa gcgggtaaca gagaggtcag tgtcagaggt agatagactt  16560
gaaaggtgga acaagagtcc gaaagccaaa ggggtaccag tggtctgtag acattgaaaa  16620
ggacatagaa cagaggaaca gaagcaagcc aacctttgac tggcacccag gaagacttgc  16680
tttggccttc cagcctctag gaaaggtgat aaatttctgt tgctgtaacc tctagtttta  16740
ctataaatatg cctacaacaa catcattaga agaggaagct ccaccataaa gaaaaccaca  16800
agatcattct gtggtatccg tatccagaga aatatgcaca ttgtcgtgaa tcaaccaagc  16860
cctgtaactt cacacacaga ggtagcgcta aatgaattac ccggacagtt gccttcaaat  16920
ttaggacacc aaggtgtcag tggtgagatt tactgagacc agtccactta tagtaaatag  16980
taccaatact gaatgctggc cctacaccag gccctgtgtt aggtttccga attctgtggt  17040
atgacctctg tctgaaagac tgagaagtca gaagcaacat agctctttcc ctatttgtgt  17100
tttcttttct ctatgtgtcc ccaccaggct gtgccattca gatggcttaa atatattaac  17160
tatttaattt taatattccc cttttctagt ttttggaaac ttgtctatag gagatagggc  17220
tctttattca acagtgttcc cttttgtata ctgcgcttat cttagactgc accctgcagc  17280
tatagccaga tgccagagga ctgggaaaca ggcaatttaa aactcaggat gctgactgct  17340
gcaaatacca attgtcataa tcaccttagt ttctatgttg aaaagcaagc aaactccaca  17400
tcgtgtcact gagaaatgtt caccactgag ttcacaggtt gccccatgga tattttccag  17460
cactttgcct ttgcagacct gaatgtaagc catgtcgtca cccccgatgc cttcgtgtgt  17520
cgcaccgttt gcaccttcca tcccaactgc ctcttcttca cattctacac gaatgagtgg  17580
gagacggaat cacagaggtg agtgtcagca gcatatgctc ccttcttagc cttttccggt  17640
cctagcagag gcttgcaagg gtcttgctgg tttccctaac agcgctggag cctgtggttt  17700
aacaggatgc ttttcagacg ggtgcaggtt acttcgcaga ttagcagatt catcctcaca  17760
ctttccttct tccataaaac aaacgcgcta ttcactcaga ccacagtggc aggggcaaag  17820
ggagcaggca gcgttctcac tggcattaag gttgaggatt ggcttgggta acagctgctc  17880
atgcaatcca tcctttaatc ttgtgagaaa tccgagccct gcttaccctg atctagggtc  17940
tagtctgacc tcttcatctt tacacaacac ttcctttatg tataccctgg ggccggcaaa  18000
aggatgcgtg tggacgtaat accgcaggca gcataaatcc aaaccaacag tcctttgatg  18060
ccttctcttt ttctttttct aattagaagg tggactttaa tcctctgtcc tcttctctgg  18120
ctgtctgtac ttactaggtt tttttttttt tttttttttt ttttgccgga gggagaggtg  18180
gctccattta catttaagcc ctgtgatatt ttggagtctt gttgtctgac tgactgaaga  18240
gaatttctca gaatacaatt tacagagttg ctttaaaaag aaaggaagaa agaaagaagg  18300
```

taagtaggta ggtaggaagg aaggaaggaa agaaggaagg aaggaaggaa agaaggaagg 18360
aagggtgggt cttagtcagg gtttctattc ctgcacaaaa catcatgacc aggaagcaag 18420
ttgaggagga aaggaattat tcagcttaca catccacatc gctgttcatc accaaaggaa 18480
gtcaggactg gaactcacac agggcaggag gcaggagctg atgcagaggc catggaggga 18540
tgttacttac tggcttgctt cccctggctt gttcagcttg ctctcttata gaacccaaga 18600
ccaccagccc agggacggca ccacccacaa tgggctgggt ccttcccccct tgatcactgg 18660
ttgagaaaat gccttacagc tggtctcat ggaggcattt cctcaaggga gtctcctttc 18720
tctgtgataa ctccagcttg tgtcaagctg acacacaaaa ccaatctgta caggaaggaa 18780
ggaaggaaag aaagaatatg tctagtgctt ctaatgctgt cttctttctc tttcttgttt 18840
atttttaata ggaatgtttg ttttcttaag acatctaaaa gtggaagacc aagtccccct 18900
attattcaag aaaatgctgt atctggatac agtctcttca cctgcagaaa agctcgccct 18960
ggtaatgtca ctcaacctcg atggcgtgtg acttgtgtcc tggtttggtt cttggttgct 19020
gtaataaata ccatgaccaa aagcaagttg gggaggagag aggtgttttg ttcacatgtc 19080
cctgttatag ccgattcctg agggaagtca ggctaggaac tcaagcagag gcaaagacag 19140
gaactgagca tagacctcag agaaatgctg cctttttgac ttgctcctgt gattgatcat 19200
atatgtgtat gtgtatgtat gtgtatgtgt gtgtttgtgt gtgtatgtgt atatgatgtg 19260
tagatgacgt atgtatatgt gtatgagttt gtgtgtgtgt ttgtgtatat gatgtgtaga 19320
tgacgtatgt atatgtgtat atgtgtacgt gtttgtgtgt gtatgtgtat atgatgtgta 19380
gatgtatgta tatgtgtatg tgtttgtatg tgtgtttgtg tgtgtatgtg tatatgtata 19440
ggttgtagat gtataagtat acgatgtata tgatgtatgc atcatgtgca tatgatgtgt 19500
gtgtgtgtgt gtgtgtgtgt gtatcagtag cccatgacca cctgcccaga gtggatactg 19560
ccccccagtt ggctgaccct cttctttcca tcattaatcc aaagaacatc ccatagacat 19620
tcctttaagt tagcctgagg gaggcaattc ttcaagggat gttccatctt ttcaggtgac 19680
tcttttatgt caagttgaca aacactaggt gtaccacatc ttgggagcct ctaagagtta 19740
atgaaatggg tctcaagtcc ctagaaacgt tgccaatatg ccttatgtcc tgacttgtca 19800
tatctccttt ggtgtttgta tgtggtgcag aaccctgcca tttcaagatt tactctggag 19860
ttgccttcga aggggaagaa ctgaacgcga ccttcgtgca gggagcagat gcgtgccaag 19920
agacttgtac aaagaccatc cgctgtcagt tttttactta ctcattgctt ccccaagact 19980
gcaaggcaga ggggtaaggg aacctttctt taacgataat cagcaaggta atttttttct 20040
agttttctct ctctgtgggt ttaattttgt actgttcatt tttttccagg tgtaaatgtt 20100
ccttaaggtt atccacggat ggctctccaa ctaggatcac ctatgaggca caggggagct 20160
ctggttattc tctgagactg tgtaaagttg tggagagctc tggtgagtga agctcacttg 20220
ttatggaact gcatggctgg cttgactgct gtgatgaatg tcttggtctt atataatggg 20280
attgtttata tggtttctgt tatggtttgt atgtgcttgg cccagggtgt ggccctgttg 20340
gagtaacttg ttggagtggg tgtgtcactg tgggtatggg ctataagacc ctcatgctag 20400
ctgcctggaa gtcagtattc tgctagcagc cttcagatga aggcaccatg catgcctgga 20460
tgccgccatg ttcccatctt ggcgataatg gactgaacct ttaaacctct aaaccagctc 20520
caattaaatg ttgtctttat aagagttgcc ttggtcatgg tgtctgttcg cacagtaaaa 20580
accctaacta agacagtttc cttggataaa gggagggaat gctgatctgt gtctaattct 20640

-continued

```
gccacacatc tcaacacttt tcagactgta cgacaaaaat aaatgcacgt attgtgggag  20700
gaacaaactc ttctttagga gagtggccat ggcaggtcag cctgcaagta aagttggttt  20760
ctcagaatca tatgtgtgga gggtccatca ttggacgcca atggatactg acggctgccc  20820
attgctttga tgggtaagtt ttcgatccat cttattttac caatgtgtgt gtgtgtgtgt  20880
gtgtgtgtgt gtgtgtgtgt gtgtgtgtgt gtgtgagcat gcacgtgtat ggacccttac  20940
ctgcacatgt gtatataaag aggttagcct caggtatctt cgtgtactgc ttgcttttct  21000
tatttgttga gacagggttg ttcactgagt ctagtgctaa cccttttgac tagactggct  21060
gcacagccag tcccagagat ctgtctgcct ctgtctcccg gcacattctt agccctagtt  21120
cagtgttggg gctctgaact tgaatgttca tgtttgagaa gcaagccctt tgcccactta  21180
gccatctcct tggccctgag gcatttgttt tgatgataat aaaagtttcc aagcctttgt  21240
ctagaaaata ttatgatttt aaatttagct tatatatctt ttacatggtc aatttaaaat  21300
tcaaaagata tgtaggtaca ttttaagcaa caaaataacc ttaattccta ctggggctta  21360
ttttaatcgt tacagctgct tgatggctct gatgtaatga aagcaattgc ttttaggtct  21420
ggtaaactga acttaattct cctaaagctt cttcaaaagg cacagaagca ttcccgtatt  21480
tttacttgta ataaatataa agcaattgtt aagtttgttt tgagtatttt caaccacagc  21540
ttttatactg tgctctgtaa tcctatatgg acacagttca gctgaatatg agcccctcaa  21600
agattttaga aacagtaaag ggatcctgaa ggaacactga ccaaaattca atcaaaataa  21660
aatgttatga caaacctgag gcattctgag aatcctctcc tgtgcatatt tcaggactcc  21720
actgggtttg taaacataca acatgcttac tgtgcactgt gcatgccacc atgctgtgta  21780
gtaccaacag atggtaccct aaagacaatc agactgaaga ttatgtaatg ttgtgaacca  21840
tggtgtctgt agtacgtgtg ccttaggttt tctgctctta caaaacataa gagtttaatt  21900
tcaaagaaca aaagcattaa aatgtgtctt gtcacagtcg cctttgggtt gtacagtgtt  21960
aaactttgat tttcaacatt gtttcataaa aactcattga atgaacttgg gtttgggtat  22020
tagagtttcc aaagctttct aaatggtcct taatctaaga ctatcatttg gtcctccata  22080
tgtatgtgaa gtggtgttct tagcattatc agttataaaa gtaaaatatt aagaaactct  22140
taaaagcatt gaggatgttc tttgtcttat agtatcaaat attcagacat attttaatta  22200
tgtatgtcga cataaataaa cacgttattc tattaagatg tgcatttgct gataagtggt  22260
aaaattatct gtgcaccaaa aattgtcttg tagtaagttt ctttataata tatcatcagt  22320
aaatgtttaa tatgtgtgcc tgcttcatgt aatcacacac aaaaacaaaa aattatcttt  22380
tcaggcaaaa gggagtctca catggacaaa gttttattat aaactaaatc ttcgaagtcc  22440
aatactgctg ctgtaaacaa caataggtgg ccttgccaga aaaagtaact aggtcatatg  22500
gaatgttttc gttcttctcc ctcctcccct tcaaagaaat gtgctaagaa aaaggagcaa  22560
ggaaggatgc caacgttact ttgttctcct gcttctctcc taggattccc tatccagacg  22620
tgtggcgtat atatggcggg attcttaatc tgtcagagat tacaaacaaa acgcctttct  22680
caagtataaa ggagcttatt attcatcaga aatacaaaat gtcagaaggc agttacgata  22740
ttgccttaat aaagcttcag acaccgttga attatactgg tatgcagcgt atttaagggg  22800
aaactgtaca attcacttgt attggcgtta gcttccagtt caatttgagc gagaagacag  22860
atctgcagca attgtctttg tgtcctggtt ggtggggctg agggagagat gaggctgcct  22920
gggaagtaaa aaccccacga cctaccatgc atttgctgct acttaagggg gcaaaagagc  22980
ttcattactt tctcagagtg caacggagtg tatggtattg aaacagttgg tatagggaag  23040
```

atttgacat ctggggacat tgggtatctt ttgacaagat tggcaggatg actcttgctt 23100
gggcttagga atatacaact atatgaacat gaatgggact agaggttagt gcctaagaag 23160
acactgggct gacagtggag gaacatgaag aatggaactg ccattggtgg cacatcactc 23220
cacagaaaca gaatgcctgc caataccatt agctgcaagt gtctgctaac agtcatgtgt 23280
ccttagacag ctcgcctttc ttccttccac ctctaatatc cactgtatgt gtgctgacta 23340
cttcattgct ttcttgcaat aattaagcaa gatattcaag taaaatacca ggacagcatg 23400
gctatgtttg ctctgcttct gaattctgtt acagtgtagg tttaccaaag cataaggatg 23460
tttaccaata cattttggtt gaagagtccc tcttccccat ggaaatttca ttctgaaatg 23520
ccattcaaac tgtgagaatt tccttgaatc atgggcttta gaaatggctg gagggccatt 23580
ctttatactc tttagtttca gcaatggttt cattatatct catacatggg catggtatgt 23640
tttgattgca tgcacccct tcaccctctc ttgcccttcc cactcctgtt gttcgcccta 23700
ctcctcccgt gtagtcccac atggctcatt cttgctctgt tgctttgtag aaaaagaata 23760
aggcaaaaga tagatattaa tttttcagat ccctatctat ggttttaatt agcctaaatc 23820
tattcatgaa attttctttc agaattccaa aaaccaatat gcctgccttc caaagctgac 23880
acaaatacaa tttataccaa ctgctgggtg actggatggg gctacacaaa ggaacgaggt 23940
aagcctggca tgtggaatgt tcctctctta tgtgctaagg tacatggagt agagccactc 24000
aacaacccgt agtcatgatc cttctgtaga tccattcaac agcccttact catggccttt 24060
ctgttcattc caaaatgatc ccaagaatat gactttttg cattaaaaac tgatgagcta 24120
atccattaaa catattactc ataatagaga tcattttcat gactctgcat caagaactgt 24180
aaccctatgg tgctcttaag tccactgaag ctcatctgat ccccagttct cacagcatcc 24240
ctgtttacta tgctctccct tgctatgaat agccaaagtg ccagcatctc tttaaggaca 24300
gtgccatata tatatatata ttatagtata gtagtgccaa atatatatat ttgtagtata 24360
ataaatctaa ctttccctct aattatgctg ttaacttctt gtgtaaaata catagattca 24420
taaagacaag tagattgcag cacaattgcc attattttta gcagaatttc acacagggat 24480
aaacatacat ctgtattaat gtaatcctta gcaagttgtt tgaatatcta ccataatgtt 24540
taaataacta tgcacaagaa caatatcttc ctttctgttg taactacaat tcaaagaatc 24600
cgtgactctt acacagcagt gctggtgaca atatcacact tccgtatttg ttatctgcat 24660
ttgaaacaga gggtggggtt cagccttact tggaagggag agactgtaga ggccagtttt 24720
tctccttccc ttcctcggag tttatggata gatcagttgt atgcgtggct ctcaaatcaa 24780
gggatctgtg tgttaagact tgagacattt ctctagaaat aagcatgttt tccttttaga 24840
ctgagtgcca gatagcatgt ttgagtgatt tttttaaaaa aagagatgat tggctgtgtc 24900
ttctttatat tttctgaacc agttagtact gtattcaatt aatcctcatt ttcactatgt 24960
tgacttggct acaaatacgt ggacacacac atatacatgt gtgcacatgc acacacatac 25020
acacacatac atatacacac atacatacat acaaccaaga aatatagaaa tgggtgtaga 25080
acaaaatact tctctgctgt taaatgtttg ggatttattt tcataaattg tatatttgtg 25140
ttataatttg aatttataaa acaatgaaag gcaagagcat ccacgtatta aaggtacaaa 25200
tgtttaaaac aacatatttt tctgaggaga gccttggttg atacaggagg atggctgaga 25260
tcatagaaac caagtctgtg gtagcttggg tgatagggga gcttcagtca acacagatca 25320
ttgcttcttc atctccatct ccctcccctg ctctccctcc acttcttgct tcctttctcc 25380

-continued ctccctcttt ctcccctact tattgtattt cctctcttta atgctacttc ctgattgctt 25440
cataggtgag acccaaaata ttctacaaaa ggcaactatt cccttggtac caaatgaaga 25500
atgccagaaa aaatatagag attatgttat aaccaagcag atgatctgtg ctggctacaa 25560
agaaggtgga atagatgctt gtaaggtaac tctgggaaaa atacgtaata gttcactgga 25620
gactgctcat ccaaaagcaa atttcccaag ttacatttca ttagtttcag ttttgaagtt 25680
gcagagttaa gtgacatgga gacttttttt tttttaaaga tttattttta tttatgtgag 25740
tgtacactgt cactgttttc accagaagag ggcatcggat tccattacag atggttgtga 25800
gccaccatgt ggttgctggg aattgaactc agaacctctg gaagagcagt cagtgctctt 25860
agctgctgag ccatctctct agccccagac ctggagactt tttaaacagc ctttaacaaa 25920
ctaaacacac acaatgcaca tcatgtgttc cttataatag ttacgttaga atttgtattg 25980
actgtgacgg gtgtgtcaca gtcagtacag ggacatgcca tatttaagga caattttaca 26040
tacatggtca tgctaaaata caaggaaaca gatttatttg aactttgggt aaagatgcta 26100
aaattgttgg gtttatctga gaacgggaga gggaataaat tggccttgta accatccact 26160
tactttcttc atggctaatg gggtgcagag aaattgagaa gttgcatgtg tgatatgtaa 26220
aatatgatag caaaatgtta aagacatcta tctttgaaca aggggctcct aatttgaatc 26280
atcactgtta tagctctcta tcattttttt tctactcact gtgatccagg gagattccgg 26340
tggcccctta gtttgcaaac atagtggaag gtggcagttg gtgggtatca ccagctgggg 26400
cgaaggctgt gcccgcaagg agcaaccagg agtctacacc aaagttgctg agtacattga 26460
ctggatattg gagaagatac agagcagcaa ggaaagagct ctggagacat ctccagcatg 26520
aggaggctgg gtactgatgg ggaagagccc agctggcacc agctttacca cctgccctca 26580
agtcctacta gagctccaga gttctcttct gcaaaatgtc gatagtggtg tctacctcgc 26640
atccttacca taggattaaa agtccaaatg tagacacagt tgctaaagac agcgccatgc 26700
tcaagcgtgc ttcctgcctt gagcaacagg aacgccaatg agaactatcc aaagattacc 26760
aagcctgttt ggaaataaaa tggtcaaagg atttttatta ggtagtgaaa ttaggtagtt 26820
gtccttggaa ccattctcat gtaactgttg actctggacc tcagcagatc acagttacct 26880
tctgtccact tctgacattt gtgtactgga acctgatgct gttcttccac ttggagcaaa 26940
gaactgagaa acctggttct atccattggg aaaaagagat ctttgtaaca tttcctttac 27000
aataaaaaga tgttctactt ggacttgatg ggacagagca ccttttcata taaaccacct 27060
ttctggccat tgctgctgag tcctgcatgg tcatgagtaa ggagctcgtg acagggtttc 27120
ccacccctgg agcaaaacca gctagatgtt aggcttgttt gtataaattt caagttcctc 27180
ctttgggaag tattctctct gcctagatta ttgggggaat atcctctctg tcagggcagc 27240
ccttaagatt gtgggaaaca tgagaatata taatttctct acaatgcaaa atataaggat 27300
acagtctgaa ttatataagg agatccatgg acctaagaga acagaggcag ctacactatg 27360
agccagcttg tcagaaagat actactgaag gagttaaaga gataaagaga tttggggaat 27420
agctatcaca gggcaagatc ccacccagct aagtttatta tttgtgttta caaagacagc 27480
cagattcctg agttcaaggt catcctggga cagagctggt ttaggcccag ggtaatgggg 27540
gtcccactca gctagcttat tgtctatgct tttaaatgca ggcagatttc tgaattcatt 27600
tgccatgtta aaaaaaatgt acctgatgtc ttttcctaag atatacgggt ctagagtcat 27660
ggaatgctga ttcatgggtt aatcaaaagg gaacctagag taaacgcctg tactgataga 27720
tacataaaag tctgggcttt ggtctacaaa tgttgagcta tgtggatgag ctgtgtagag 27780

-continued ctaaagattg aacagtggtc tctaattatt tttttagatt attttttttct agcagctacc 27840 cagagagaac ggcttagaga gtaaatattg ctattttaga tttttttttc tagaaaatcc 27900
aagaattttt atagcagctt ttctgacact ggtcagaaaa cccatgagct atccagaaag 27960
cttttagatt tttttttttc aagagagaac tgtctcaagt agagacagct ctctcaatca 28020
gagagagctg cctggagcag aaagctatct cgatcagact acagagccaa gagctattta 28080
caaagagctg tctagggagc cattttaagc aggctataag gctgtcagct tgcaccccat 28140
catttgactt tgagttgttt ctttcaccac tctcaaacac cccttctctc aggaactcct 28200
ctccaagcca agactggttc ttggcacatt gccacatggt cttggctacg tatgcatgta 28260
agacctgtag ggctatattt ttcttcttgt gtgcagctcc aacaataggc ttatcacaca 28320
gtactcatac agggcacgga atctgatgag aatctccccc agggaaccct ttggagttcg 28380
gttgatactg tattctgcaa tagtaattca tggaatgtca ttggatgtaa agtgttgtat 28440
aaaattcagg cttgtagttg agttgaaagt aaaaagcaat cttggaaggg atgacagtaa 28500
tcctcatgta agacaaattt ccagcttccc agtgattcat aaagtggacc atatgggctt 28560
aactccattt agttaagctg attaatattt agaattagcc atttacaaac tattgtgcaa 28620
gttaaataga caaacagaaa agtgaaattt cctaaagaag attaaacctt tcactgcaaa 28680
ggtttgttga gtagtgcaga ggattaaata tggaaaagcc agtgggttat ccacagaatt 28740
tgccacggga agtggaggag gtggttatta tctgaggagc aaataaatgg cttttgtaaa 28800
atctgtctgg attcccatga aatcactccc ctttaaagca caccacttca acttttaatt 28860
ttgtatacaa tttcatctta atctgttctg tgtggaagtt attttatatt taaaatgaaa 28920
gaagtggttc tcaatgaaaa tcacgtatct caggatttca tactgataac cctaacaggt 28980
gttcacacaa ggtgtcagag tgctggctgg gtagaccttg ggctttggtt tctcaaggaa 29040
tggcctcatt tgatctaaac agttttgaaa tgtttaattt ccctggggca taaagtaaca 29100
ttataacatt gccagtggga gtccagttag attggaaggc tctgtttatt ttttgttgtg 29160
tgttccagca caaagtagcc tgtcttccac ttggggcctt atggggctag tgagaaagtg 29220
agaggcttga ataacatcac tgtcacaagg cagagaggag gcaggaggcc ctagatcttt 29280
ggcaggtcca tccaaaaaag ggagtgttat ctctgggaaa gaacacggtt cttcctgggt 29340
cacacatgca gaacacactg catactgttc acatgtgtgg agttcaaccc aaagctcaga 29400
gggctgtctc tcatcgttga cttttcttct tgtaattctt gcttatgcct gccagcccta 29460
tagattgtca gtaactagga aggaggttct ccctgactct gtctctctct ttcatcaata 29520
ctacatgtga atgagcatgt ggcacatgtc tccctttaga tttaccttta ttatctttgt 29580
tgatgtgttg tttaattgta tgtcacgtgg ttgctagtgc ctgacaccaa ctgatcaaag 29640
cgtaacttct gagcaactgc cttctaccag agtaaaatag agtagtcctt catgtcaaga 29700
tctcttcaaa gtcatacaca ggcacacaca catggacaca catgcaggaa agcatggaca 29760
cacatacaca tacacatgca tacacacgtg ttgtagttac cattattttg agtgtttact 29820
ataccccctt tttgccttta actatttatt aggtatttct accctacttt agataattta 29880
gttcccaaat aaaagacaca ggaatctttg gatttagaat aaactttaga gcactgggca 29940
gatatcaacc ctctatgcta tcttgtctgt ttccctatca aattgctgga gatactactt 30000

<210> SEQ ID NO 16
<211> LENGTH: 2252
<212> TYPE: DNA

<213> ORGANISM: Macaca mulatta
<220> FEATURE:
<221> NAME/KEY: misc_feature
<222> LOCATION: (830)..(939)
<223> OTHER INFORMATION: n is a, c, g, or t

<400> SEQUENCE: 16

```
agaacagctt gaagaccgtt catttttaag tgacaagaga ctcacctcca agaagcaatt     60

gtgtttgcag aatgatttta ttcaagcaag caacttattt catttccttg tttgctacag    120

tttcctgtgg atgtctgact caactatatg aaaacgcctt cttcagaggt ggggatgtag    180

cttccatgta cacccgaac gcccagcact gccagatgat gtgcacattc cacccaaggt    240

gtttgctatt cagttttctt ccagcaagtt ccatcaatga catggagaaa aggtttggct    300

gcttcttgaa agatagtgtt acaggaacct tgccaaaagt acgtcgagca ggtgcaattt    360

ctggacattc cttaaagcag tgtggtcatc aaataagtgc ttgccaccga gacatttata    420

aaggaattga tatgagagga gtcaatttta atgtatctaa ggttagcagt gttgaagaat    480

gccaaaaaag gtgcaccaat aacattcgct gccaattttt ttcatatgcc acacaaacat    540

ttcacaatgc agagtaccgg aacacttgcc tcttaaagca cagtcccgga ggaacgccta    600

ccactataaa ggtgctgaat aacgtggaat ctggattctc actgaagccc tgtgcccttt    660

cagaaattgg ttgtcacatg aacatcttcc agcatcttgc cttctcggat gtggatgttg    720

ccagagttct cgccccagat gcttttgtgt gtcgaaccat ctgcacctat catcccagct    780

gcctcttctt tacgttctat acgaatgcat ggaagatcga gtcacaaagn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnna accctgccat tctaaaattt    960

acccgggagt tgactttgga ggagaagaat tgaatgtgac tttcgttaaa ggagtgaatg   1020

tttgccaaga gacttgtaca aagatgattc gctgtcagtt tttcacttac tctttactcc   1080

cagaagactg taaggaggag aagtgtaagt gtttcttaag attatcttcg gatggttctc   1140

caactaggat tacatatggg acacaaggga gctctggtta ctctttgaga ttgtgtaaca   1200

ctggggacag ctctgtctgc acaacaaaaa caagctcacg cattgttgga ggaacaaact   1260

cttcttgggg agagtggccc tggcaagtga gcctgcaggt gaagctgatg gctcagaggc   1320

acctgtgtgg agggtcactc ataggacacc agtgggtcct cactgctgcc cactgctttg   1380

atgggcttcc cttaccggat gtttggcgca tttatagtgg cattttaaat ctgtcagaca   1440

ttacaaaaga aacacctttc tcacaaataa aagagatcat tattcaccaa aactatagaa   1500

tctcagaagg gaatcatgat atcgccttaa taaaactcca ggctcctttg aattacactg   1560

aattccaaaa accaatatgc ctaccttcca aaggtgacac aaacacaatt tataccaact   1620

gttgggtaac tggatggggc ttctcgaagg aaaaaggtga aatccaagat attctacaaa   1680

aggtaaatat tcctttggta acaaatgaag aatgccagaa aagatatcaa gattataaaa   1740

taacccaacg gatggtctgt gctggctata aagaaggggg aaaagatgct tgtaagggag   1800

attcaggggg tcccttagct tgcaaacaca atggaatgtg gcgtttggtg ggcatcacca   1860

gctggggcga aggctgtgcc cgcagggagc aacctggtgt ctacaccaaa gtcgctgagt   1920

acatggactg gattttagag aaaacacaga gcagtgatgg aaacgctcgg atgcaggcgc   1980

cagcatgagg agcagcccag agtcttggcg agttttacaa cctgggttca agtcaaattc   2040

tgagcctggg ggtcctcatc tgcaaagcat ggagagtggc atctactttg catcctgtca   2100

taaggacaaa agacagtgca ctcagagctg ctgaggacaa tgttttgctg aagccagctt   2160
```

tcagcattca gtaactggga gctgataatg tgaagtcgca accgagatct ccatgattgt 2220
gtgtcgtaaa ataaaatggt aaaagatcac aa 2252

<210> SEQ ID NO 17
<211> LENGTH: 2353
<212> TYPE: DNA
<213> ORGANISM: Macaca mulatta
<220> FEATURE:
<221> NAME/KEY: CDS
<222> LOCATION: (238)..(2109)

<400> SEQUENCE: 17

```
ggaagccgtt cactagtcag attgaccaga gattatgggt gggctgtctg ttggggtcta      60

tgcacaggat ttctgttgga gttctaagga caaaaagttg aaactgttgg cagaaaccca     120

aagtcaatat cgaagccaag gaaaacattg cctgcggtgc cacattagaa cagcttgaag     180

accgttcatt tttaagtgac aagagactca cctccaagaa gcaattgtgt ttgcaga        237

atg att tta ttc aag caa gca act tat ttc att tcc ttg ttt gct aca       285
Met Ile Leu Phe Lys Gln Ala Thr Tyr Phe Ile Ser Leu Phe Ala Thr
1               5                   10                  15

gtt tcc tgt gga tgt ctg act caa cta tat gaa aac gcc ttc ttc aga       333
Val Ser Cys Gly Cys Leu Thr Gln Leu Tyr Glu Asn Ala Phe Phe Arg
            20                  25                  30

ggt ggg gat gta gct tcc atg tac acc ccg aac gcc cag cac tgc cag       381
Gly Gly Asp Val Ala Ser Met Tyr Thr Pro Asn Ala Gln His Cys Gln
        35                  40                  45

atg atg tgc aca ttc cac cca agg tgt ttg cta ttc agt ttt ctt cca       429
Met Met Cys Thr Phe His Pro Arg Cys Leu Leu Phe Ser Phe Leu Pro
    50                  55                  60

gca agt tcc atc aat gac atg gag aaa agg ttt ggc tgc ttc ttg aaa       477
Ala Ser Ser Ile Asn Asp Met Glu Lys Arg Phe Gly Cys Phe Leu Lys
65                  70                  75                  80

gat agt gtt aca gga acc ttg cca aaa gta cgt cga gca ggt gca att       525
Asp Ser Val Thr Gly Thr Leu Pro Lys Val Arg Arg Ala Gly Ala Ile
                85                  90                  95

tct gga cat tcc tta aag cag tgt ggt cat caa ata agt gct tgc cac       573
Ser Gly His Ser Leu Lys Gln Cys Gly His Gln Ile Ser Ala Cys His
            100                 105                 110

cga gac att tat aaa gga att gat atg aga gga gtc aat ttt aat gta       621
Arg Asp Ile Tyr Lys Gly Ile Asp Met Arg Gly Val Asn Phe Asn Val
        115                 120                 125

tct aag gtt agc agt gtt gaa gaa tgc caa aaa agg tgc acc aat aac       669
Ser Lys Val Ser Ser Val Glu Glu Cys Gln Lys Arg Cys Thr Asn Asn
    130                 135                 140

att cgc tgc caa ttt ttt tca tat gcc aca caa aca ttt cac aat gca       717
Ile Arg Cys Gln Phe Phe Ser Tyr Ala Thr Gln Thr Phe His Asn Ala
145                 150                 155                 160

gag tac cgg aac act tgc ctc tta aag cac agt ccc gga gga acg cct       765
Glu Tyr Arg Asn Thr Cys Leu Leu Lys His Ser Pro Gly Gly Thr Pro
                165                 170                 175

acc act ata aag gtg ctg aat aac gtg gaa tct gga ttc tca ctg aag       813
Thr Thr Ile Lys Val Leu Asn Asn Val Glu Ser Gly Phe Ser Leu Lys
            180                 185                 190

ccc tgt gcc ctt tca gaa att ggt tgt cac atg aac atc ttc cag cat       861
Pro Cys Ala Leu Ser Glu Ile Gly Cys His Met Asn Ile Phe Gln His
        195                 200                 205

ctt gcc ttc tcg gat gtg gat gtt gcc aga gtt ctc gcc cca gat gct       909
Leu Ala Phe Ser Asp Val Asp Val Ala Arg Val Leu Ala Pro Asp Ala
    210                 215                 220
```

```
ttt gtg tgt cga acc atc tgc acc tat cat ccc agc tgc ctc ttc ttt      957
Phe Val Cys Arg Thr Ile Cys Thr Tyr His Pro Ser Cys Leu Phe Phe
225                 230                 235                 240

acg ttc tat acg aat gca tgg aag atc gag tca caa agg cga gta tgc     1005
Thr Phe Tyr Thr Asn Ala Trp Lys Ile Glu Ser Gln Arg Arg Val Cys
                245                 250                 255

atg gct agc act tgc tgc tgt act ttc atc aat ttt att tta gaa act     1053
Met Ala Ser Thr Cys Cys Cys Thr Phe Ile Asn Phe Ile Leu Glu Thr
            260                 265                 270

tta cct gaa ccc tgc cat tct aaa att tac ccg gga gtt gac ttt gga     1101
Leu Pro Glu Pro Cys His Ser Lys Ile Tyr Pro Gly Val Asp Phe Gly
        275                 280                 285

gga gaa gaa ttg aat gtg act ttc gtt aaa gga gtg aat gtt tgc caa     1149
Gly Glu Glu Leu Asn Val Thr Phe Val Lys Gly Val Asn Val Cys Gln
    290                 295                 300

gag act tgt aca aag atg att cgc tgt cag ttt ttc act tac tct tta     1197
Glu Thr Cys Thr Lys Met Ile Arg Cys Gln Phe Phe Thr Tyr Ser Leu
305                 310                 315                 320

ctc cca gaa gac tgt aag gag gag aag tgt aag tgt ttc tta aga tta     1245
Leu Pro Glu Asp Cys Lys Glu Glu Lys Cys Lys Cys Phe Leu Arg Leu
                325                 330                 335

tct tcg gat ggt tct cca act agg att aca tat ggg aca caa ggg agc     1293
Ser Ser Asp Gly Ser Pro Thr Arg Ile Thr Tyr Gly Thr Gln Gly Ser
            340                 345                 350

tct ggt tac tct ttg aga ttg tgt aac act ggg gac agc tct gtc tgc     1341
Ser Gly Tyr Ser Leu Arg Leu Cys Asn Thr Gly Asp Ser Ser Val Cys
        355                 360                 365

aca aca aaa aca agc tca cgc att gtt gga gga aca aac tct tct tgg     1389
Thr Thr Lys Thr Ser Ser Arg Ile Val Gly Gly Thr Asn Ser Ser Trp
    370                 375                 380

gga gag tgg ccc tgg caa gtg agc ctg cag gtg aag ctg atg gct cag     1437
Gly Glu Trp Pro Trp Gln Val Ser Leu Gln Val Lys Leu Met Ala Gln
385                 390                 395                 400

agg cac ctg tgt gga ggg tca ctc ata gga cac cag tgg gtc ctc act     1485
Arg His Leu Cys Gly Gly Ser Leu Ile Gly His Gln Trp Val Leu Thr
                405                 410                 415

gct gcc cac tgc ttt gat ggg ctt ccc tta ccg gat gtt tgg cgc att     1533
Ala Ala His Cys Phe Asp Gly Leu Pro Leu Pro Asp Val Trp Arg Ile
            420                 425                 430

tat agt ggc att tta aat ctg tca gac att aca aaa gaa aca cct ttc     1581
Tyr Ser Gly Ile Leu Asn Leu Ser Asp Ile Thr Lys Glu Thr Pro Phe
        435                 440                 445

tca caa ata aaa gag atc att att cac caa aac tat aga atc tca gaa     1629
Ser Gln Ile Lys Glu Ile Ile Ile His Gln Asn Tyr Arg Ile Ser Glu
    450                 455                 460

ggg aat cat gat atc gcc tta ata aaa ctc cag gct cct ttg aat tac     1677
Gly Asn His Asp Ile Ala Leu Ile Lys Leu Gln Ala Pro Leu Asn Tyr
465                 470                 475                 480

act gaa ttc caa aaa cca ata tgc cta cct tcc aaa ggt gac aca aac     1725
Thr Glu Phe Gln Lys Pro Ile Cys Leu Pro Ser Lys Gly Asp Thr Asn
                485                 490                 495

aca att tat acc aac tgt tgg gta act gga tgg ggc ttc tcg aag gaa     1773
Thr Ile Tyr Thr Asn Cys Trp Val Thr Gly Trp Gly Phe Ser Lys Glu
            500                 505                 510

aaa ggt gaa atc caa gat att cta caa aag gta aat att cct ttg gta     1821
Lys Gly Glu Ile Gln Asp Ile Leu Gln Lys Val Asn Ile Pro Leu Val
        515                 520                 525

aca aat gaa gaa tgc cag aaa aga tat caa gat tat aaa ata acc caa     1869
Thr Asn Glu Glu Cys Gln Lys Arg Tyr Gln Asp Tyr Lys Ile Thr Gln
```

-continued

```
    530                 535                 540

cgg atg gtc tgt gct ggc tat aaa gaa ggg gga aaa gat gct tgt aag      1917
Arg Met Val Cys Ala Gly Tyr Lys Glu Gly Gly Lys Asp Ala Cys Lys
545                 550                 555                 560

gga gat tca ggg ggt ccc tta gct tgc aaa cac aat gga atg tgg cgt      1965
Gly Asp Ser Gly Gly Pro Leu Ala Cys Lys His Asn Gly Met Trp Arg
                565                 570                 575

ttg gtg ggc atc acc agc tgg ggc gaa ggc tgt gcc cgc agg gag caa      2013
Leu Val Gly Ile Thr Ser Trp Gly Glu Gly Cys Ala Arg Arg Glu Gln
            580                 585                 590

cct ggt gtc tac acc aaa gtc gct gag tac atg gac tgg att tta gag      2061
Pro Gly Val Tyr Thr Lys Val Ala Glu Tyr Met Asp Trp Ile Leu Glu
        595                 600                 605

aaa aca cag agc agt gat gga aac gct cgg atg cag gcg cca gca tga      2109
Lys Thr Gln Ser Ser Asp Gly Asn Ala Arg Met Gln Ala Pro Ala
    610                 615                 620

ggagcagccc agagtcttgg cgagttttac aacctgggtt caagtcaaat tctgagcctg    2169

ggggtcctca tctgcaaagc atggagagtg gcatctactt tgcatcctgt cataaggaca    2229

aaagacagtg cactcagagc tgctgaggac aatgttttgc tgaagccagc tttcagcatt    2289

cagtaactgg gagctgataa tgtgaagtcg caaccgagat ctccatgatt gtgtgtcgta    2349

aaat                                                                 2353


<210> SEQ ID NO 18
<211> LENGTH: 33001
<212> TYPE: DNA
<213> ORGANISM: Macaca mulatta
<220> FEATURE:
<221> NAME/KEY: misc_feature
<222> LOCATION: (17364)..(18312)
<223> OTHER INFORMATION: n is a, c, g, or t
<220> FEATURE:
<221> NAME/KEY: misc_feature
<222> LOCATION: (23228)..(23609)
<223> OTHER INFORMATION: n is a, c, g, or t

<400> SEQUENCE: 18

actgttggaa agacatcatt ggttttgaaa tctgaaaagg acgtgagatt tgggaaaggc      60

caggggaaga atgatatagt ttggctccat gtccccaccc aaacctcatc ttgaattgta     120

atccctgcat gttgaaggag gggcctggtg ggaggtgata ggatcattgg ggtggtttcc     180

cctgtgctgt gttctcatga tagtgaggga tttaaaagta gctgtttccc ctgcacatgc     240

acactctgtc tctcctatca ccttgtgaag aaggtgtctg cttcccctct gccttccatc     300

atgattataa gtttcctgag gcctccccag ccatgggtaa ccgtgggtca gttcaacctc     360

ttttgtttat aaattgccca gtctcaggta gtatctttac agcaatgtga aactgaacta     420

atacatctgg gaaattcttt ttctctcctt cctttctgaa ggacagcttt gcctgatatt     480

atattcctgg ttgccaggtt ttgtactttc agtactttga atatatcatc ccattctctc     540

agcctacatg atttctgctg agaaatccac tgataatctt atgaagcttc ccttgtatgt     600

gaagaattgc ttttctcttg cttctttgaa aattctctct ttgtcatggt gaggatctct     660

ttatatttaa tctattggag ttcttttggg cttcataaat ctggatgttt atttcattta     720

tgtctccaaa ttttgagagt tttctgttct tatttttaaa aataagtttc tgcaactttc     780

tctttctctg cttcttctgg aactcttgtc atgcatatta gttttcttaa cagtgtcctg     840

taatttttgt cagctttctg caatctttat cattcctttt attactctga ctgggtaatt     900

tcaaatgacc tgtatctgag tgtgctgatc ctttctcctg cttgatcaag tctgctgctg     960
```

aagatgtttg tgaatttttt caattcagtc attgtgttct tcagttcgag aatttctgtt 1020
tggttctttt tatggttcct atctatcttt ttgttgaact tctaattttg ctcatgtatt 1080 atttcctga ttttgtttac tgtctatcta tattgttttg tagctcactg agctttctta 1140
agataattat ttttaactct ttgtcatgca gtatagatct ccatttcttt agagtcgcct 1200
cctgctgctt tattttcttc ctttggtggt ttcttgtttc cctgattatt tgtgatcagt 1260
gtggccttgc attgaagtag gtacctattt cagtctttac atactagctt cagtagagga 1320
agccgttcac tagtcagatt gaccagagat tatgggtggg ctgtctgttg ggtctatgc 1380 acaggatttc tgttggagtt ctaaggtagg cagggctgga ttctgggttc attcattgtg 1440
gttgtctgta ttctgtgcac aaggactggc ttgaagcatg gatccttgag ggctgacttg 1500
gcactgaaat gagccttaag cctgagtctg caggggccag cctaacatgg ggatcaccta 1560
gcacctgagt tcatggggac agacctgttc ctgagtttat tcaggctgtc ctgggaccag 1620
ggtccactgg ggtgagccca gcatctgggt ccacatggcc aagatctctg gaggctgacc 1680
tggtgctgga tctgcagggg atggcctgaa ttctaggccc atgggtacca acttggagcc 1740
ttgggctgct ggggctaatg tggaggctag agtcttgggg gccaggctag agctggggca 1800
ggtctgaagt ctaggtcttc tgtggccacc ttggagtcta gacccccagg ggctgacctg 1860
gtctggggtg agcatggggc tgaggccaca gaggccagtc tggcctgtgg caggcctgaa 1920
tcctggtgcc ggggtttact ggagtgggct tggtgcttgg ggtctgtggt gaaggtgggt 1980
gctatcttaa ctgtctctct tccacgcaag agggtatctc tctccatgct gtgctgccca 2040
ggcttgaagg tggggtgaca ctggtaatgt gaaattgtcc ttcctatgca cttcaatgtg 2100
tcttttctta cttctgtgct gcaactgggt ggtacaacct ctcacctgat tcctgagctc 2160
tagtgaagtt attttcgtgc atggatactt attcaaattg atgtttctgc aagggatgag 2220
cactagaaac tcctgttctg acaaactcct attccggttc ttgctgacat cactccctga 2280
aatagttaat atacttaaca gctgaacacg gataggatgt tcacggaata tgttgacagg 2340
acaaaaagtt gaaactgttg gcagaaaccc aaagtcaata tcgaagccaa ggaaaacatt 2400
gcctgcggtg ccacattaga acagcttgaa gaccgttcat ttttaagtga caagagactc 2460
acctccaaga agcaattgtg tttgcaggta gcaaatttct attattctga ttgtttccaa 2520
agaaactata atttttaaag tatagttttt tactttatga gaaaattagt catttatatt 2580
ctaatttcct gagtatatag atagtagaga aggaactaat attcctttat gtagaaatat 2640
ttaaatgtaa gatgacttta aatcaaaaag aatacttgat tgatttaaaa tttttaattg 2700
ggctttaata ttttcagagg ttttctttac ttagggattt ttggactgac attattgcca 2760
ttatttatta attttctttt tgctcaaatc aagaggtttc ataactgttt aatctctctc 2820
tctaccaatt ccctttccaa cattactagc cacagagttt gccaatcaac aataaacaca 2880
acagtagtct ggaggtctca atttgtatct tgggaagcat tataaacttt ccaactccct 2940
agacacaaat gtagagaaaa aaccccttgt tttctatacc agaaactgtg tgctttgtct 3000
tgtaattcag acatttacaa gaaaatctgt atcaccttaa attaagattt atgttaaatg 3060
cagtctaaaa ccaacagagt tatgtattgt tttctttttt agaatgattt tattcaagca 3120
agcaacttat ttcatttcct tgtttgctac agtttcctgt ggtaagtgaa ttatctataa 3180
agcatgaaat tcaggctaag acaggagtag ccaagcaagt cgcaccacct ctggagaaag 3240
ctattgaaca tacagcttcg gggatggaga tagtccctga tgattcagga cacgtgtcta 3300

-continued

```
tttaatgttc cagaacaagt acgacttgtg agatatattg ctgtatacat acattgcaga   3360
ccagaggaag gagctcagaa gcgggaatgt cttgggactt gtgttaataa aaacttctgt   3420
tcacagatga cactctgcaa aacaaaactc aaaacaaaaa aattactcct ctatttttat   3480
caacattaaa aaattaaaca ttatctgaaa tttcaaaaga gtgctgggca ttatatagtg   3540
tctgggtcca atccaagtat ctgttaggta catgatacat agttttactc tggacagcca   3600
gggaaccatt tcaaaaatga aagtacctgg tttaaattta acttagcaaa ccaggcattt   3660
ggatagttct aggtgaataa ctttcaacac tagatttcga tctcatttct ctattaatat   3720
cattaatttt tggagaataa aaatgattct ggacatttca ttaatcgcta tagagggagt   3780
tttctctgtg tccccacaag gcatgattct gagtctatgg tgacttaaga gggccacata   3840
acaatgagta tttaactttc ctctcgtatg gctacaataa acgtctacag ggaaggttta   3900
cattcataaa gagactactt ttccaggaaa aaaggctttg attcccccta aatcacaact   3960
cccctgtgtc tgtccctcaa ccctgattgc ttttctaaac cgtaatttac caacccatgt   4020
gcaaacccac tgaaaactga aaaggagcat gagccaggga tactgtgaac cacggccacc   4080
tccaggtggt ttctcatttt ctgttttttt cttctggcaa aataaatcat gattatggct   4140
aggaaaatta aggatgtaaa taagcaaaaa actataaact acatattgca tgtagtcccc   4200
aaattcagaa gcagtcgttg ttaaacatct tttgtttagt ctttcagata tttttctaca   4260
tatgcctatt tgcacatttt acaaaaaaga gttattaact atggatactc tttgacttgc   4320
attttccact tacagctacc ttttggtgca aataaatgac attttttgga gcttgctatt   4380
ctctttttat ggtatgtttg tgtgcacatt cttatgcact tagttatttc tgtagaatac   4440
atttttgaa ataaaaatac tagattcaaa ggtatgaata ttttagaagg ttttatggtg   4500
tggcatcatg aaattatctt tcagaaaagt tactccctag ttgacttctt ctaccagcta   4560
ataagagtcc ttatttaccc cacttaggcc aacactaaca ggcttctgtt gctttgcatc   4620
ccgacatgtt tatctttctg gaaacagtat cctaatttat ttctgcagag ctactgcctc   4680
tcagttttgg tccatgtggt tctggtgacc ctgactcttc tgctgaacca ggaagtgcac   4740
acatcctgct gactgcagtg acccaatcag agccaacatc ttgcaatgaa gcgtttgttt   4800
agacgtctag aaataggact cttacttttt tttttccaat ttaacttgaa acataagaga   4860
atacagaggc ctgagctgct ggtcctattt tgctactatg tggagcttga gagtaatggt   4920
aacaccatga ctggagcaag cggaaggaga ctattgtcca ctgatgctat ccgttgagca   4980
caatgtgggg ttactcctta agccagagtc accatgggct ttttggctcc tgaaccaata   5040
gatttcattt gtattcaagc cactttgtac taggttttcc atcatttgca atcaaaacca   5100
gtatacaaat actggttatt taatttttca tttttactaa tctcatggaa aactggcttc   5160
tagttgtttt aacttgcctg tatttgtgat tcttcccatt ttcgtgtact tactaatcac   5220
ttctatttct tttgtaaatt atcttttcat atttgtccac taattcttta aaattagagt   5280
acttttcttc tccttattgt ttatgtaatt gttaaacaag actgaataac ctgcccaaaa   5340
tccgtggaca tgggagccca tgtgaaagct ttgaaagcca ccatcattat gagataaact   5400
atataacagt actttacata tgctccaaaa tacagtacag acacggctat cattgtcatg   5460
atcatgatca tcattatcag catgatcacc aacttaggag gataagcaag aacacctact   5520
agaagtttct ttccattcag caacaaagtt ggcgtttttc tagtcactcc cttccctgac   5580
tgagtcacat ggcaggtcac agaggctcaa tggcagaatg ggaagctctg ggccagcacc   5640
agccattgtg tgcatccttg cgtgtgaacc taggtgctgg aagaggagtg actgcttgat   5700
```

-continued aattatgagt cagtcaaaac caccaactgt ctgacaaaac agacctcttt gtaacctgta 5760
ttgtcactaa accaatgcct ccatgctttg tgcatacatg aaatctaggc aatacacttg 5820
tattccccaa agcttccatt tgaagagatc tgtgctcttc ccaaatgtaa accttacccg 5880
agaggtggtc atctggccgc acctctgaga gggatagaag tcttgctgtg ttgggtggtc 5940
agactggggc tcagggccag aattcccagg gggtaggatt gtgcagagaa gatggcactc 6000
tccagtgctt aataaaatgc acgtggtcta agttgcccat tccctcaaag gcaataaaaa 6060
aataggtact atttaaattg aagagtaact actgccccag cgaatggaca ggttgtcatc 6120
ggaatagcca tggttaatgc cccagcgaat ggacaggttg tcatcggaat agccatggtt 6180
aatgccccag cgaatggaca ggttatcatc ggagtagcca tggttaatgg tcagttgact 6240
gactgaaatg aatatgctgg ctgaccagga aagctcatta agcagacttg gaagagagtc 6300
tttccaggta aatccacatt tacaaattaa agcagtaatg acacctaatt ctctaataat 6360
aggtggggtg cagtgtattt tagagctggg aataattcca aacagcaaat agttcaaaat 6420
ttattttcca tttagcatat gcatgcattt gcttaaacta tcttaaaaat gagtaaaaaa 6480
tattgtcagt ttgcttgaat catactgaga tgcggaacaa tatttagcac tgcatgctag 6540
aaaaggacac aggattggga gtcagggctg ggtgactgtc gcaggatttt cattaagtgt 6600
gtggatcttg ggcaagtctg tatgccctga gattcagtta tttaactttc tttcaaaaaa 6660
cctaatccag atgcagataa caaaacctgc ttctaacttc ccttacagaa ttgtgagaag 6720
ctggtggaga tgtttgtaac caaagtgttt tgaaaataga gcaaatatta ttctttttaa 6780
ggcatgatat tttcatagca tgtcaggcaa cagggaaaaa ctaagttagg attttatttt 6840
attgtgggta atttatgtgc aaattttggt gcaatttaat gaaaataagc caaagtttta 6900
atgcagaagt gcccagaaaa ttaaataaca atctacattg ttcaaatggt tgccttaata 6960
tattttattt tctcagcata attagaatta tattatacag gtcttggagt agtcagtcag 7020
tgggagaagt taagacaaca gatatctttt tgttaaaatt attatttgaa ttatctcaaa 7080
ttaactttta tggttctatc acaggatgtc tgactcaact atatgaaaac gccttcttca 7140
gaggtgggga tgtagcttcc atgtacaccc cgaacgccca gcactgccag atgatgtgca 7200
cattccaccc aaggtgtttg ctattcagtt ttcttccagc aagttccatc aatgacatgg 7260
agaaaaggta aaagttgata tttcattatt ggagaagcca tttttctaaa ctgaatcggt 7320
tttgtgcaaa gaggtgtagt ataactgaga gttctgtctc agacggggct caaggaccag 7380
cttcagcaaa atcccttcaa gtggttctta ccaatgcaga ttcctcggca acaacccaga 7440
tttgctgaac caaagtttct tgggactaga aattgcattt taaacaatca ctgtgtttat 7500
ttaaagtagt agaagttagt cattttctat tcaaagcctc aaaatgcttg aacatcgttg 7560
ggctaagaga ttgtctccag aaagcatcta acaggcgaac atttcatctg aataaagaaa 7620
cagacttaac tgtgtgaccc gtgatcacat tagtggctag cacagtccga aggaaataac 7680
gtaagacaag cattttgcgg agaatataat tgagaaacat ctagaacttg tgattttggg 7740
acagggcaga tctgaatgac gcctaaagtg agccagtttg ggcacctatg gcatgatgct 7800
atgtatggta tgtgtgtgtt catgtgtgct tgtgcttgtg tgaatatgta ttattaactg 7860
gagatttgta aaagtattgg aaaaatacta cttatgattt tttttttttt tgagatggag 7920
tcttgctttg taacccaggc tggagtgcag tggcacgatc ttggctcact gcaacttccg 7980
cctcccaggt tcaagcgatt ctcctgcctt agcctcccaa gtagctggga ttacaggcac 8040

-continued

```
gcaccactac atctggctaa tttttgtatt tttagtagag acggggtttc accatattgg   8100
ccaggctggc cttgaactcc tgaccttgtg atccacctgc ctctgcctcc taaagtgctg   8160
ggattacagg cgtgagccac cgcacccggc tgtaattaca atttttatta catcagagag   8220
atgcttatta atcacaagct acagtttcat cttaatgatt ttcattttga ataagaataa   8280
gcttttcttt gttcttccca tttccatatt cataactctt ttctcatctt ctccacgtga   8340
gtttgtgaac tagaaattgg atagtcattc tctgatccta catgttaaac ttgtagagaa   8400
aacccagatt gtatgtgagg atcatcatct taaaagtgga ggtaggttct agaattctta   8460
taaataatga aattaacatg gaggctgaca tttgagacag agggaagtct ttcattaagt   8520
gcagactaca aggagttaat aagcaagatg aacacacaat atacagatcc agctcttatc   8580
actaagttaa ttttttaagt aaatgaaagt atttgcaaaa ataattacca attaaggaca   8640
tagttgcctg aaggtttaag aatacaggaa aagtcattaa ctcttcaatg tggttgactt   8700
cctgtactta aaaaatgtga gtgtaaagaa aacgcaatgc tgaagttaaa tattatgggg   8760
atgttataaa attacctcta agagtgttct ttccagcaag ttttggggaa gctatattat   8820
ttcccttatt cctggtttta tgttagtgta tagaaaatgc tagacatttc ctcaatgtat   8880
gtttgttgtt ctacttccta aataaagcta cttttaaaac aggtttggct gcttcttgaa   8940
agatagtgtt acaggaacct tgccaaaagt acgtcgagca ggtgcaattt ctggacattc   9000
cttaaagcag tgtggtcatc aaataagtgg taagctgcga atttcttagc tacatttgag   9060
ttaatattga atctacctta gaacagcttt tgctaaaagt ctgtactgct acagcctttg   9120
ggaaggaatc actcataaag atagaagatg gggcagtatt ctggacacaa aagagggacc   9180
catattcatc tggacacttc tgttgtcttt atcaatcgac acgtatttaa tgagcctcta   9240
ttatttatga ggttagcact caagtgtaag atttgcagaa aatgaatcca aataatcgtg   9300
tctccttgtt tccagataag aatttttaag aaaacacgag ggaacatctc tctcaggttc   9360
acgtgagggt aatttttata tcagtgattc tcaactggca gtgatttttg tctcttccat   9420
taggggacat ttgacaatgt ctggagacac ttttggttgc tatgactagg gagggcgtta   9480
ttagcattta ctaagtagag gccagaatgc ctctctcatt tactaagaag aggccagaac   9540
gttcgaatgc tgctgcccaa ccttctacaa ggcacagagc agtcctccac agcaaataat   9600
cttctggccc aaaatgtcaa cagtgctgac atcaagaaac tctgatatac cattaggccc   9660
aaactgaaga actgggttct gcaaatcttg ctaagaataa tacttcttaa aggaaacttg   9720
aggactagga tgctagagaa ctttgatttt acatctgaag ctactgatgt cttgggaaat   9780
aatttccaac actatcctaa taaatttaag acaaatgaac tatttctcaa acatgactgg   9840
gactgatcag aaagtgagaa gtgctgaaaa gattcaactg atgggttgtc ggaatcttaa   9900
aatagctgtg ctgtgattct atgtgtgact atacatcata actattttat ttgtattatg   9960
cacaattaat tttgtaggtt caaatttcag atgtttttaa atttgtcatc ctttcctccc  10020
tcattgatat caccccttcg atacatacac actttgagcc tgctgtttgc atgttaacca  10080
gttatcaaag gatggcaaag cgttcgttat gaatatgggc ctgacttagc cagtgtaata  10140
agtgtagtct acctgaggtg gggtacattt cctgttttat aagaccaatg tgtatgttca  10200
tctaatttgg tataaagtat tcaaggaagt gctgtttcca attgttgtat cttatagcaa  10260
aatttaaaga aaaagtaaca ttgtgccttc cccaatattc ctgttattgt taatgtattc  10320
taaaactcag tgttactcac ttagcttgct tttaatgttt ttttctaact tcatcatctt  10380
aaagtgaaaa attgttccca agtacataaa atctctactt tcaggaacaa ttctagtcga  10440
```

-continued

```
aagcatttag agctttcaca tgaacactta caaagttgtt atttgtgaga gtcccatccc  10500
aactcttagc ctactctttt ctcacacgca gaaaaattgg aaagagattt catttcgacc  10560
gtctgcaaat tcctgtgttt aagaaccact gtgaataatc cacctcccta cccaattccc  10620
aattcgacat gcagttttcc tgacagtttg tatgttttct gtctttccca cccttaaatt  10680
tagttttatg acttcaacca cacttcttag gagtggaaag ttacctgtaa tagattatgg  10740
tttattccac ataatcttgg ggaataaaac tttaaaaaag tttatggttt agacttctgg  10800
tttacattac ttccttaacc aaaagtctaa ctaagaaatt tgaatattta aaaaaaaaaa  10860
gagcctaatt ttgcttcctt gtctgtgaaa agaattatct atatcttttg catgtaagac  10920
aaatctcagt gaaaagggtg cttaaataga agttaacact attttaaagc aagaatggaa  10980
gtggcttcat catgcataaa caacaactct ccacattttg taacgattga tccagatgca  11040
atttgtagtc agacaggaga agttgaaagc agagaaagaa cactgggaga tagagaagct  11100
ccttcattca atgcaaaagg tcaaaggcac atcagtttct ttaataatgc aaacctcagc  11160
acacatgatc agtgtcctca ttattattgc cttgtttatt tcccactgct cactgttaat  11220
ttcaacgtga aatttacctg tattgctgca tgcatcttgc agtttaagaa gcgaagtaac  11280
ccaatttcca agctagtgct ttcaggaaaa tactggattg tatttacttc gagcagagtt  11340
tgataattta tggacatcat aaaaatttta aatcccttaa ttaatatagc aattgccaaa  11400
actgggctgt tatccttcta aactaccggc ccaaatggta gtgggatcct tctaaactac  11460
cagcccaaat ggtagtgggt atctaatcta cctctagaaa gaaaatggac tgtgtttgct  11520
ctatttcctt tttcttgtac agcttgccac cgagacattt ataaaggaat tgatatgaga  11580
ggagtcaatt ttaatgtatc taaggttagc agtgttgaag aatgccaaaa aaggtgcacc  11640
aataacattc gctgccaatt tttttcatat gccacacaaa catttcacaa tgcagagtac  11700
cggtgagtac aattcatggt gtttgttctt tatattagtg cccccaggat ttcactgtat  11760
tcttcacaac ctcttttgtt cccaaactaa aaaccaaaca gggcttttac tcctaaccac  11820
tttccttatt tacttactct attttatatt tttatcttct tttttttttt ttttttgaga  11880
tggagtctcg cgtgttgccc aggctggagt gcagtggctc aatctcggct cactgcaacc  11940
tgtgcttcct ggcttcaagc aatcctcctt cctcagcctc ccatgtagct aggactacag  12000
gcgcccacca ccacacctag ctaattttta tgtttttact agagacgggg ttttaccatg  12060
ttgctcaggc tggtctggaa ctcctgatct cgtgatccac ccacctgggc ctcccaaagc  12120
gctgggatta caggcatgag ccactgctcc cggcccttca ttttaaagtt aaataattca  12180
tttaatttca tttgtttctc tactcttttc ctctggcagg taattgtacc ccatcttcaa  12240
agcctggcat cctcttccac cacttctcca aaggctgatt ctttcaggtc tttcctcaga  12300
taccgtcccc tccaaagggc catttctgag cattctcttt taagccacat tcagctctgt  12360
ttatttcatt cgtagagcta atcacaattt gattttaact tgtgaatttc tttccttatt  12420
tttaaatctc gtttttgttt gcatagatgt atggggtaca agtgtaattt tgttaccttg  12480
gtgtattgta cagtggtaaa gtctgggctt ttggtatatc catcactgga gtcacgtaca  12540
ttgtacccac taagcaattt gtcatcacct gccccttccc cacctctcta tcgccttccc  12600
agtctctact gtcgatcact ccatgctctt ctcaattgtg gtgtcatttt tcctgaagcg  12660
aaatttcggt gtcattgttt ctgaagtcat tttctgacgt ctgtgtcatt ttttgctttc  12720
ctgaagtgaa ttttggtgtc atttttcctg aagttccatt tgccccacgc ataggcctta  12780
```

-continued

```
cttgtagaat gagggtttag tgtcatggtg tctcctgcct cattctcacc ccaactttcc  12840
cttgacccct ttgcgaggag aaggatgtcc atttgattaa taatgcaaac ccctaaccca  12900
ctcattatca gcatcattgt tttttccact gtccgtttga atactaaatg ttacctggac  12960
tgctacctcc gcctcaaagt gcaggaagca aagtcacctc ttttcttccc attcaggaac  13020
acttgcctct taaagcacag tcccggagga acgcctacca ctataaaggt gctgaataac  13080
gtggaatctg gattctcact gaagccctgt gccctttcag aaattggtaa ttgtaggacc  13140
acttcacctt gtgattgtag taggcggaat aggacccccc agagatgtcc ctgtgcggag  13200
ccccggtacc tgtgcgtgtg ttcccatagc tggcaaaagc gtttctatca atgggattca  13260
gttaaggact ttgagatggg gagtttactc tggatttcct cgatgggccc aatgtactca  13320
caggattggg tgctcacaag gctaataaga aaaagggaga ggcagaaggg tcagaggcag  13380
agagaggttt gaaggtgtta cactgctggc tttgaagatg aaggtccatg agccaaggaa  13440
tgcaagtggc ctctagaagt tgaaaagggc gaggaaacag tttccctgtg gagcatcctg  13500
gaggaacaag ccctgctgat gtcttgattt tagcccagta agacccaatc tctagaatgg  13560
taagataata aatttttgtt gtttttaacc actgagtttg tggttatgcc cctatagcag  13620
cagttatagg aaactagtac agtgatattg ttataggtac aatgatattg tagcaaaact  13680
gtaaggacct tccttggttg tgtccctatc tagggaaatg actctaccgg ggggagggaa  13740
ataacattct gtcgtgtcac acataaaggt aatttcaatg gaattgtcca gaaaattgcc  13800
atgacattcc acctcattta gcgtatcagg atgttaacga caagatgtta ctgaaaccaa  13860
atcccttact gccagttctc cgcagtagtg ggtgctggct ctgtgcctgg ccctgtattg  13920
ggtgctgggc taggatttcc ctgtggaaga ttgggaaggt tggttacaag gtgtctattt  13980
tcctgtctcc tctttgtgac agcacacctt ctccacggtg cgtgccaggt tcacgtgtac  14040
tgatgatgtg attttaacgt tcatattatt tttttccggg agagtttttg aaggctgcca  14100
ggaggcagga ctcgatgcaa gcatgctcca ttctgtaccc agcactgttg ctggaaggat  14160
ttgctgcact tacccaggga acaggcaagc tcatgccgtg gttctgggct gtcacagctg  14220
ctgtccacac ctgggagagc accctggatg gctcatctct gtacttgctt tcttgttaaa  14280
ttgcagtgag ttcacatgtg atttaatctg atcaaatggc ctttacagac tggtaaaaat  14340
ctggctgttt caggcagtgt tttgagctgc taaaggcatg gcttttcact gagtacgtgt  14400
tccccgttcc tcagggaaca cccagtagct acgtgcctcc tcaacctgga gtagggctgt  14460
ctcctggcct cactgcccag atgagattca taagttaggg atcatctgta gtcatcacta  14520
caggtttgtc cttagtttca ccatggattt ttctaatttt acaaacaaaa cccctaaggc  14580
tcctagaagg agggcagaag tgaaggtgct tgggggtcat atagctgatg agctgaacga  14640
gaacttgacc cttgggtcac acagatttca cattgctcac tccccatttt gatttttttaa  14700
tggatttaat ggtgttttaa agtctcctgc ctctcaactc atataaattc atcatattta  14760
cagatttcct tctcttgcgg tccatcttcc tgcatagatc ttgacagatg tcagggtaat  14820
cacatcttcc cagttaattt aacaaaaccg tttgcaattc tgatatggga aatctaccat  14880
atgacttatt aatttatcaa ttgaggtgat aaacatattt ttcaagccaa aagtaggaga  14940
acataaactg gaaaaaaaag ttttttttatt ttttattttt ttatttttat cacctctggg  15000
gaagaaaatc tgataaatga acctggttga tgaaattgca attagtggga gcaacatcat  15060
ggtttctgtt ctgagaataa ccagatggta tacttgaaat agagaatgtc ctagaaatca  15120
actggttgct tggccaaaat atctataaat agtgcccgac atattagata ggaaaagcaa  15180
```

-continued

```
agtaaaagca attttaatag gttaggacat tgggctgaag tattgcatat atttaatgtc  15240
acgtgcatct gtgtgaagag accaccaaac aggctttgtg tgagcaataa agctttttaa  15300
tcacctgggt gcaggaaggc tgagtccaaa aagagagtca gggaagcgag ataggggtgg  15360
ggccatttta caggatttgg gtaggtaacg gaaaattaca gtcaaagggg ttgttctctg  15420
gtgggcaggg gtgggggtca caaggtgctc agtgggagag cttctgagcc aggagaagga  15480
atttcacaag gtaatgtcat cagttaaggc aggaaccgac tattttcact tcttttgtca  15540
ttcttcagtt acttcaggcc atctggatgt atgtgttcag gcttaggccc agaggcctga  15600
cattcctgtc ttctcatatt aataagaaaa ataaaatgaa ataggagtaa agtgttgggg  15660
tggcaaaaat tttggaggtg gtatggagag ataacgggca atgtttctca gggctgcttc  15720
gagcaggatt aggggtggcg tgggaaccta gagtgggaga gattaagctg aagaaagatt  15780
ttgtggtaaa ggttgatatt gtggggttgt tagtgggagc atttgtcgta tagaatgatt  15840
ggtgatagcc tggatatggt tttgtatgaa ttgagaaact aaacagaaga cataaggtct  15900
gaataagaga aggagaaaaa caggtattaa aggactaaga attgggagga cccaggacat  15960
ctaattagag agtgcctgag ggggttcaac ataattagtt gcttggttgc tgagtttttg  16020
ggctctatcc ttgacagagt cctccttctt aagttggagg ctgagcttgg tgaggtgtgt  16080
ttttaaaaga ccattagtcc tttctacctt tcctgaagat tgaggagagt aaggagtatg  16140
aaggttttac tgactactaa gagcctgaga aactgcttgg gtgatttgac taataaaggc  16200
cagtccatta tcagattgta tagaggtggg aagtccaaac caaggaatta tgtcttacag  16260
aagggaagaa atgaccacgg tggccttctc agaccctgtg ggaaaggcct ctacccatcc  16320
agtgaaagtg tctgcccaga ccaagaggta ttttagtttc ctgactcggg gcatgtgagt  16380
aaagtcaatt taccagtcct ctgcagggac aaatccccaa gcttgatgtg tagggaaggg  16440
agggggcctg aacaatcctt gaggagtagt agaatagcag atggaatact gagaagtgat  16500
ttccttgggg atagatttcc acaatggaaa ggaaaagagg ggttttaaga ggcaggctag  16560
tggcttgtaa cttacatgga agaggttacg aaatgatgac agaatagaat gggcctgtga  16620
ggctggaagg agatattttc cttggtccaa gaactatttg ccttgtgtgg gaagagattg  16680
ataggtggaa gtttcaatgt gggagtagat gggagtgacc gattagaggg aggaaaaact  16740
ggccgtgagg gacagaagtt ggaatgctag ctgcttttat aactacctta tcagcatggg  16800
tgttgccttg agcaatggga tctgatgcct tttgatggcc cttgcagtga atgactccag  16860
cttcctttgg acgtaaagtg gccttgagaa gagtttttat taaagaggca ttaatgatgg  16920
aggacccttg cagagtgagg aaacctcttt cagcccatat aacagcatag tggtgcagga  16980
tatggaaggc atatttagag tcagtgtaaa tattgatgca tagtaccttt gcaagagtga  17040
ggacctgagt taaggcaatg agtttggctt gctgagaggt aagttaaggc aatgagtttg  17100
gcttgctgag aggtagtgga ggggtgcaga gtggtagcct caatgataga tgtagaagat  17160
attatagcat accctgcctt tgctggtggg tggagattag gcctggtgga actgccatca  17220
ataaaccaag tgtgattagg gtaaggaata ggaaagacag aagtatgggg aaatggagtg  17280
gatgtcaggt ggatcagaga gatacagtca tggggatggg ggccagccta aaacagtaag  17340
gtcaagttgt ttctacagaa agcnnnnnnn nnnnnnnnnn nnnnnnnnnn nnnnnnnnnn  17400
nnnnnnnnnn nnnnnnnnnn nnnnnnnnnn nnnnnnnnnn nnnnnnnnnn nnnnnnnnnn  17460
nnnnnnnnnn nnnnnnnnnn nnnnnnnnnn nnnnnnnnnn nnnnnnnnnn nnnnnnnnnn  17520
```

-continued

```
nnnnnnnnnn nnnnnnnnnn nnnnnnnnnn nnnnnnnnnn nnnnnnnnnn nnnnnnnnnn  17580
nnnnnnnnnn nnnnnnnnnn nnnnnnnnnn nnnnnnnnnn nnnnnnnnnn nnnnnnnnnn  17640
nnnnnnnnnn nnnnnnnnnn nnnnnnnnnn nnnnnnnnnn nnnnnnnnnn nnnnnnnnnn  17700
nnnnnnnnnn nnnnnnnnnn nnnnnnnnnn nnnnnnnnnn nnnnnnnnnn nnnnnnnnnn  17760
nnnnnnnnnn nnnnnnnnnn nnnnnnnnnn nnnnnnnnnn nnnnnnnnnn nnnnnnnnnn  17820
nnnnnnnnnn nnnnnnnnnn nnnnnnnnnn nnnnnnnnnn nnnnnnnnnn nnnnnnnnnn  17880
nnnnnnnnnn nnnnnnnnnn nnnnnnnnnn nnnnnnnnnn nnnnnnnnnn nnnnnnnnnn  17940
nnnnnnnnnn nnnnnnnnnn nnnnnnnnnn nnnnnnnnnn nnnnnnnnnn nnnnnnnnnn  18000
nnnnnnnnnn nnnnnnnnnn nnnnnnnnnn nnnnnnnnnn nnnnnnnnnn nnnnnnnnnn  18060
nnnnnnnnnn nnnnnnnnnn nnnnnnnnnn nnnnnnnnnn nnnnnnnnnn nnnnnnnnnn  18120
nnnnnnnnnn nnnnnnnnnn nnnnnnnnnn nnnnnnnnnn nnnnnnnnnn nnnnnnnnnn  18180
nnnnnnnnnn nnnnnnnnnn nnnnnnnnnn nnnnnnnnnn nnnnnnnnnn nnnnnnnnnn  18240
nnnnnnnnnn nnnnnnnnnn nnnnnnnnnn nnnnnnnnnn nnnnnnnnnn nnnnnnnnnn  18300
nnnnnnnnnn nnctggcgag gagcagcctg gggaggaggg gagaggtcag atgggtccat  18360
agaaaaggaa gattggaaag actcagcaac gcttggggtt gggattgagg ggacaggcgg  18420
gagggaaaga aggaagattt gggatgagtt gcattgggaa caaagactag ggagggactg  18480
atgtgtaaaa gactgcctgg acatcaggca gctcagacca tttgcccatt ttacaacaag  18540
aattatctag atcttgtagg atggaaaaat caaaagtgcc gttttctggc tatttggaac  18600
cattgtcaag tttgtattgg ggttaagcgg cattgcagaa gaaaataagg cgttttggtt  18660
ttaggtcagg tgtgagttga agaggtttta agttcttgag aacataggct gagggagaag  18720
aaggaggagt ggagggtgga aagttgccta tagtgaatga ggcaagccca gagaaaagag  18780
agggtagaga cacggagaga aggggtcagg gtgcttgccc cccaggaaag tggtgcttgc  18840
cactaagggt gaaggatcaa ggcaggcatc cctaaggtga tcagacacct ctgaaacatg  18900
ggcgcataat caagcaggtg tccctgtagt gattaaatgc caagggaaga ctgtcttccc  18960
gagtccatga ctggtgccag agttttgggt tcacagataa aacgcgtctc ctctgtctct  19020
accagaaaat gaaatgaatt gaaattaaga gaagggagag attgaaggat ggcgccaaga  19080
ttaaaaggag aaagaggttg agggatagtg agagagattg gataagagag taaaaagagg  19140
ccgtttaccc aatttaaaat tggtgagatg ttccttgggc tggttggtct gaggaccaga  19200
ggtcataggt ggatctttct cacagagcaa agagcaggag gacaggggat tgatctccca  19260
agggaggtcc cccaatccgt gtcacggcac caaatgtcat gtgcacccgt gtgaagagac  19320
cactaaacag gctttgtgtg agcaataaag ctttttaatc acctgggtgc aggtgggctg  19380
agtcagaaaa gagagtcagt gaagggagat aggggtgggc cgttttatag gatttgggtg  19440
ggtaatagaa aattatagtc aaaggggttg ttctctgatg ggcagggttg gagctcacaa  19500
ggtgctcagt gggtgagctt ctgagccagg agaaggaatt tcataaggtg atgtcatcag  19560
ttaaggcagg aaccggccat tttcacttct tttgtcattc ttcacttact tcaggccatc  19620
tggatgtatg cgtgcaggct tgggcccaga gacctgacat ttaacatgaa taaatgtgaa  19680
gttcttagaa tcatacatac acattggaaa agatggggtt taatagcact ttataaggag  19740
acttgaagaa tgtttgagaa tccaccatga agctgctgaa aatatcaaga aaatttaatt  19800
cttatgtata taaataatgt gtctgtttta catgaattcc ctctatcaag tttggtattt  19860
taatatagca tatattattt tttcatagta gatttaaaat ttttgatgta taatttagat  19920
```

-continued

```
aacataaaat taaccctttg aaagtgtaca actcagtggt ttttagtata tccacctgat  19980
ttcacaagaa tcaccactat ctagttccag aacattttta ttaccactga agaaagactg  20040
tatccattgg cagtctttct ccattgccta ctcctccaat cccctgacaa ccactaatct  20100
actttctatg tctgtggact tgactcttcg ggacatttta cataaatgca atcatgcaat  20160
gcagcacatt ttgcatctag ctttttttcat ctggagtgtt ttcaaggctc attcatattc  20220
tagcatatat cggtactttg ttcctattta ggactaaata gtattctatt atatgaataa  20280
accatatttt gtttatatac ttagtttgat gaacatttga gttgtttctg gattttttttt  20340
ttttttttt ttttgcctct tatgaataat gctgcaatgg acagcagttt ttgtgtaggc  20400
atacatttta aattatctta tgtatatact taggattaaa attgttggat catacagtaa  20460
ctccatgttt aactttttga ggaagtgtca aactgttttt gagagcagct acacaatttt  20520
acattcttac cagcaacaac tgagtgcttc aatctctcta caaccttaac aacacttgtt  20580
attgtctttt ttattattgc ctttctaggc agtgtgaagt ggtgtctcac tgtggttttg  20640
atatgtattt ccctaatgac taataatgtt gtgtatcttt tcatatgctt attatcaatt  20700
tgaataaatt ctttggggaa atctctgttt aaatccttta gccattaaaa ataattgggt  20760
tattttgttt tcattgttga gttgtatgaa ctctttatat actctggata ctacactctt  20820
gtaacatata ttattggcaa attttctgtg catctgcagg tcatcttttc actttagtga  20880
tggtgttctc tgaagcgcaa aagtttttaa acttgatgaa atacagtctg gctttattct  20940
tgcatgtgct ttacctaaaa tgccaaaacc taattcatgg ttatgaagat ttttgtgtat  21000
gatttgttct tagaggttta tagttttagc tcttacattt aggcatttga tgcattttaa  21060
attaaatttt gtatatggtg taaagtagga atccaactta attcttgtat gtggatattc  21120
agttattcca ttgtcttgaa actcttttca aaatcaattt tctataaatg taagagttta  21180
tttttagacc atcagttcta tcccattgac ctgtatgtct gtcctaatgc cagttacaca  21240
cagtcttgat taccataact tcgtagtaag ttttgaactc agacagtctg agtgctttta  21300
ttttgttctt tttcaagatt aatttggtta ttccggatct tttgcatttc catatgaatt  21360
gtaggttggt tgtcaatttc tgcaaccaga aggcagcagg attttgacag agagggcatt  21420
gaatctgtag accaatgagt atcaatagaa ttatgtgtta tcaaatttag taaactacgt  21480
aaacgatagg aacacagcta aaataaaact aagatataag atcgtattaa tgtaatgtta  21540
ataaaagtag attgtctccc attctaattt taatgggcac aaggcatttt tgttaatcac  21600
ttcttattaa ataatttttt ataatattca ggaaaataca acaacaaaaa acccttacat  21660
tccaaaggcc tcagagtcag agtaatagaa ggaaaacgta aacacatgct gagtaatgca  21720
aacatttggc aacggtggtg actggagctg ggagcacagc ttttatttct ctgacatagg  21780
agtttgcccc ttagagttgg accagttttg ccttcctcta aatgacaaac agtttggagg  21840
tattttaaag gacgttttgt cacttaggat gtttagtacc atgaataata taaatagtca  21900
taattcctta attacgatga caaaatacaa gcgaatttag catcgtgtgg tttcctaagg  21960
aacatctctc tctgagttca caggttgtca catgaacatc ttccagcatc ttgccttctc  22020
ggatgtggat gttgccagag ttctcgcccc agatgctttt gtgtgtcgaa ccatctgcac  22080
ctatcatccc agctgcctct tctttacgtt ctatacgaat gcatggaaga tcgagtcaca  22140
aaggcgagta tgcatggcta gcacttgctg ctgtactttc atcaatttta ttttagagtc  22200
tgagttttta aaagtttcct tcatttccct caaaacactt ggacctgcag tttaagtagg  22260
```

-continued

```
tacttttctg ccaggtgcag attagttaag agattagcag acttctctgc ctgtcttctc  22320
ttactttaaa acacatgtta ccagctgggt gcggtggctc ccacctgtaa tcccagcaca  22380
ttgggaggcc gaggcgggtg gatcacgagg tcaggagatg gagaccatcc tggctaacac  22440
ggtgaaaccc cgtctctact aaaaatacac aaaattagcc gggcgaggtg gcggcgcctg  22500
tagtcccagc tcctcgggag gctgaggcag gagaatggcg ggaacccggg gggcggagct  22560
tgcagggagc caagatggcg ccgctcactc cagcctgggt gactgagcga gactccgtct  22620
caaacaaaaa aacaaaaaca aacaaacaaa aaaaaacacg ttaccattga atccaggaag  22680
caatagccat gagaacaaag aaggatctga cgcctttgaa tgaagattca aaacacgatc  22740
ttcacgtttt gtattagctt ggagtaaaag ccactccctg gcagaatatc ccttaagctt  22800
gttgcctctt ccctttgttt cagaaactag agctctgttt attctgatca aggctctgtc  22860
ccactctctt tatctcagat aacccaccct cttctacaca cagcatggag ctaagagaag  22920
ggtgcctagt tatggaatat catcagcagc ataaactccc agaatttctt ctttgatttt  22980
tttgtttgtt tgtttttcca gttagaaggt ggaacttcgt cactgtcctc tcttcaggtt  23040
gtctgtgcct attagttttc tccagaggga gatgtggttt gatttacatt taatctctgc  23100
aatttattag agtcctgtag tcggatttac ttggaagaga gtttcccaaa agaataaaat  23160
ttgccaactt cctttttggg tgtgagctgc ttttgtattt gcctaatgcc tttaatgcaa  23220
acttcttnnn nnnnnnnnnn nnnnnnnnnn nnnnnnnnnn nnnnnnnnnn nnnnnnnnnn  23280
nnnnnnnnnn nnnnnnnnnn nnnnnnnnnn nnnnnnnnnn nnnnnnnnnn nnnnnnnnnn  23340
nnnnnnnnnn nnnnnnnnnn nnnnnnnnnn nnnnnnnnnn nnnnnnnnnn nnnnnnnnnn  23400
nnnnnnnnnn nnnnnnnnnn nnnnnnnnnn nnnnnnnnnn nnnnnnnnnn nnnnnnnnnn  23460
nnnnnnnnnn nnnnnnnnnn nnnnnnnnnn nnnnnnnnnn nnnnnnnnnn nnnnnnnnnn  23520
nnnnnnnnnn nnnnnnnnnn nnnnnnnnnn nnnnnnnnnn nnnnnnnnnn nnnnnnnnnn  23580
nnnnnnnnnn nnnnnnnnnn nnnnnnnnna gaactttacc tggtaatgtg attcaataat  23640
aatattacat aaaacgtaac atatttcatg acttaacagc aacagtgttg aaacaatcca  23700
caaggtaaca gaaacttttg taaatgtcgt tcattgcttt tctcatttgg tatcttttca  23760
tgtttataat tgacacagaa ccctgccatt ctaaaattta cccgggagtt gactttggag  23820
gagaagaatt gaatgtgact ttcgttaaag gagtgaatgt ttgccaagag acttgtacaa  23880
agatgattcg ctgtcagttt ttcacttact ctttactccc agaagactgt aaggaggaga  23940
agtaagggac attttatttt tcatgatcat ttcatatcct ttttccccta gtgaaggctt  24000
actctttcta ctgttcattt catctaggtg taagtgtttc ttaagattat cttcggatgg  24060
ttctccaact aggattacat atgggacaca agggagctct ggttactctt tgagattgtg  24120
taacactggg gacagctctg gtgagtaacc tcacttttc atggaactgt aagggatgtc  24180
tgtcatgttg atagtgtgct tagtcttaag gaattatatg tcttgttctc cttggttaga  24240
agggactttg attcacttct aatttcaacc attagcatca acactcttgt ttcagtctgc  24300
acaacaaaaa caagctcacg cattgttgga ggaacaaact cttcttgggg agagtggccc  24360
tggcaagtga gcctgcaggt gaagctgatg gctcagaggc acctgtgtgg agggtcactc  24420
ataggacacc agtgggtcct cactgctgcc cactgctttg atgggtaagt gttggatgca  24480
tctcatccag agtcttacct tgacttttca ttttgaaggg tctgtgatca gctgcttcac  24540
cgtcatgtga ctttatgaat agagacgtgt taaagcaggg atggtattca caacatttaa  24600
ctagcagagt ccaagcactg accagtctga ccatcataac agagtgtggt ctctgtacag  24660
```

-continued

```
gactgatggc cctgggtggg tattctccca cagaaagaga aacaaacaca atacaccact  24720
cctccaaccc accacccgcc accaatccca ccacccatcc caccacacaa cccaccaccc  24780
atcctgacac caatcccaac accaattcca ccaccaatcc caccaccacc caccaccaat  24840
ccctccacca atcccaccac cacccaccac caatcccatc accaatccca ccaccaatcc  24900
caccaccacc caccaccaat cccaccacca atcccagcac ccgtcccacc accaatccct  24960
ccaccaatcc caccaccaat cccaccacca cccaccacca cccaccacca agcccgccac  25020
caatcccagc acccatccca ccaccaatcc caccatcacc caccaccacc catcaccaat  25080
cccaccacca ataacaccac cagtcccaac gctacccacc accaatccca ccaccaatcc  25140
cagcacccat cccaccacca atcccaccac caatcccacc acccatccca ccaccaatcc  25200
caccaccaat cccaccacca ccaatcctac caccacccac caccaatccc accaccaatc  25260
ccaccaccaa tcccaccacc acccaccacc aatcccacca ccagtcccac caccacccac  25320
caccaatccc accaccaatc ccaccaccac ccactaccaa tcccaccagc agtcctacca  25380
ccaatccctc caccaatccc accaccaccc accaccaatc ccaccaccac ccaccactaa  25440
tcccaccacc aatcccacca gcaatcccac cagcaataaa tcaaagactt atttctcagg  25500
cccatagaaa tgttacttct tgctttttga ttaataaata tactaataat aatttttaaa  25560
agtgagagtt ttgtactccg tatatttcaa catatgtaat ttgatctatt tcagttttat  25620
tggtcaaata gtagacatgt taggtaagtc ttaaaacact gaggttttgg agttagacaa  25680
aacatggctt gagtgataac tttgctgctt attagaggtg tggccctagg agatttgtaa  25740
atctctctga gctttatttt atctaaaaga taaataataa tagtacctaa tttgtaaggt  25800
tattgggagg attaagtgac acatttaaaa tgcttagtac tatatgtcga acatgaacac  25860
tgctcaacaa atgtaaacta tgatttctat attcaataag aagtgtagaa atggacaaag  25920
catatgaaaa agcaaaagaa atactagaag acacttgatt tttctaaaaa ataaacacaa  25980
agtatttttg ttttagtgaa attcatgctt agatgctgtg tactaggatt gaacatacag  26040
ccgccaaaat atagcagttg gtggtacatg tgggtggagc aagacccctc caccttgtca  26100
ccgtgaaggg gctccgccat acatgccctt gcatgtggtt taaaggtggt tggcctggaa  26160
gaaaaggccc aagatgggaa acagtaggtg tcttttttac taaatgtact ccaatttgag  26220
accaggaatt ttcattcttg aaggctcagt attgtaagtt tataagagat aatagacata  26280
aaagtacgat gatttcatta aaaaaaggct cctttgcacg tgatatctcc gttatttttt  26340
ctagaatatt gtgcacacat gccttgcacc acttggtgat gataaagatt tctagatctt  26400
tgcacagaat aaggctttgc tttagatcat aattttggat gtacttagta tgtattcatc  26460
ttttaaagaa tcaatttaaa ttttcatact ttcatatata tatacacaca cacatacaca  26520
aacacacgca cacactttat tttaatattt tatttattta tttattgaga tggaatctca  26580
ctctgtcacc caggctggag tgcagtggca ggatctcggc tcactgcagc ctccgcctcc  26640
caggttcaag cgagtctcct gcctcatcct cccaaatttt tgtattttca gtagagacgg  26700
ggtttcacca tgttggtcag gctggcctta aactcctggc ctcaagtgat ccacccgcct  26760
cggcctcccg aagtgctggg attacaggtg tgagccactg tgcccggccg tatagagata  26820
ttttaaacaa cactgaagtc ctcctactct gcctaattag aagagcattg aaagatcagt  26880
ctgacttctt gatagttctg aatttaatgg agcaatgagg tgcagctttg gtgaatgagc  26940
ttaatttttc catgataaat tgctagtctc ttcccactac agtgtctctc aaaaatggga  27000
```

-continued

```
cagcaacatt ctttgtgttt tcacttgcag taagtaagca tgatacaatt acataaatgt  27060
acacttctca gtttgttaaa tagaatcttc agagattcac gtctgccgct attggtgatg  27120
aaaaatgacc cgtaggagga attaggtagg agaaaatatg tcctatgtag tatttccttc  27180
ccagttctct ttgaaagaga gtgataggaa aaaggaacaa tattgaagga aggccttccc  27240
agtttcaaat aggttttatt tttctctcct aggcttccct taccggatgt ttggcgcatt  27300
tatagtggca ttttaaatct gtcagacatt acaaaagaaa cacctttctc acaaataaaa  27360
gagatcatta ttcaccaaaa ctatagaatc tcagaaggga atcatgatat cgccttaata  27420
aaactccagg ctcctttgaa ttacactggt atgtagcgta tgtaagaagg cggatagcag  27480
aattgtgctg gatgatattt tcatatcagt ttggacaaga gggcagatct agagagactg  27540
ttgttatttt ctgaccggtg gagttgaggg aaaggtgagg gttgcatggg aagtgaagat  27600
cccacgactt gccatgaaat ctcttctacg taaagagcaa gaaacgtgaa ttagttcttt  27660
cagggaggag cacagccgcg cgcaggtgat ggaaataatg gacggaggag atgtctgtgc  27720
cgtctgagag gcaccgggct tcttttgaca agagtagcag aactgtcatt gctttgggct  27780
tagggatatt agaatgtgtg aggaccagtg ggactagata catatttcca ggtataattt  27840
gggtaggaaa gagactgatg ccgaaagaag ccctggaaag gccagaacat cgtgatcaga  27900
ggtgttgcct ttggaggttc attgctgcca ggagctgaat acccactgta tccaataaca  27960
ttaatggcca ggcatggtgg ctcacccctg taatccccac actttgggat gcccaggtgg  28020
gaggattgct tgaggtcagg agtttgagat cagcctgggc aacacagtga gaccctgtct  28080
ctacataaaa ttacaaaaaa aacaattaac tgggtgtggt ggtgtgcacc tgtagtccaa  28140
gctagtcagg aggctgagac aagaggatca tgtcagccca ggaggtcaag gctgtagtga  28200
gccaagatag tgccactgca cacaattatg tgaccttggg caagttgctt tacctctttg  28260
cacctcttaa tttcctcatc tgtaaaatga ggatgataat ttcttcctgg gtttgttgta  28320
ataatcaata cattaaagca cttcatgtct ggaacagtga agacacctgc tatgactatt  28380
aaggatagca tacacggaat aagacgcagg aacttctaaa tgcttttgac cgtagattta  28440
ggttctgagt tttaagaatg taactcagga aattgtaaca ccaaaaaggt catgtgaaaa  28500
atggtggtga caaattttct tgaatcaata gccttagaag ttgggcagaa agcaaaaaag  28560
ttattcttgg tgctactcta tagaaagaga agacagaaaa agaaaaagat gtatttttaa  28620
agtctatatc cataacttta tttgaccaaa ctctaattta aaaattatgt ttcagaattc  28680
caaaaaccaa tatgcctacc ttccaaaggt gacacaaaca caatttatac caactgttgg  28740
gtaactggat ggggcttctc gaaggaaaaa ggtacagcat gatgctttaa atattgcttc  28800
tagagtaagt cttacatgtt gagatgcatg gagtgggtcg ttttaatcgg cttctctctg  28860
aaattatatc gaacccettt atctttccta cctatttatt ccccaatatt tattcagtta  28920
ttcttaaaaa acgtattttt gctttggctt gaaaaaaaaa ttttagggag aattttaagc  28980
atcttacttc attctaaaga tcgtttgctt gacttcgcat gaaagattgt ccccatctaa  29040
ggctgacgag cccgtgcaag accatctggt cctcagtgtt agcagcattc ccatctccca  29100
ataccatgtt ctcccttgat gctaatggcc gggagcacag gcaggcgtgt cgcctctctc  29160
tgtggccagt tcttcatctt cttcttccag gcacccttcc tgcaatctga ggaagcctag  29220
gaaccacttc tctaacaatg cttttaaatg cttaaataaa atacacagga ttacaaaaga  29280
aaccaagtga agtgcaagac agttctcaaa atactttcaa aaagtactac aataatatat  29340
atgcctcttt attaatcctc tacatagcga gttattctaa taccaaacct actttgaaa  29400
```

tagtggtgag cataaatggc attttcactt atctgccaca acagaaaagg gatatgaaaa 29460
tatctgtaat ctctgttgat ggcaaagtca taggtgccac tgatactgct gtgtttgttg 29520
tctgcattcg taatcgaagg gagtggtagg cttcatctgg aggtttgtga aaacaaagac 29580
tttttttcta cacaaattta taagccatgt gaattctttc tgaggacctt aggtttgcaa 29640
ttcctacttg tgggtatctg gagtgttcca atcgtccttg aactttttaa aaaacagacc 29700
agtctccctt tccaaaatta tgttcctgat agacactatg gagaataata tctgtgtcat 29760
tctttacaga agaaggtagc ttgccaaact ctctccatct ttcccgattc agtccttagt 29820
tcaagtgatt cacattttta gatttttac tggtaatctg agacaagaag aaattaaaag 29880
taatcttcac taagcaacga aagctcccaa cactgtcctc cccatgagag atgctcgctt 29940
gcatttactc agaaacaaaa gaccccaaga cccctctgtc gcgaaagctc ggagggcttt 30000
tcagaaacga tagggctttc aattataatt tggaatatat gaaacaaaaa aatgaaaagt 30060
gagaacttcc aggctttgga tttttgtaga tgataaatat aaaatgggat ttctgggga 30120
ctgttaccga gatgagggga tggaagaaga cacggaagca aggtctctgg tcagcccagg 30180
gtgctgggct tgtcccaaca ccacacaggt aataagagga cagtgcaggg ctccgtgtct 30240
ctctctctct ctctctctct gtgtgtgtgt gtgtgtgtaa cactaccttc ctaattttta 30300
ctatttgtat tcaaagatac ggcccttata aaaaagtaca ctgctctgat tcacttgaaa 30360
acttatttcc atatttacta tttattgtgt ttcctccctc tgaagttata tattggttac 30420
ttcacaggtg aaatccaaga tattctacaa aaggtaaata ttcctttggt aacaaatgaa 30480
gaatgccaga aaagatatca agattataaa ataacccaac ggatggtctg tgctggctat 30540
aaagaagggg gaaaagatgc ttgtaaggta atgcatgaga ttatgaaaaa cacaataggc 30600
tgcttgagaa aattcacttc aaaatatatt ttccaatagc ataatttatt atagttttta 30660
aaaaaaattc agagacaaat gatctgataa atttataagc aacttttaac aaattgaata 30720
tatacaatac atatttatat tattcatgat gtatgtcaca atctatgcat gtgctaattt 30780
aagagggaca aaaatacata caataattgc actaaaatat aaaaacatta gatttctttg 30840
tcattgggat gatgatatca agatttcttt gttagattta tttaagaatt gaagagggga 30900
tacaaaaaat gcaggcacat gagatacttg gagaacttta agaaagtttg tgtgtgtgtg 30960
tgtgtgtatg tgtatgtgtg tgttgctgtg tagtggacta cagaatttta gaggtggtca 31020
cttatttgag tcccattgtc ataactttct accattttat ttttcccctg tgactcaggg 31080
agattcaggg ggtcccttag cttgcaaaca caatggaatg tggcgtttgg tgggcatcac 31140
cagctggggc gaaggctgtg cccgcaggga gcaacctggt gtctacacca aagtcgctga 31200
gtacatggac tggattttag agaaaacaca gagcagtgat ggaaacgctc ggatgcaggc 31260
gccagcatga ggagcagccc agagtcttgg cgagttttac aacctgggtt caagtcaaat 31320
tctgagcctg ggggtcctca tctgcaaagc atggagagtg gcatctactt tgcatcctgt 31380
cataaggaca aaagacagtg cactcagagc tgctgaggac aatgttttgc tgaagccagc 31440
tttcagcatt cagtaactgg gagctgataa tgtgaagtcg caaccgagat ctccatgatt 31500
gtgtgtcgta aaataaaatg gtaaaagatc acaattagca agtgttttct tctggttgtg 31560
aaacagaact gaaagtaagt ggttgaggtt ctagcacagt gcctggactc cctctaattg 31620
cactacttct tctggaactc agtctatctc aaagatgtaa tttcctctcc ttgctgcacc 31680
tggttagcca ctgaaaccca cgattgtctg cttcacttgt ggcaaagagc tagcaggctt 31740

```
gggttctgtt ctgccgagtg gaagggagaa cacctgcgtc acacccactc ttataagaaa  31800

gagatgggtt acctgaaccc atagggtata tttgcctctt ggcctcctaa ctttgctact  31860

ggggcatgga taggagggtc caggctgcgt gtgtggagga actcgagggg ctgcagcatt  31920

gcacagcctt catggtaggc aaggaatctg ctttgcaagg ggcattagcc ctggaggctc  31980

agtggatatg ggctattgca atactaattc aaggagcatt tttaggatgg cacattggct  32040

catgcctgta attccaacaa tttgggagat cacggcaggt ggatctcttg agcctaggag  32100

ttcaagacca gcctgggcaa tgtgacaaaa ccccatctct acaaaaatta gctgggcgtg  32160

gtggtgcata cctgtaatcc cagctccccc agaagctgag gcaggaggat cacttgagtg  32220

tggctgcagt gagcagagat cgcactactg cattccagcc tggacgacag agtgagactc  32280

tgtctcaaaa aaaaaaggaa gcattgttag gtataaatta ctattattta tttatttatt  32340

tttgaaagga gtctcgctct gtcacccagg ctgcagtgca gtggcgccat ctcggctcac  32400

tgcaagctcc gcctcccagg ttcacagcat tctcctgcct cagcctcccg agtagctggg  32460

attataggtg cccgccacca cgcctggcta attttttgta tttttagtag aaacggggtt  32520

tcactgtgtt ggccaggatg gtctcgatct cctgactttg tgatccacct gccttggcct  32580

cccaaagtgc tgggattaca gacttgaacc accatgcccg gccctgttag gtataaacta  32640

tttcataaaa ttcagacttg taaatttatc atagccttta gaatggatga tagaaatcct  32700

tatgccacac aaattcctca tatgccaggg ctcaccataa ctgataccag ctcacttgat  32760

tcagctcagt ttaacattta cacagaattg gccatttaca aaatcttaca taagttaagt  32820

agaaaaatag aaaagtgagg ttttctgaaa gagtttgggt ttttccttca atgctcaaca  32880

acagaggtcc ccaatctttc tggcaccaga gaccagtttt gtgcaagaca ctttttccat  32940

gaaccagcgt ggtggggggg ggatgattct ggaatgattc aagtgcatga catttattgt  33000

g                                                                  33001
```

```
<210> SEQ ID NO 19
<211> LENGTH: 2218
<212> TYPE: DNA
<213> ORGANISM: Papio hamadryas

<400> SEQUENCE: 19

agaacagctc ggagaccgtt catttttaag tgacaagaga ctcacctcca agaagcaatt     60

gtgttttcag aatgatttta ttcaagcaag caacttattt catttccttg tttgctacag    120

tttcctgtgg atgtctaact caactatacg aaaacacctt cttcagaggt ggggatgtag    180

cttccatgta caccccgaat gcccagcact gccagatgat gtgcacattc cacccaaggt    240

gtttgctatt cagttttctt ccagcaagtt ccatcaatga catggagaaa aggtttggct    300

gcttcttgaa agatagtgtt acaggaaccc tgccaaaagt acatcgagca ggtgcaattt    360

ctggacattc cttaaagcag tgtggtcatc aaataagtgc ttgccaccga gacatttata    420

aaggaattga tatgagagga gtcaatttta atgtatctaa ggttagcagc gttgaagaat    480

gccaaaaaag gtgcaccaat aacattcgct gccaattttt ttcatatgcc acacaaacat    540

ttcacaatgc agagtaccgg aacacttgcc tcttaaagca cagtcccgga ggaacaccta    600

ccactataaa ggtgctgaat aacgtggaat ctggattctc actgaagccc tgtgcccttt    660

cagaaattgg ttgtcacatg aacatcttcc agcatcttgc cttctcggat gtggatgttg    720

ccagagttct cgccccagat gcttttgtgt gtcgaaccat ctgcacctat catcccagct    780

gcctcttctt tacgttctat acgaatgcat ggaagatcga gtcacaaaga aatgtttgtt    840
```

```
ttcttaaaac atctgaaagt ggcacaccaa gttcctctac tcctcaagaa aacaccacat    900
ctggatacag ccttttaacc tgcaaaaaaa ctttacctga accctgccat tctaaaattt    960
acccgggagt tgactttgga ggagaagaat tgaatgtgac ttttgttaaa ggagtgaatg   1020
tttgccaaga gacttgtaca aagatgattc gctgtcagtt tttcacttat tctttactac   1080
cagaagactg taaggaggag aagtgtaagt gtttcttaag attatcttcg gatggttctc   1140
caactaggat tacatatggg acacaaggga gctctggtta ctctttgaga ttgtgtaaca   1200
ctggggacag ctctgtctgc acaacaaaaa caagctcacg cattgttgga ggaacaaact   1260
cttcttgggg agagtggccc tggcaggtga gcctgcaggt gaagctgatg gctcagaggc   1320
acctgtgtgg agggtcactc ataggacacc agtgggtcct cactgctgcc cactgctttg   1380
atgggcttcc cttaccggat gtttggcgca tttatagtgg cattttaaat ctgtcagaca   1440
ttacaaaaga aacacctttc tcacaaataa aagagatcat tattcaccaa aactatagaa   1500
tctcagaagg gaatcatgat atcgccttaa taaaactcca gactcctttg aattacactg   1560
aattccaaaa accaatatgc ctaccttcca aaggtgacac aaacacaatt tataccaact   1620
gttgggtaac tggatggggc ttctcgaagg aaaaaggtga aatccaagat attctacaaa   1680
aggtaaatat tcctttggta acaaatgaag aatgccagaa aagatatcaa gattataaaa   1740
taacccaacg gatggtctgt gctggctata aagaaggggg aaaagatgct tgtaagggag   1800
attcaggggg tcccttagct tgcaaacaca atggaatgtg gcgtttggtg ggcatcacca   1860
gctggggcga aggctgtgcc cgcagggagc aacctggtgt ctacaccaaa gtcgctgagt   1920
acatggactg gattttagag aaaacacaga gcagtgatgg aaatgctcgg atgcaggcgc   1980
cagcatgagg agcagcccag agtcttggcg agttttacaa cctgggttca agtcaaattc   2040
tgagcctggg ggtcctcatc tgcaaagcat ggagagtggc atctactttg catcctgtca   2100
taaggacaaa agacagtgca ctcagagctg ctgaggacaa tgttttgctg aagccagctt   2160
tcagcattca gtaactggga gctgattgat gaactacctg catttatttt atttgttt     2218
```

<210> SEQ ID NO 20
<211> LENGTH: 21
<212> TYPE: DNA
<213> ORGANISM: Artificial sequence
<220> FEATURE:
<223> OTHER INFORMATION: Primer

<400> SEQUENCE: 20

```
tgcctgctgt tcagctttct c                                               21
```

<210> SEQ ID NO 21
<211> LENGTH: 21
<212> TYPE: DNA
<213> ORGANISM: Artificial sequence
<220> FEATURE:
<223> OTHER INFORMATION: Primer

<400> SEQUENCE: 21

```
tggcaaagtc cctgtaatgc t                                               21
```

<210> SEQ ID NO 22
<211> LENGTH: 30
<212> TYPE: DNA
<213> ORGANISM: Artificial sequence
<220> FEATURE:
<223> OTHER INFORMATION: Probe

<400> SEQUENCE: 22
cgtgactcca cccaaagaga caaataaacg 30

<210> SEQ ID NO 23
<211> LENGTH: 17
<212> TYPE: DNA
<213> ORGANISM: Artificial sequence
<220> FEATURE:
<223> OTHER INFORMATION: Primer

<400> SEQUENCE: 23
tcggttgccc catggat 17

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
ggtgacgaca tggcttacat tc 22

<210> SEQ ID NO 25
<211> LENGTH: 27
<212> TYPE: DNA
<213> ORGANISM: Artificial sequence
<220> FEATURE:
<223> OTHER INFORMATION: Probe

<400> SEQUENCE: 25
ttttccagca ctttgccttt gcagacc 27

<210> SEQ ID NO 26
<211> LENGTH: 27
<212> TYPE: DNA
<213> ORGANISM: Artificial sequence
<220> FEATURE:
<223> OTHER INFORMATION: Primer

<400> SEQUENCE: 26
acaagtgcat tttacagacc agagtac 27

<210> SEQ ID NO 27
<211> LENGTH: 22
<212> TYPE: DNA
<213> ORGANISM: Artificial sequence
<220> FEATURE:
<223> OTHER INFORMATION: Primer

<400> SEQUENCE: 27
ggttgtccgc tgactttatg ct 22

<210> SEQ ID NO 28
<211> LENGTH: 24
<212> TYPE: DNA
<213> ORGANISM: Artificial sequence
<220> FEATURE:
<223> OTHER INFORMATION: Probe

<400> SEQUENCE: 28
aagcacagtg caagcggaac accc 24

<210> SEQ ID NO 29
<211> LENGTH: 25

-continued

```
<212> TYPE: DNA
<213> ORGANISM: Artificial sequence
<220> FEATURE:
<223> OTHER INFORMATION: Primer

<400> SEQUENCE: 29

agacccattt cctcaaggta gaact                                            25


<210> SEQ ID NO 30
<211> LENGTH: 16
<212> TYPE: DNA
<213> ORGANISM: Artificial sequence
<220> FEATURE:
<223> OTHER INFORMATION: Primer

<400> SEQUENCE: 30

cgcagcgacg ctcatg                                                      16


<210> SEQ ID NO 31
<211> LENGTH: 25
<212> TYPE: DNA
<213> ORGANISM: Artificial sequence
<220> FEATURE:
<223> OTHER INFORMATION: Probe

<400> SEQUENCE: 31

tctttgggtc cagtggcacc ctctt                                            25


<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32

ggcatattgg tttttggaat                                                  20
```